US012679816B2

(12) United States Patent
Choi et al.

(10) Patent No.: US 12,679,816 B2
(45) Date of Patent: Jul. 14, 2026

(54) ORGANIC LIGHT EMITTING DEVICE

(71) Applicant: LG DISPLAY CO., LTD., Seoul (KR)

(72) Inventors: Su-Na Choi, Paju-si (KR); In-Bum Song, Paju-si (KR); Jeong-Dae Seo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 1061 days.

(21) Appl. No.: 17/524,184

(22) Filed: Nov. 11, 2021

(65) Prior Publication Data

US 2022/0216410 A1 Jul. 7, 2022

(30) Foreign Application Priority Data

Dec. 28, 2020 (KR) ........................ 10-2020-0184940

(51) Int. Cl.
*C07D 307/91* (2006.01)
*C07C 15/28* (2006.01)
(Continued)

(52) U.S. Cl.
CPC ............ *C07D 307/91* (2013.01); *C07C 15/28* (2013.01); *C07F 5/027* (2013.01); *C09K 11/06* (2013.01);
(Continued)

(58) Field of Classification Search
None
See application file for complete search history.

(56) References Cited

U.S. PATENT DOCUMENTS

2012/0126208 A1* 5/2012 Kawamura ........ H10K 85/6572 257/E51.026
2015/0060825 A1* 3/2015 Song ...................... H10K 50/19 257/40
(Continued)

FOREIGN PATENT DOCUMENTS

EP 3544986 B1 * 12/2020 ........... C07D 498/14
KR 10-2020-0081983 A 7/2020
(Continued)

OTHER PUBLICATIONS

Liu, G., Sasabe, H., Kumada, K., Matsunaga, A., Katagiri, H., & Kido, J. (2021). Facile synthesis of multi-resonance ultra-pure-green TADF emitters based on bridged diarylamine derivatives for efficient OLEDs with narrow emission. Journal of Materials Chemistry C, 9(26), 8308-8313. (Year: 2021).*
(Continued)

*Primary Examiner* — Dawn L Garrett
(74) *Attorney, Agent, or Firm* — Morgan, Lewis & Bockuis LLP

(57) ABSTRACT

The present disclosure relates to an organic light emitting device. In particular, the present disclosure relates to an organic light emitting diode and an organic light emitting device each of which includes at least one emitting material layer comprising a boron-based dopant and an anthracene-based host substituted with at least one deuterium, at least one electron blocking layer including an amine-based compound substituted with at least one spiro aryl group, and optionally at least one hole blocking layer including an azine-based or a benzimidazole-based compound. The organic light emitting diode and the organic light emitting device has improved luminous efficiency and enhanced luminous lifespan.

13 Claims, 8 Drawing Sheets

D4

(51) Int. Cl.

| | |
|---|---|
| ***C07F 5/02*** | (2006.01) |
| ***C09K 11/06*** | (2006.01) |
| ***H10K 50/11*** | (2023.01) |
| ***H10K 50/18*** | (2023.01) |
| ***H10K 85/60*** | (2023.01) |

(52) U.S. Cl.

CPC ......... *H10K 85/615* (2023.02); *H10K 85/626* (2023.02); *H10K 85/6574* (2023.02); *H10K 85/658* (2023.02); *C07B 2200/05* (2013.01); *C07C 2603/24* (2017.05); *C09K 2211/10* (2013.01); *C09K 2211/1007* (2013.01); *C09K 2211/1011* (2013.01); *C09K 2211/1018* (2013.01); *H10K 50/11* (2023.02); *H10K 50/181* (2023.02)

(56) References Cited

U.S. PATENT DOCUMENTS

| | | | | |
|---|---|---|---|---|
| 2019/0296243 | A1* | 9/2019 | Suh | H10K 85/615 |
| 2019/0305227 | A1* | 10/2019 | Yoon | C07D 409/10 |
| 2020/0098991 | A1* | 3/2020 | Kim | C09K 11/06 |
| 2021/0320265 | A1 | 10/2021 | Song et al. | |
| 2022/0173318 | A1 | 6/2022 | Kim et al. | |
| 2023/0047477 | A1 | 2/2023 | Tasaki et al. | |

FOREIGN PATENT DOCUMENTS

| | | | |
|---|---|---|---|
| KR | 10-2020-0132752 | A | 11/2020 |
| WO | 2020080417 | A1 | 4/2020 |
| WO | 2020138877 | A1 | 7/2020 |

OTHER PUBLICATIONS

Office Action dated Dec. 2, 2024, issued in corresponding Korean Patent Office Application No. 10-2020-0184940.

Office Action dated Feb. 21, 2025 issued in corresponding Chinese Patent Application No. 202111368124.1 with English translation. (Note: KR 102191018 B1 and WO 2020138872 A1 were previously cited.).

* cited by examiner

ORGANIC LIGHT EMITTING DEVICE

CROSS-REFERENCE TO RELATED APPLICATIONS

This application claims the priority benefit under 35 U.S.C. § 119(a) of Korean Patent Application No. 10-2020-0184940 filed in the Republic of Korea on Dec. 28, 2020, the entire contents of which are expressly incorporated herein by reference in its entirety into the present application.

BACKGROUND

Technical Field

The present disclosure relates to an organic light emitting device, and more specifically, to an organic light emitting device having excellent luminous efficiency and luminous lifespan.

Discussion of the Related Art

An organic light emitting diode (OLED) among a flat display device used widely has come into the spotlight as a display device replacing rapidly a liquid crystal display device (LCD). The OLED can be formed as a thin organic film less than 2000 Å and can implement unidirectional or bidirectional images by electrode configurations. Also, the OLED can be formed even on a flexible transparent substrate such as a plastic substrate so that a flexible or a foldable display device can be realized with ease using the OLED. In addition, the OLED can be driven at a lower voltage and the OLED has excellent high color purity compared to the LCD.

Since fluorescent material uses only singlet exciton energy in the luminous process, the related art fluorescent material shows low luminous efficiency. On the contrary, phosphorescent material can show high luminous efficiency since it uses triplet exciton energy as well as singlet exciton energy in the luminous process. However, metal complex, representative phosphorescent material, has short luminous lifespan for commercial use. Particularly, blue luminous materials have not showed satisfactory luminous efficiency and luminous lifespan compared to other color luminous materials. Therefore, there is a need to develop a new compound or a device structure that can enhance luminous efficiency and luminous lifespan of the organic light emitting diode.

SUMMARY

Accordingly, embodiments of the present disclosure are directed to an organic light emitting device that substantially obviates one or more of the problems due to the limitations and disadvantages of the related art.

An aspect of the present disclosure is to provide an organic light emitting device with improved luminous efficiency and luminous lifespan.

Additional features and aspects will be set forth in the description that follows, and in part will be apparent from the description, or can be learned by practice of the inventive concepts provided herein. Other features and aspects of the inventive concept can be realized and attained by the structure particularly pointed out in the written description, or derivable therefrom, and the claims hereof as well as the appended drawings.

To achieve these and other aspects of the inventive concepts, as embodied and broadly described herein, an organic light emitting device comprises a substrate; and an organic light emitting diode over the substrate, the organic light emitting diode including a first electrode, a second electrode facing the first electrode and an emissive layer disposed between the first electrode and the second electrode, wherein the emissive layer comprises a first emitting material layer including a first dopant and a first host and a first electron blocking layer disposed between the first electrode and the first emitting material layer, wherein the first dopant includes a boron-based compound having the following structure of Formula 1A or Formula 1B, wherein the first host includes an anthracene-based compound having the following structure of Formula 3, and wherein the first electron blocking layer includes an amine-based compound having the following structure of Formula 5:

[Formula 1A]

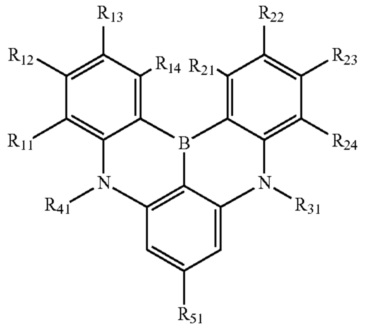

wherein each of $R_{11}$ to $R_{14}$ and each of $R_{21}$ to $R_{24}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, or adjacent two of $R_{11}$ to $R_{14}$ and $R_{21}$ to $R_{24}$ form a fused ring, wherein each of the aryl group, the aryl amino group, the hetero aryl group and the alicyclic group of $R_{11}$ to $R_{14}$ and $R_{21}$ to $R_{24}$ is independently unsubstituted or substituted with at least one $C_1$-$C_{10}$ alkyl group; each of $R_{31}$ and $R_{41}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, wherein each of the aryl group, the aryl amino group, the hetero aryl group and the alicyclic group of $R_{31}$ and $R_{41}$ is independently unsubstituted or substituted with at least one $C_1$-$C_{10}$ alkyl group; $R_{51}$ is selected form the group consisting of hydrogen, a $C_1$-$C_{10}$ alkyl group, a $C_3$-$C_{15}$ cyclo alkyl group, a $C_6$-$C_{30}$ aryl group, a $C_6$-$C_{30}$ aryl amino group, a $C_5$-$C_{30}$ hetero aryl group. a $C_3$-$C_{30}$ alicyclic group and a $C_5$-$C_{30}$ hetero cyclic group, wherein each of the cyclo alkyl group, the aryl group, the aryl amino group, the hetero aryl group, the alicyclic group and the hetero cyclic group of $R_{51}$ is independently unsubstituted or substituted with at least one $C_1$-$C_{10}$ alkyl group; when each of $R_{31}$, $R_{41}$ and $R_{51}$ is a $C_6$-$C_{30}$ aryl group substituted with at least one $C_1$-$C_{10}$ alkyl group, the substituted alkyl group is linked to each other to form a fused ring;

[Formula 1B]

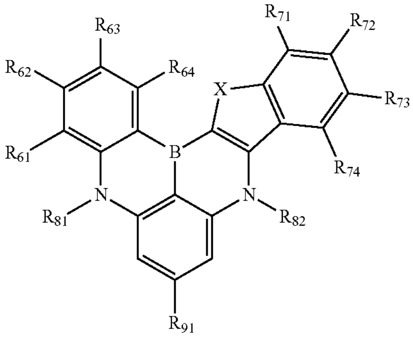

wherein X is $NR_1$, $CR_2R_3$, O, S, Se or $SiR_4R_5$, each of $R_1$ to $R_5$ is independently selected from the group consisting of hydrogen, a $C_1$-$C_{10}$ alkyl group, a $C_6$-$C_{30}$ aryl group, a $C_5$-$C_{30}$ hetero aryl group and a $C_3$-$C_{30}$ alicyclic group; each of $R_{61}$ to $R_{64}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, or adjacent two of $R_{61}$ to $R_{64}$ form a fused ring, wherein each of the aryl group, the aryl amino group, the hetero aryl group and the alicyclic group of $R_{61}$ to $R_{64}$ is independently unsubstituted or substituted with at least one $C_1$-$C_{10}$ alkyl group; each of $R_{71}$ to $R_{74}$ is independently selected from the group consisting of hydrogen, a $C_1$-$C_{10}$ alkyl group and a $C_3$-$C_{30}$ alicyclic group; $R_{81}$ is selected from the group consisting of a $C_6$-$C_{30}$ aryl group, a $C_5$-$C_{30}$ hetero aryl group and a $C_3$-$C_{30}$ alicyclic group, or $R_{81}$ and $R_{61}$ form a fused ring, wherein each of the aryl group, the hetero aryl group and the alicyclic group of $R_{81}$ is independently unsubstituted or substituted with at least one $C_1$-$C_{10}$ alkyl group; $R_{82}$ is selected from the group consisting of a $C_6$-$C_{30}$ aryl group, a $C_5$-$C_{30}$ hetero aryl group and a $C_3$-$C_{30}$ alicyclic group, wherein each of the aryl group, the hetero aryl group and the alicyclic group of $R_{82}$ is independently unsubstituted or substituted with at least one $C_1$-$C_{10}$ alkyl group; $R_{91}$ is selected from the group consisting of hydrogen, a $C_1$-$C_{10}$ alkyl group, a $C_3$-$C_{15}$ cyclo alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, wherein each of the cyclo alkyl group, the aryl group, the aryl amino group, the hetero aryl group and the alicyclic group of $R_{91}$ is independently unsubstituted or substituted with at least one $C_1$-$C_{10}$ alkyl group; when each of $R_{81}$, $R_{82}$ and $R_{91}$ is a $C_6$-$C_{30}$ aryl group substituted with at least one $C_1$-$C_{10}$ alkyl group, the substituted alkyl group is linked to each other to form a fused ring;

[Formula 3]

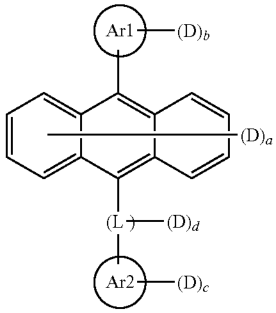

wherein each of Ar1 and Ar2 is independently a $C_6$-$C_{30}$ aryl group or a $C_5$-$C_{30}$ hetero aryl group; L is a single bond, a $C_6$-$C_{20}$ arylene group or a $C_5$-$C_{20}$ hetero arylene group; a is an integer of 0 to 8; each of b, c and d is independently an integer of 0 to 30, wherein at least one of a, b, c and d is a positive integer;

[Formula 5]

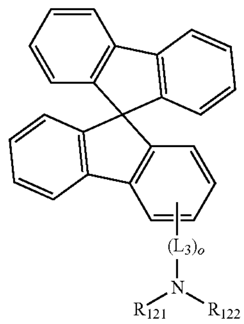

wherein $L_3$ is $C_6$-$C_{30}$ arylene; o is 0 or 1; each of $R_{121}$ and $R_{122}$ is independently $C_6$-$C_{30}$ aryl or $C_5$-$C_{30}$ hetero aryl, wherein each of the $C_6$-$C_{30}$ aryl and the $C_5$-$C_{30}$ hetero aryl is optionally substituted with at least one of $C_1$-$C_{10}$ alkyl and $C_6$-$C_{30}$ aryl, respectively.

As an example, each of $R_{11}$ to $R_{14}$, $R_{21}$ to $R_{24}$, $R_{31}$ and $R_{41}$ in Formula 1A may be independently selected from the group consisting of hydrogen, a $C_1$-$C_{10}$ alkyl group, a $C_6$-$C_{30}$ aryl group and a $C_5$-$C_{30}$ hetero aryl group, wherein each of the aryl group and the hetero aryl group of $R_{11}$ to $R_{14}$, $R_{21}$ to $R_{24}$, $R_{31}$ and $R_{41}$ may be independently unsubstituted or substituted with a $C_1$-$C_{10}$ alkyl group, wherein $R_{51}$ in Formula 1A may be selected from the group consisting of $C_1$-$C_{10}$ alkyl group, a $C_6$-$C_{30}$ aryl amino group, a $C_5$-$C_{30}$ hetero aryl group and a $C_3$-$C_{30}$ hetero cyclic group, and wherein each of the hetero aryl group, the aryl amino group and the hetero cyclic group of $R_{51}$ may be independently unsubstituted or substituted with a $C_1$-$C_{10}$ alkyl group.

Alternatively, X in Formula 1B may be O or S, wherein each of $R_{61}$ to $R_{64}$ in Formula 1B may be independently selected from the group consisting of hydrogen, a $C_1$-$C_{10}$ alkyl group and a $C_6$-$C_{30}$ aryl amino group, or adjacent two of $R_{61}$ to $R_{64}$ may form fused ring, wherein each of $R_{71}$ to $R_{74}$ may be independently selected from the group consisting of hydrogen and a $C_1$-$C_{10}$ alkyl group, wherein $R_{81}$ may be selected from the group consisting of a $C_6$-$C_{30}$ aryl group and a $C_5$-$C_{30}$ hetero aryl group, or $R_{81}$ and $R_{61}$ may form a fused ring, wherein each of the aryl group and the hetero aryl group of $R_{81}$ may be independently unsubstituted or substituted with a $C_1$-$C_{10}$ alkyl group, wherein $R_{82}$ may be selected from the group consisting of a $C_6$-$C_{30}$ aryl group and a $C_5$-$C_{30}$ hetero aryl group, wherein each of the aryl group and the hetero aryl group of $R_{82}$ may be independently unsubstituted or substituted with a $C_1$-$C_{10}$ alkyl group, and wherein $R_{91}$ may be a $C_1$-$C_{10}$ alkyl group.

The emissive layer may further comprise a first hole blocking layer disposed between the first emitting material layer and the second electrode.

As an example, the first hole blocking layer may comprise at least one of an azine-based compound having the following structure of Formula 7 and a benzimidazole-based compound having the following structure of Formula 9:

[Formula 7]

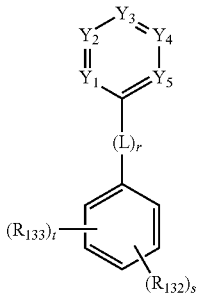

wherein each of $Y_1$ to $Y_5$ is independently $CR_{131}$ or N, one to three of $Y_1$ to $Y_5$ is N, and $R_{131}$ is a $C_6$-$C_{30}$ aryl group; L is a $C_6$-$C_{30}$ arylene group; $R_{132}$ is a $C_6$-$C_{30}$ aryl group or a $C_5$-$C_{30}$ hetero aryl group, wherein the $C_6$-$C_{30}$ aryl group is optionally substituted with another $C_6$-$C_{30}$ aryl or $C_5$-$C_{30}$ hetero aryl or forms a spiro structure with a $C_{10}$-$C_{30}$ fused aryl ring or a $C_{10}$-$C_{30}$ fused hetero aryl ring, wherein the another $C_6$-$C_{30}$ aryl is optionally further substituted with other $C_6$-$C_{30}$ aryl or $C_5$-$C_{30}$ hetero aryl or forms a spiro structure with a $C_{10}$-$C_{30}$ fused aryl ring; $R_{133}$ is hydrogen or adjacent two of $R_{133}$ form a fused aromatic ring; r is 0 or 1; s is 1 or 2; and t is an integer of 0 to 4;

[Formula 9]

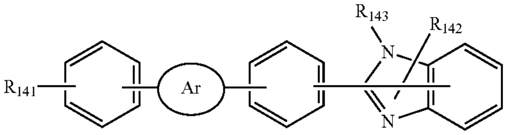

wherein Ar is $C_{10}$-$C_{30}$ arylene; $R_{141}$ is a $C_6$-$C_{30}$ aryl group or a $C_5$-$C_{30}$ hetero aryl group, each of the $C_6$-$C_{30}$ aryl group and the $C_5$-$C_{30}$ hetero aryl group is optionally substituted with $C_1$-$C_{10}$ alkyl; and each of $R_{142}$ and $R_{143}$ is independently hydrogen, a $C_1$-$C_{10}$ alkyl group or a $C_6$-$C_{30}$ aryl group.

Alternatively, the emissive layer may further comprise a second emitting material layer disposed between the first emitting material layer and the second electrode and a first charge generation layer disposed between the first and second emitting material layers.

The second emitting material layer may include a second dopant and a second host, wherein the second dopant may include the boron-based compound having the structure of Formula 1A or Formula 1B, and wherein the second host may include the anthracene-based compound having the structure of Formula 3.

In addition, the emissive layer may further comprise a second electron blocking layer disposed between the first charge generation layer and the second emitting material layer, and wherein the second electron blocking layer may include the amine-based compound having the structure of Formula 5.

The emissive layer may further comprise at least one of a first hole blocking layer disposed between the first emitting material layer and the first charge generation layer and a second hole blocking layer disposed between the second emitting material layer and the second electrode.

For example, the emissive layer may further comprise a third emitting material layer disposed between the second emitting material layer and the second electrode and a second charge generation layer disposed between the second and third emitting material layers.

The substrate may define a red pixel region, a green pixel region and a blue pixel region and the organic light emitting diode may be located correspondingly to the red pixel region, the green pixel region and the blue pixel region, and the organic light emitting device may further comprise a color conversion layer disposed between the substrate and the organic light emitting diode or over the organic light emitting diode correspondingly to the red pixel region and the green pixel region.

In one exemplary aspect, the second emitting material layer may emit yellow-green (YG) light or red-green (RG) light.

In this case, the substrate may define a red pixel region, a green pixel region and a blue pixel region and the organic light emitting diode may be located correspondingly to the red pixel region, the green pixel region and the blue pixel region, and the organic light emitting device may further comprise a color filter layer disposed between the substrate and the organic light emitting diode or over the organic light emitting diode correspondingly to the red pixel region, the green pixel region and the blue pixel region.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain various principles of the disclosure.

DETAILED DESCRIPTION

Reference will now be made in detail to embodiments of the disclosure, examples of which are illustrated in the accompanying drawings.

The organic light emitting diode of the present disclosure can enhance its luminous efficiency and its luminous lifespan by applying particular organic compounds into an emitting material layer, an electron blocking layer and/or a hole blocking layer. The organic light emitting diode can be applied into an organic light emitting device such as an organic light emitting display device or an organic light emitting illumination device.

Figure 1:
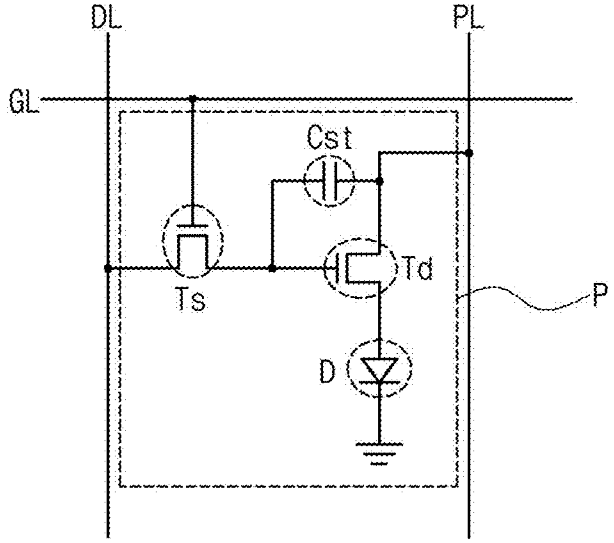
FIG. 1 is a schematic circuit diagram illustrating an organic light emitting display device in accordance with the present disclosure.

FIG. 1 is a schematic circuit diagram illustrating an organic light emitting display device of the present disclosure. As illustrated in FIG. 1, a gate line GL, a data line DL and power line PL, each of which cross each other to define a pixel region P, are formed in the organic light emitting display device. A switching thin film transistor Ts, a driving thin film transistor Td, a storage capacitor Cst and an organic light emitting diode D are formed within the pixel region P. The pixel region P may include a red (R) pixel region, a green (G) pixel region and a blue (B) pixel region.

The switching thin film transistor Ts is connected to the gate line GL and the data line DL, and the driving thin film transistor Td and the storage capacitor Cst are connected between the switching thin film transistor Ts and the power line PL. The organic light emitting diode D is connected to the driving thin film transistor Td. When the switching thin film transistor Ts is turned on by a gate signal applied into the gate line GL, a data signal applied into the data line DL is applied into a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the organic light emitting diode D through the driving thin film transistor Td. And then, the organic light emitting diode D emits light having a luminance proportional to the current flowing through the driving thin film transistor Td. In this case, the storage capacitor Cst is charge with a voltage proportional to the data signal so that the voltage of the gate electrode in the driving thin film transistor Td is kept constant during one frame. Therefore, the organic light emitting display device can display a desired image.

Figure 2:
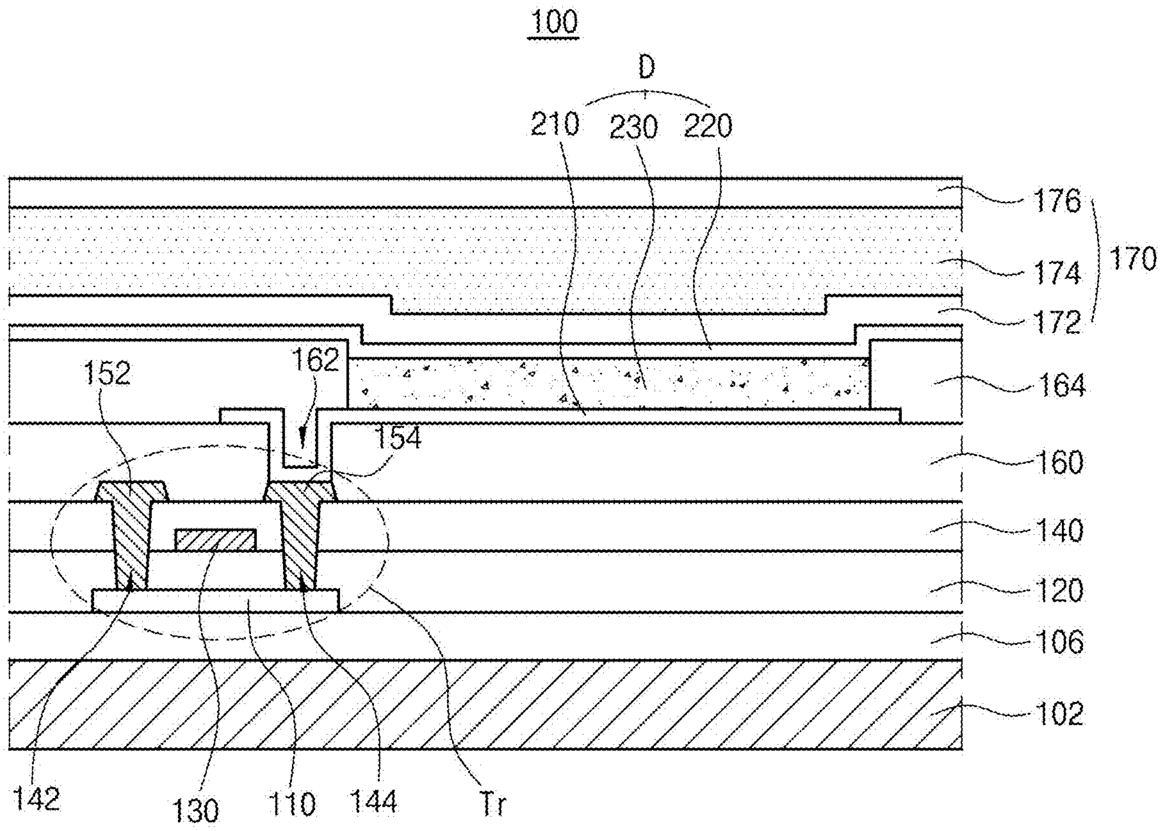
FIG. 2 is a cross-sectional view illustrating an organic light emitting display device as an example of an organic light emitting device in accordance with one exemplary aspect of the present disclosure.

FIG. 2 is a schematic cross-sectional view illustrating an organic light emitting display device in accordance with an exemplary aspect of the present disclosure. As illustrated in FIG. 2, the organic light emitting display device 100 comprises a substrate 102, a thin-film transistor Tr over the substrate 102, and an organic light emitting diode D connected to the thin film transistor Tr. As an example, the substrate 102 defines a red pixel region, a green pixel region and a blue pixel region and the organic light emitting diode D is located in each pixel region. In other words, the organic light emitting diode D, each of which emits red, green or blue (B) light, is located correspondingly in the red pixel region, the green pixel region and the blue pixel region.

The substrate 102 may include, but is not limited to, glass, thin flexible material and/or polymer plastics. For example, the flexible material may be selected from, but is not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode D are arranged, forms an array substrate.

A buffer layer 106 may be disposed over the substrate 102, and the thin film transistor Tr is disposed over the buffer layer 106. The buffer layer 106 may be omitted.

A semiconductor layer 110 is disposed over the buffer layer 106. In one exemplary aspect, the semiconductor layer 110 may include, but is not limited to, oxide semiconductor materials. In this case, a light-shield pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include polycrystalline silicon. In this case, opposite edges of the semiconductor layer 110 may be doped with impurities.

A gate insulating layer 120 including an insulating material is disposed on the semiconductor layer 110. The gate insulating layer 120 may include, but is not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 2, the gate insulating layer 120 may be patterned identically as the gate electrode 130.

An interlayer insulating layer 140 including an insulating material is disposed on the gate electrode 130 with covering over an entire surface of the substrate 102. The interlayer insulating layer 140 may include an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 2. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are made of conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 2 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may include amorphous silicon.

Although not shown in FIG. 2, a gate line and a data line, which cross each other to define a pixel region, and a switching element, which is connected to the gate line and the data line, is may be further formed in the pixel region. The switching element is connected to the thin film transistor Tr, which is a driving element. In addition, a power line is spaced apart in parallel from the gate line or the data line, and the thin film transistor Tr may further include a storage capacitor configured to constantly keep a voltage of the gate electrode for one frame.

A passivation layer 160 is disposed on the source and drain electrodes 152 and 154 with covering the thin film transistor Tr over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 144, it may be spaced apart from the second semiconductor layer contact hole 144.

The organic light emitting diode (OLED) D includes a first electrode 210 that is disposed on the passivation layer 160 and connected to the drain electrode 154 of the thin film transistor Tr. The organic light emitting diode D further includes an emissive layer 230 and a second electrode 220 each of which is disposed sequentially on the first electrode 210.

The first electrode 210 is disposed in each pixel region. The first electrode 210 may be an anode and include conductive material having relatively high work function value. For example, the first electrode 210 may include, but is not limited to, a transparent conductive oxide (TCO). Particularly, the first electrode 210 may include indium tin oxide (ITO), indium zinc oxide (IZO), indium tin zinc oxide (ITZO), SnO, ZnO, indium cerium oxide (ICO), aluminum doped zinc oxide (AZO), and the like.

In one exemplary aspect, when the organic light emitting display device 100 is a bottom-emission type, the first electrode 210 may have a single-layered structure of TCO. Alternatively, when the organic light emitting display device 100 is a top-emission type, a reflective electrode or a reflective layer may be disposed under the first electrode 210. For example, the reflective electrode or the reflective layer may include, but is not limited to, silver (Ag) or aluminum-palladium-copper (APC) alloy. In the organic light emitting display device 100 of the top-emission type, the first electrode 210 may have a triple-layered structure of ITO/Ag/ITO or ITO/APC/ITO.

In addition, a bank layer 164 is disposed on the passivation layer 160 in order to cover edges of the first electrode 210. The bank layer 164 exposes a center of the first electrode 210. The bank layer 164 may be omitted.

Figure 3:
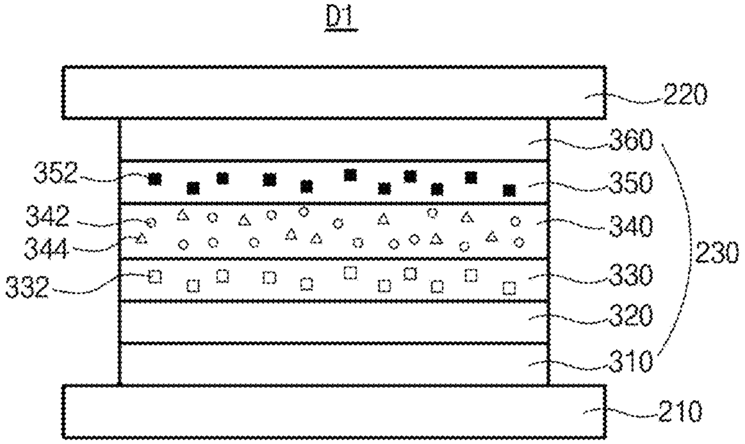
FIG. 3 is a cross-sectional view illustrating an organic light emitting diode having single emitting part in accordance with an exemplary aspect of the present disclosure.
Figure 4:
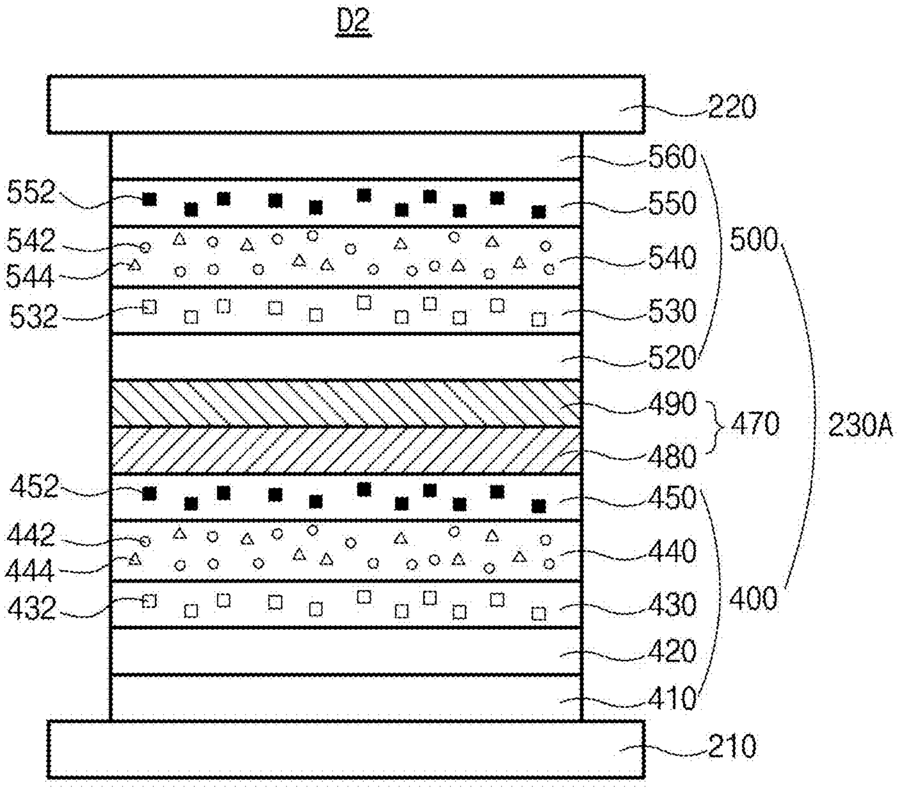
FIG. 4 is a cross-sectional view illustrating an organic light emitting diode having a double stack structure in accordance with another exemplary aspect of the present disclosure.

An emissive layer 230 is disposed on the first electrode 210. In one exemplary embodiment, the emissive layer 230 may have a mono-layered structure of an emitting material layer (EML). Alternatively, the emissive layer 230 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL), as illustrated in FIGS. 3 and 4. The emissive layer 230 may have a single emitting part or may have multiple emitting parts to form a tandem structure.

The emissive layer 230 may include at least one emitting material layer including an anthracene-based compound in which at least one hydrogen atom is deuterated and a boron-based compound in the blue pixel region, and at least one electron blocking layer including an aryl amine-based compound. Alternatively, the emissive layer 230 may further comprise at least one hole blocking layer including at least one of an azine-based compound and a benzimidazole-based compound. The emissive layer 230 enables the OLED D and the organic light emitting display device 100 to improve their luminous efficiency and luminous lifespan considerably.

The second electrode 220 is disposed over the substrate 102 above which the emissive layer 230 is disposed. The second electrode 220 may be disposed over a whole display area, and may include a conductive material with a relatively low work function value compared to the first electrode 210, and may be a cathode. For example, the second electrode 220 may include, but is not limited to, high-reflective material such as aluminum (Al), magnesium (Mg), calcium (Ca), silver (Ag), alloy thereof or combination thereof such as aluminum-magnesium alloy (Al—Mg). When the organic light emitting display device 100 is a top-emission type, the second electrode 220 is thin so that it has light transmissive (semi-transmissive) property.

In addition, an encapsulation film 170 may be disposed over the second electrode 220 in order to prevent outer moisture from penetrating into the organic light emitting diode D. The encapsulation film 170 may have, but is not limited to, a laminated structure of a first inorganic insulating film 172, an organic insulating film 174 and a second inorganic insulating film 176. The encapsulation film 170 may be omitted.

The organic light emitting display device 100 may further include a polarizing plate to reduce reflection of external light. For example, the polarizing plate may be a circular polarizing plate. When the organic light emitting display device 100 is a bottom-emission type, the polarizing plate may be located under the substrate 102. Alternatively, when the organic light emitting display device 100 is a top-emission type, the polarizing plate may be attached onto the encapsulation film 170. Further, a cover window may be attached onto the encapsulation film 170 or the polarizing plate in the organic light emitting display device 100 of the top-emission type. In this case, the substrate 102 and the cover window have flexible properties so that a flexible display device can be constructed.

As described above, the emissive layer 230 in the organic light emitting diode D includes particular compounds so that the organic light emitting diode D can enhance its luminous efficiency and its luminous lifespan. FIG. 3 is a schematic cross-sectional view illustrating an organic light emitting diode having a single emitting part in accordance with an exemplary embodiment of the present disclosure.

As illustrated in FIG. 3, the organic light emitting diode (OLED) D1 in accordance with the first embodiment of the present disclosure includes first and second electrodes 210 and 220 facing each other and an emissive layer 230 disposed between the first and second electrodes 210 and 220. In an exemplary embodiment, the emissive layer 230 includes an EML 340, which may be a first EML, disposed between the first and second electrodes 210 and 220 and an EBL 330, which may be a first EBL, disposed between the first electrode 210 and the EML 340. Alternatively, the emissive layer 230 may further include a HBL 350, which may be a first HBL, disposed between the EML 340 and the second electrode 220.

In addition, the emissive layer 230 may further include an HIL 310 disposed between the first electrode 210 and the EBL 330 and an HTL 320 disposed between the HIL 310 and the EBL 330. In addition, the emissive layer 230 may further include an EIL 360 disposed between the HBL 350 and the second electrode 220. In an alternative embodiment, the emissive layer 230 may further include an ETL disposed between the HBL 350 and the EIL 360. The organic light emitting display device 100 (FIG. 2) includes a red pixel region, a green pixel region and a blue pixel region, and the OLED D1 may be located in the blue pixel region.

One of the first and second electrodes 210 and 220 may be an anode and the other of the first and second electrodes 210 and 220 may be a cathode. Also, one of the first and second electrodes 210 and 220 may be a transmissive (semi-transmissive) electrode and the other of the first and second electrodes 210 and 220 may be a reflective electrode. For example, each of the first and second electrodes 210 and 220 may have a thickness of, but is not limited to, about 30 nm to about 300 nm.

The EML 340 includes a dopant 342, which may be a first dopant, of a boron-based compound and a host 344, which may be a first host, of an anthracene-based compound so that the EML 340 emits blue (B) light. In this case, the dopant 342 of the boron-based compound may not be deuterated or may be partially deuterated, while at least one hydrogen atoms in the host 344 of the anthracene-based compound may be deuterated. Namely, the host 344 in the EML 340 may be partially or fully deuterated, while the dopant 342 may not be deuterated or may be partially deuterated. The dopant 342 of the boron-based compound may have the following structure of Formula 1A or Formula 1B:

[Formula 1A]

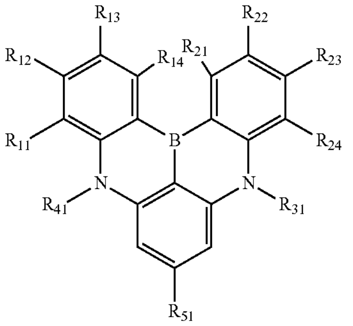

wherein each of $R_{11}$ to $R_{14}$ and each of $R_{21}$ to $R_{24}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, or adjacent two of $R_{11}$ to $R_{14}$ and $R_{21}$ to $R_{24}$ form a fused ring, wherein each of the aryl group, the aryl amino group, the hetero aryl group and the alicyclic group of $R_{11}$ to $R_{14}$ and $R_{21}$ to $R_{24}$ is independently unsubstituted or substituted with at least one $C_1$-$C_{10}$ alkyl group; each of $R_{31}$ and $R_{41}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, wherein each of the aryl group, the aryl amino group, the hetero aryl group and the alicyclic group of $R_{31}$ and $R_{41}$ is independently unsubstituted or substituted with at least one $C_1$-$C_{10}$ alkyl group; $R_{51}$ is selected form the group consisting of hydrogen, a $C_1$-$C_{10}$ alkyl group, a $C_3$-$C_{15}$ cyclo alkyl group, a $C_6$-$C_{30}$ aryl group, a $C_6$-$C_{30}$ aryl amino group, a $C_5$-$C_{30}$ hetero aryl group. a $C_3$-$C_{30}$ alicyclic group and a $C_5$-$C_{30}$ hetero cyclic group, wherein each of the cyclo alkyl group, the aryl group, the aryl amino group, the hetero aryl group, the alicyclic group and the hetero cyclic group of $R_{51}$ is independently unsubstituted or substituted with at least one $C_1$-$C_{10}$ alkyl group; when each of $R_{31}$, $R_{41}$ and $R_{51}$ is a $C_6$-$C_{30}$ aryl group substituted with at least one $C_1$-$C_{10}$ alkyl group, the substituted alkyl group is linked to each other to form a fused ring.

[Formula 1B]

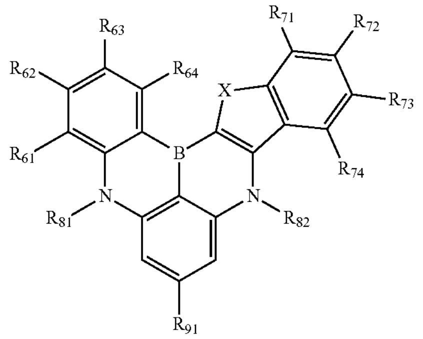

wherein X is $NR_1$, $CR_2R_3$, O, S, Se or $SiR_4R_5$, each of $R_1$ to $R_5$ is independently selected from the group consisting of hydrogen, a $C_1$-$C_{10}$ alkyl group, a $C_6$-$C_{30}$ aryl group, a $C_5$-$C_{30}$ hetero aryl group and a $C_3$-$C_{30}$ alicyclic group; each of $R_{61}$ to $R_{64}$ is independently selected from the group consisting of hydrogen, a $C_1$-$C_{10}$ alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, or adjacent two of $R_{61}$ to $R_{64}$ form a fused ring, wherein each of the aryl group, the aryl amino group, the hetero aryl group and the alicyclic group of $R_{61}$ to $R_{64}$ is independently unsubstituted or substituted with at least one $C_1$-$C_{10}$ alkyl group; each of $R_{71}$ to $R_{74}$ is independently selected from the group consisting of hydrogen, a $C_1$-$C_{10}$ alkyl group and a $C_3$-$C_{30}$ alicyclic group; $R_{81}$ is selected from the group consisting of a $C_6$-$C_{30}$ aryl group, a $C_5$-$C_{30}$ hetero aryl group and a $C_3$-$C_{30}$ alicyclic group, or $R_{81}$ and $R_{61}$ form a fused ring, wherein each of the aryl group, the hetero aryl group and the alicyclic group of $R_{81}$ is independently unsubstituted or substituted with at least one $C_1$-$C_{10}$ alkyl group; $R_{82}$ is selected from the group consisting of a $C_6$-$C_{30}$ aryl group, a $C_5$-$C_{30}$ hetero aryl group and a $C_3$-$C_{30}$ alicyclic group, wherein each of the aryl group, the hetero aryl group and the alicyclic group of $R_{82}$ is independently unsubstituted or substituted with at least one $C_1$-$C_{10}$ alkyl group; $R_{91}$ is selected from the group consisting of hydrogen, a $C_1$-$C_{10}$ alkyl group, a $C_3$-$C_{15}$ cyclo alkyl group, a $C_6$-$C_{30}$ aryl group, a $C_6$-$C_{30}$ aryl amino group, a $C_5$-$C_{30}$ hetero aryl group and a $C_3$-$C_{30}$ alicyclic group, wherein each of the cyclo alkyl group, the aryl group, the aryl amino group, the hetero aryl group and the alicyclic group of $R_{91}$ is independently unsubstituted or substituted with at least one $C_1$-$C_{10}$ alkyl group; when each of $R_{81}$, $R_{82}$ and $R_{91}$ is a $C_6$-$C_{30}$ aryl group substituted with at least one $C_1$-$C_{10}$ alkyl group, the substituted alkyl group is linked to each other to form a fused ring.

As an example, each of $R_{11}$ to $R_{14}$, $R_{21}$ to $R_{24}$, $R_{31}$ and $R_{41}$ in Formula 1A may be independently selected from the group consisting of hydrogen, a $C_1$-$C_{10}$ alkyl group, a $C_6$-$C_{30}$ aryl group and a $C_5$-$C_{30}$ hetero aryl group, wherein each of the aryl group and the hetero aryl group of $R_{11}$ to $R_{14}$, $R_{21}$ to $R_{24}$, $R_{31}$ and $R_{41}$ may be independently unsubstituted or substituted with a $C_1$-$C_{10}$ alkyl group, and $R_{51}$ in Formula 1A may be selected from the group consisting of $C_1$-$C_{10}$ alkyl group, a $C_6$-$C_{30}$ aryl amino group, a $C_5$-$C_{30}$ hetero aryl group and a $C_3$-$C_{30}$ hetero cyclic group, and wherein each of the hetero aryl group, the aryl amino group and the hetero cyclic group of $R_{51}$ may be independently unsubstituted or substituted with a $C_1$-$C_{10}$ alkyl group.

For example, one of $R_{11}$ to $R_{14}$ and/or one of $R_{21}$ to $R_{24}$ may be a $C_1$-$C_{10}$ alkyl group and the rest of $R_{11}$ to $R_{14}$ and/or the rest of $R_{21}$ to $R_{24}$ may be hydrogen, and each of $R_{31}$ and $R_{41}$ may be independently phenyl substituted with a $C_1$-$C_{10}$ alkyl group or a dibenzofuranyl substituted with a $C_1$-$C_{10}$ alkyl group in Formula 1A. $R_{51}$ in Formula 1A may be a $C_1$-$C_{10}$ alkyl group, a diphenyl amino group, a hetero aryl group including nitrogen atom or a hetero cyclic group including a nitrogen atom. In this case, the alkyl group may be, but is not limited to, tert-butyl. In addition, the fused ring formed by adjacent groups may be, but is not limited to, a $C_3$-$C_{10}$ alicyclic ring.

Alternatively, X in Formula 1B may be O or S, each of $R_{61}$ to $R_{64}$ in Formula 1B may be independently selected from the group consisting of hydrogen, a $C_1$-$C_{10}$ alkyl group and a $C_6$-$C_{30}$ aryl amino group, or adjacent two of $R_{61}$ to $R_{64}$ may form a fused ring, each of $R_{71}$ to $R_{74}$ may be independently selected from the group consisting of hydrogen and a $C_1$-$C_{10}$ alkyl group, $R_{81}$ may be selected from the group consisting of a $C_6$-$C_{30}$ aryl group and a $C_5$-$C_{30}$ hetero aryl group, or $R_{81}$ and $R_{61}$ may form a fused ring, wherein each of the aryl group and the hetero aryl group of $R_{81}$ may be independently unsubstituted or substituted with a $C_1$-$C_{10}$ alkyl group, $R_{82}$ may be selected from the group consisting of a $C_6$-$C_{30}$ aryl group and a $C_5$-$C_{30}$ hetero aryl group, wherein each of the aryl group and the hetero aryl group of $R_{82}$ may be independently unsubstituted or substituted with a $C_1$-$C_{10}$ alkyl group, and wherein $R_{91}$ may be a $C_1$-$C_{10}$ alkyl group.

For example, X in Formula 1B may be O. Each of $R_{61}$ to $R_{64}$ may be independently selected from the group consisting of protium, deuterium, a $C_1$-$C_{10}$ alkyl group and a diphenyl amino group, or adjacent two of $R_{61}$ to $R_{64}$ may form a fused ring, and the diphenyl amino group or the fused group may be deuterated. Each of $R_{71}$ to $R_{74}$ may be independently selected from the group consisting of protium, deuterium and a $C_1$-$C_{10}$ alkyl group. Each of $R_{81}$ and $R_{82}$ may be independently selected from the group consisting of phenyl and dibenzofuranyl each of which may be independently unsubstituted or substituted with deuterium and/or a $C_1$-$C_{10}$ alkyl group. $R_{91}$ may be a $C_1$-$C_{10}$ alkyl group such as tert-butyl, but is not limited thereto.

Alternatively, $R_{73}$ may be a $C_1$-$C_{10}$ alkyl group and each of $R_{71}$, $R_{72}$ and $R_{74}$ may be independently protium or deuterium in Formula 1B. For example, in the boron-based compound having the structure of Formula 1B, at least one protium linked to the aromatic ring and the heteroaromatic ring other than the aromatic ring linked to boron atom and two nitrogen atoms and the aromatic rings fused by those hetero aromatic rings may be substituted with deuterium. Namely, $R_{91}$ in Formula 1B may not be deuterated.

For example, the dopant 342 of the boron-based compound may be selected from, but is not limited to, the following compounds of Formula 2:

[Formula 2]

1-1

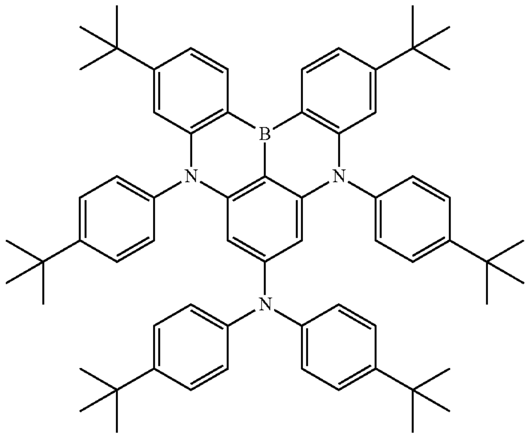

1-2

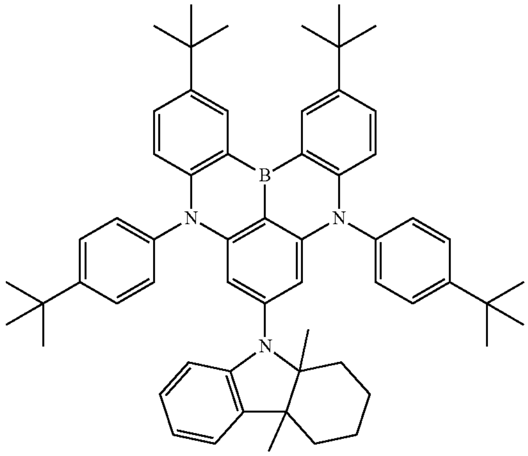

-continued
1-3
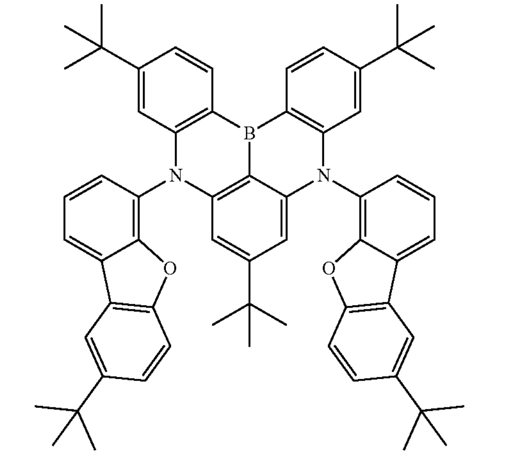
1-4
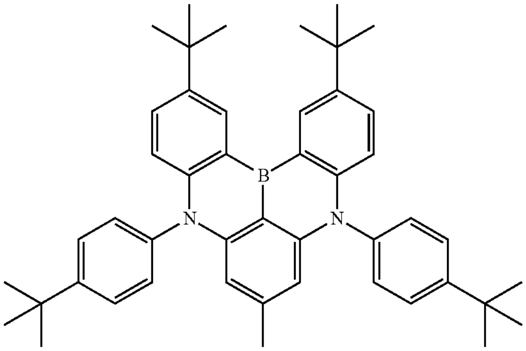
1-5
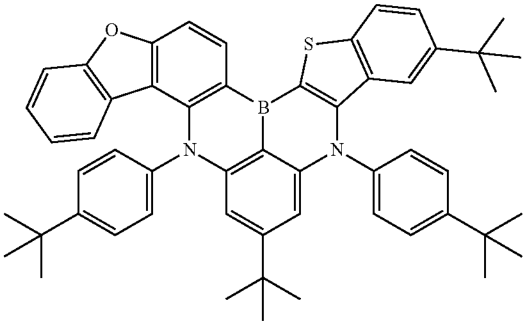
1-6
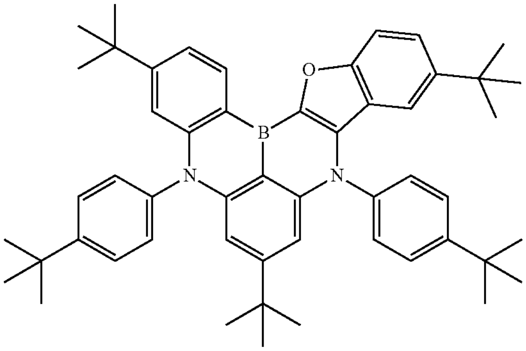
-continued
1-7
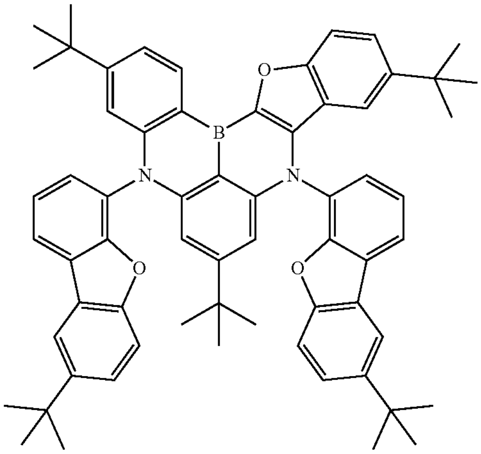
1-8
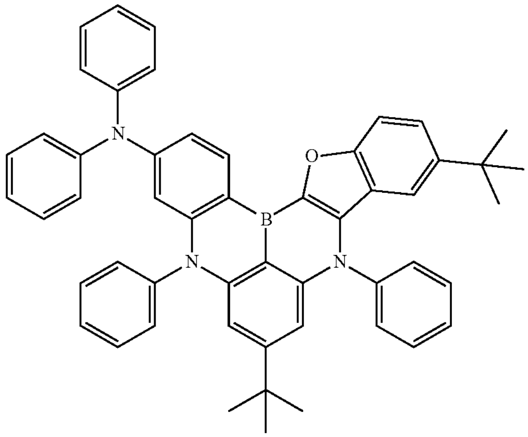
1-9
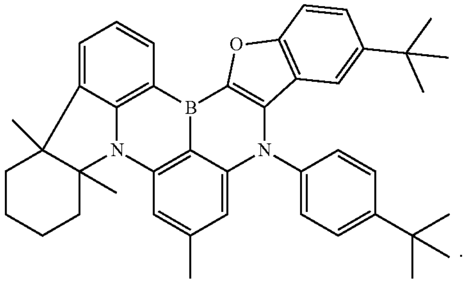
1-10
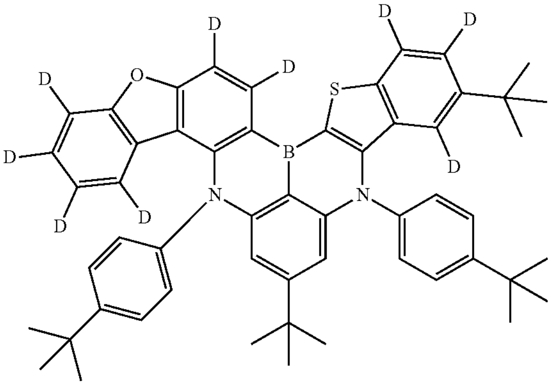

-continued
1-11
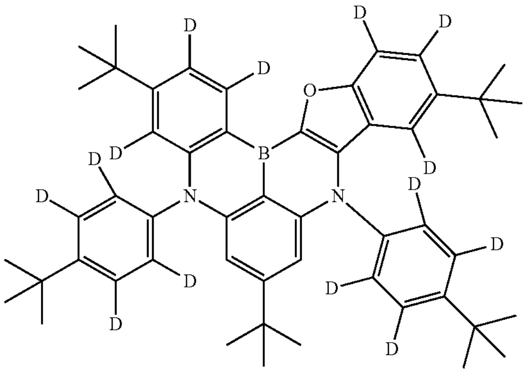
1-12
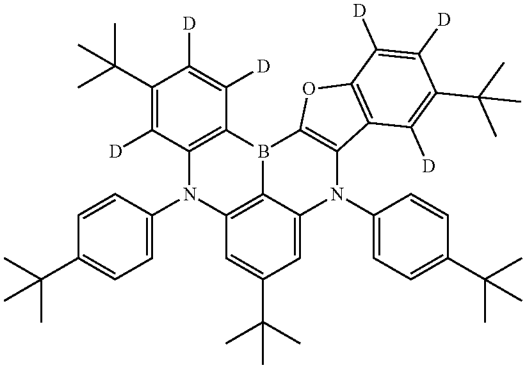
1-13
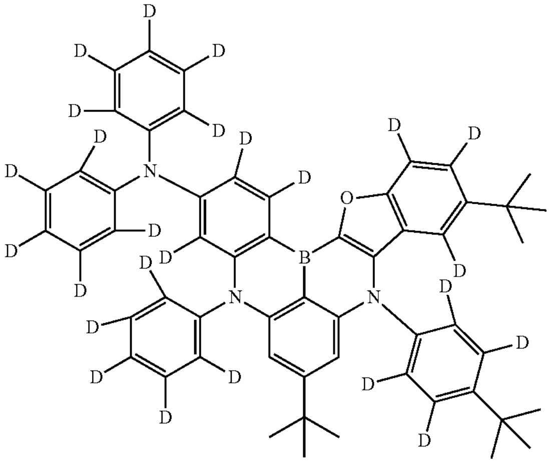
-continued
1-14
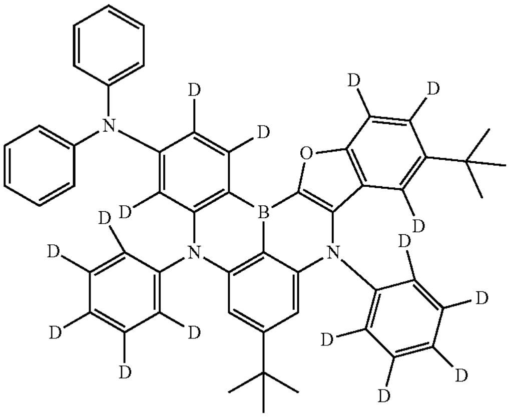
1-15
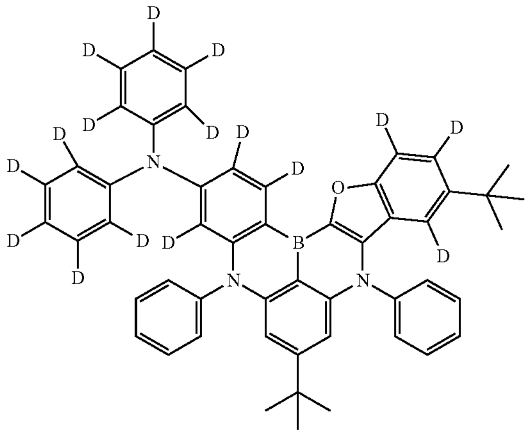
1-16
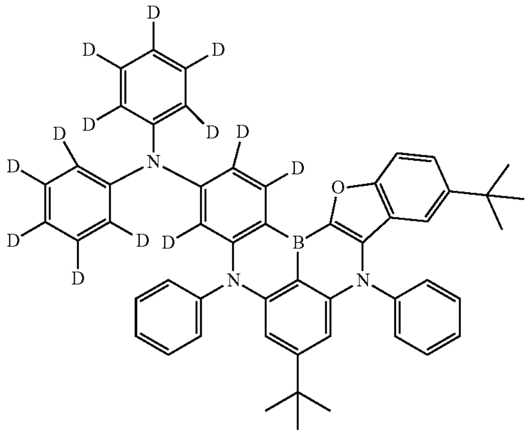

-continued 1-17

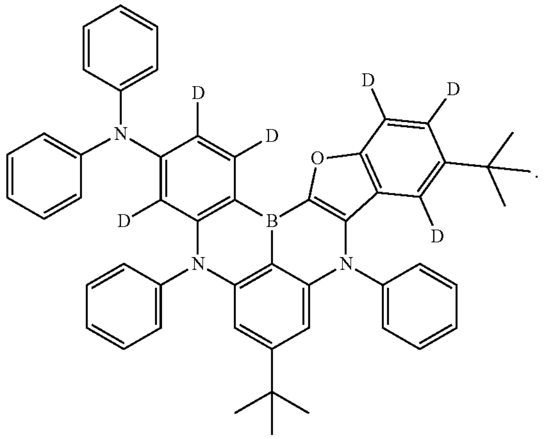

In another exemplary aspect, the host 344 of the anthracene-based compound may have the following structure of Formula 3:

[Formula 3]

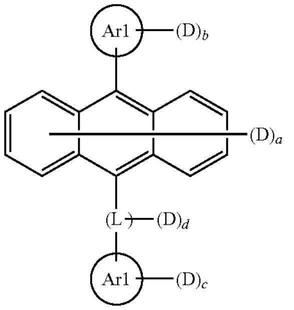

wherein each of Ar1 and Ar2 is independently a $C_6$-$C_{30}$ aryl group or a $C_5$-$C_{30}$ hetero aryl group; L is a single bond, a $C_6$-$C_{20}$ arylene group or a $C_5$-$C_{20}$ hetero arylene group; a is an integer of 0 to 8; each of b, c and d is independently an integer of 0 to 30, wherein at least one of a, b, c and d is a positive integer.

As an example, each of Ar1 and Ar2 may be independently phenyl, naphthyl, dibenzofuranyl or a fused dibenzofuranyl and L may be a single bond, phenylene or dibenzofuranylene in Formula 3. For example, Ar1 may be naphthyl, dibenzofuranyl or fused dibenzofuranyl and Ar2 may be phenyl or naphthyl in Formula 3. Alternatively, both Ar1 and Ar2 may be naphthyl and L may be a single bond, phenylene or dibenzofuranylene.

Particularly, 1-naphtyl moiety is linked directly to the anthracene moiety, 2-naphthyl moiety is linked directly or via phenylene linker (bridging group) to the anthracene moiety, and at least one protium, for example, all protiums, in the molecule may be deuterated.

For example, the host 344 of the anthracene-based compound may be selected from, but is not limited to, the following compound of Formula 4.

[Formula 4]

2-7

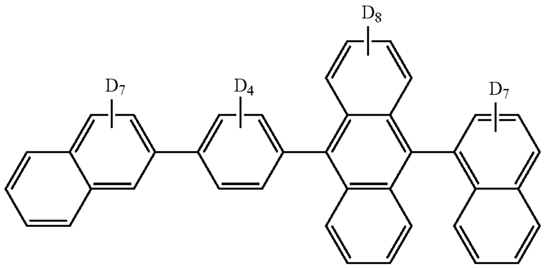

2-8

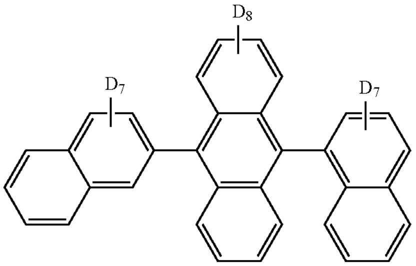

2-9

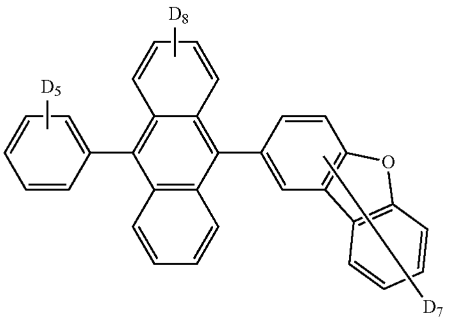

2-10

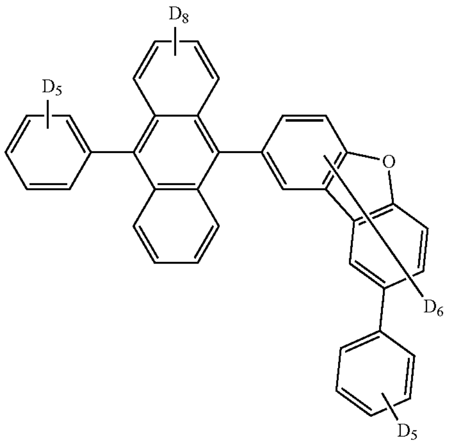

-continued 2-11

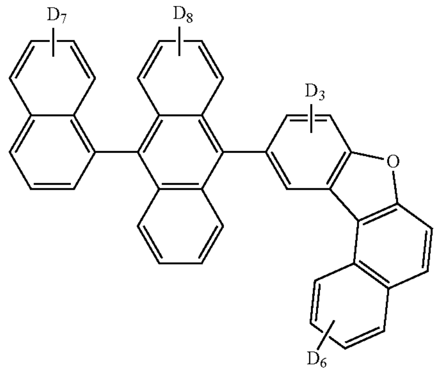

2-12

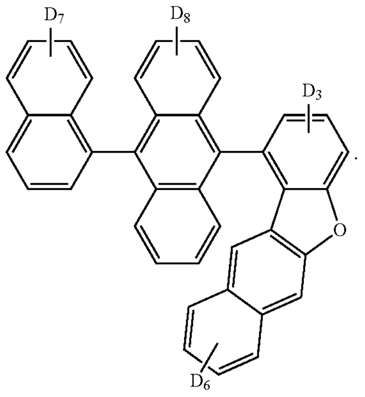

In one exemplary embodiment, the contents of the host 344 may be about 70 wt % to about 99.9 wt % and the contents of the dopant 342 may be about 0.1 wt % to about 30 wt % in the EML 340. For example, the contents of the dopant 342 in the EML 340 may be about 0.1 wt % to about 10 wt %, for example, about 1 wt % to about 5 wt % so that the EML 340 may implement sufficient luminous efficiency and luminous lifespan. The EML 340 may have a thickness of, but is not limited to, about 10 nm to about 200 nm, for example, about 20 nm to about 100 nm or about 20 nm to about 50 nm.

The EML 340 includes the dopant 342 of the boron-based compound and the host 344 of the anthracene-based compound substituted with at least one deuterium so that the OLED D1 and the organic light emitting display device 100 can improve their luminous efficiency and luminous lifespan. When the dopant 342 of the boron-based compound has an asymmetric chemical structure such as Formula 1B, the OLED D1 and the organic light emitting display device 100 can improve their luminous efficiency and luminous lifespan significantly.

In addition, when the EML 340 includes the dopant 342 where a part of or all protiums linked to the aromatic rings and the heteroaromatic rings other than the aromatic ring linked to boron atom and two nitrogen atoms may be substituted with deuterium, the OLED D1 and the organic light emitting display device 100 can improve further their luminous efficiency and luminous lifespan.

Moreover, when the EML 340 includes the host 344 of the anthracene-based compound where two naphthyl moieties are linked to directly or via a linker to the anthracene moiety and at least one, for example all protiums are deuterated, the luminous efficiency and the luminous lifespan of the OLED D1 and the organic light emitting display device 100 can be further enhanced.

The HIL 310 is disposed between the first electrode 210 and the HTL 320 and improves an interface property between the inorganic first electrode 210 and the organic HTL 320. In one exemplary embodiment, the HIL 310 may include a hole injection material selected from, but is not limited to, the group consisting of 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS), 2,3,5,6-tetrafluoro-7,7,8,8-tetracyanoquinodimethane (F4TCNQ), N-(biphenyl-4-yl)-9,9-dimethyl-N-(4-(9-phenyl-9H-carbazol-3-yl)phenyl)-9H-fluoren-2-amine and combination thereof.

Alternatively, the HIL 340 may comprise a hole injection host and a hole injection dopant. As an example, the hole injection host may comprise a spirofluorene-based compound having the following structure of Formula 11 and the hole injection dopant may comprise a radialene-based compound having the following structure of Formula 12, but is not limited thereto.

[Formula 11]

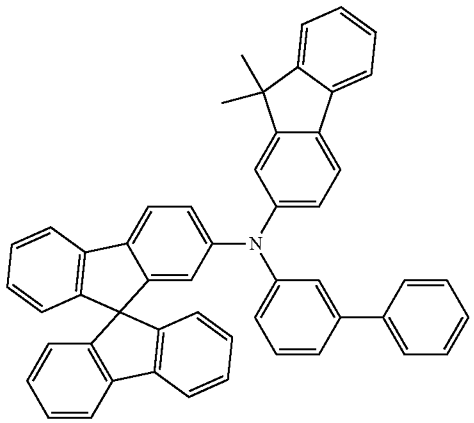

[Formula 12]

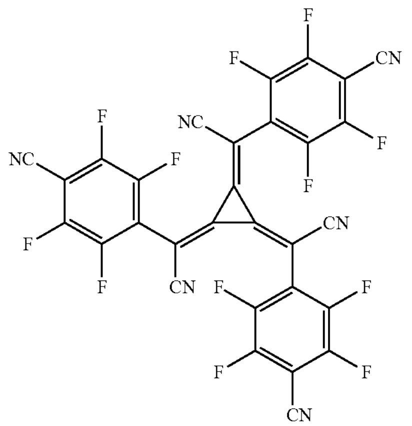

When the HIL 310 includes the hole injection host and the hole injection dopant, the contents of the hole injection dopant in the HIL 310 may be, but is not limited to, about 1 wt % to about 50 wt %, for example, about 1 wt % to about 30 wt %. The HIL 310 may be omitted in compliance of the OLED D1 property.

The HTL 320 is disposed between the HIL 310 and the EBL 330. In one exemplary embodiment, the HTL 320 may include a hole transport material selected from, but is not limited to, N,N'-Diphenyl-N,N'-bis(3-methylphenyl-1,1'-biphenyl-4,4'-diamine (TPD), NPB (NPD), N,N'-bis[4-[bis(3-methylphenyl)amino]phenyl]-N,N'-diphenyl-[1,1'-biphenyl]-4,4'-diamine (DNTPD), 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl)diphenylamine))] (TFB), 1,1-bis(4-(N,N'-di(p-tolyl)amino)phenyl)cyclohexane (TAPC), 3,5-Di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl)biphenyl-4-amine, N-([1,1'-Biphenyl]-4-yl)-9,9-dimethyl-N-(4-(9-phenyl-9H-carbazol-3-yl)phenyl)-9H-fluoren-2-amine, N4,N4,N4',N4'-tetrakis([1,1'-biphenyl]-4-yl)-[1,1'-biphenyl]-4,4'-diamine and/or the spirofluorene-based compound having the structure of Formula 11.

In an exemplary embodiment, each of the HIL 310 and the HTL 320 may independently have a thickness of, but is not limited to, about 5 nm to about 200 nm, for example, about 5 nm to about 100 nm.

The EBL 330 prevents electrons from transporting from the EML 340 to the first electrode 210. The EBL 330 may include an electron blocking material 332 of a spiroaryl amine-based compound having the following structure of Formula 5:

[Formula 5]

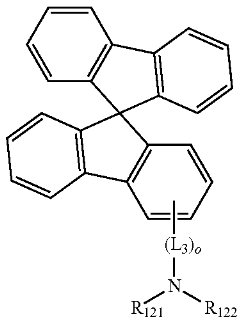

wherein $L_3$ is $C_6$-$C_{30}$ arylene; o is 0 or 1; each of $R_{121}$ and $R_{122}$ is independently $C_6$-$C_{30}$ aryl or $C_5$-$C_{30}$ hetero aryl, wherein each of the $C_6$-$C_{30}$ aryl and the $C_5$-$C_{30}$ hetero aryl is optionally substituted with at least one of $C_1$-$C_{10}$ alkyl and $C_6$-$C_{30}$ aryl, respectively.

As an example, $L_3$ may be phenylene and each of $R_{121}$ to $R_{122}$ may be independently unsubstituted or substituted with at least one of $C_1$-$C_{10}$ alkyl and $C_6$-$C_{30}$ aryl (e.g. phenyl), and may be selected from the group consisting of phenyl, biphenyl, fluorenyl, carbazolyl, phenyl carbazolyl, carbazolyl phenyl, dibenzofuranyl and dibenzothiophenyl.

For example, the electron blocking material 332 may be selected from any spiroaryl amine-based compounds having the following structure of Formula 6:

[Formula 6]

H1

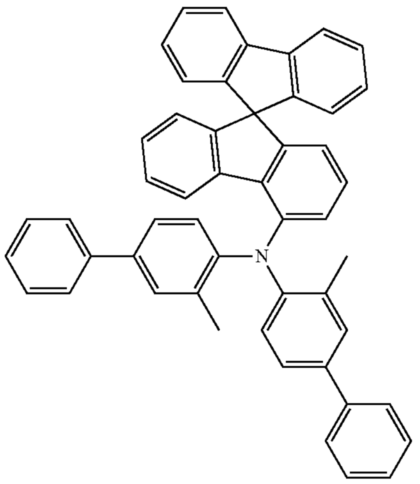

H2

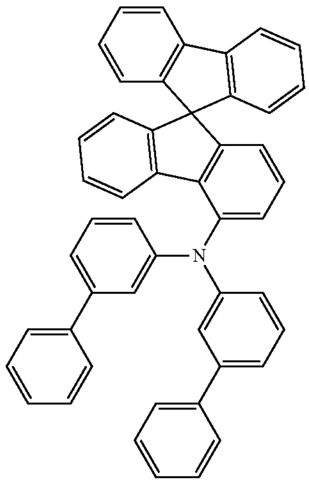

H3

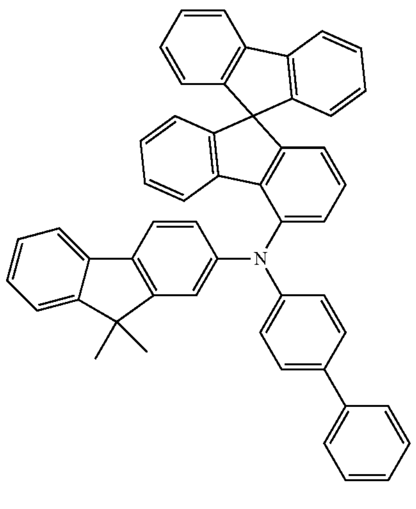

-continued
H4
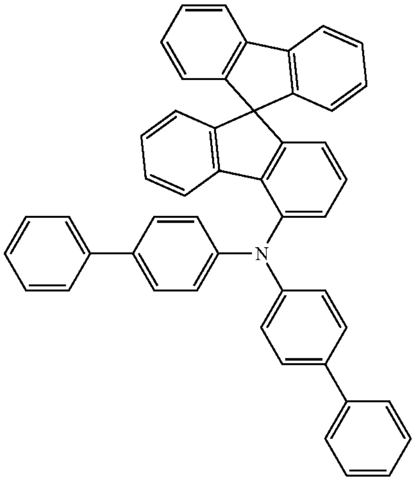
H5
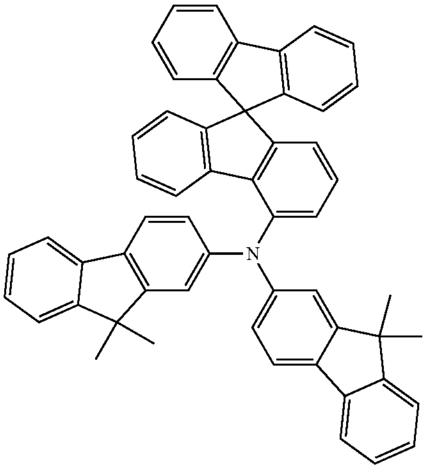
H6
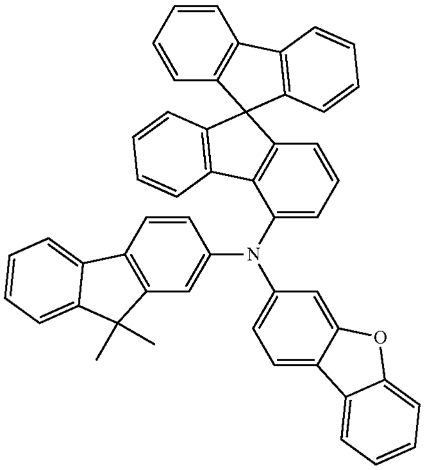
-continued
H7
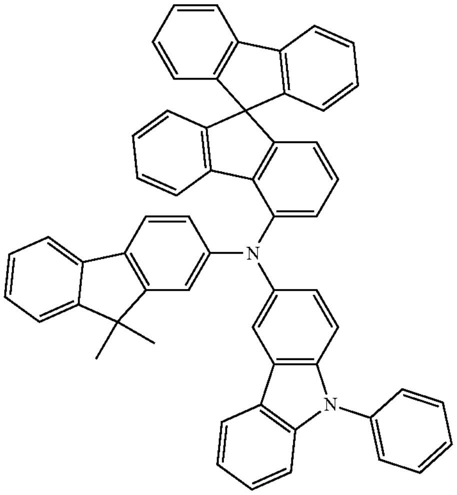
H8
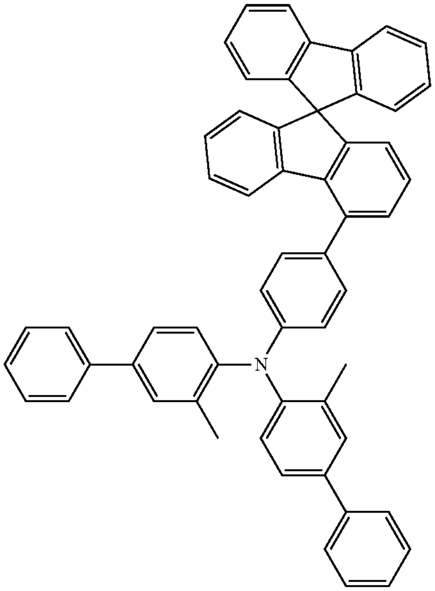

-continued
H9
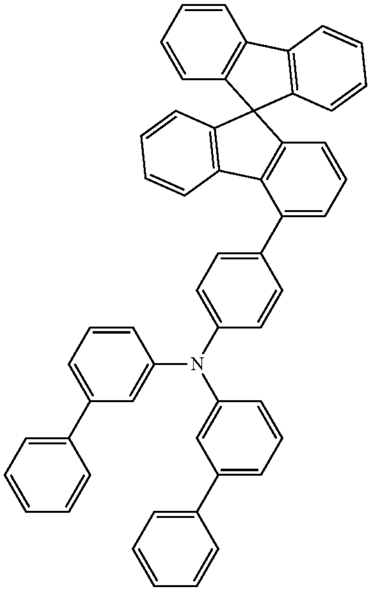
-continued
H11
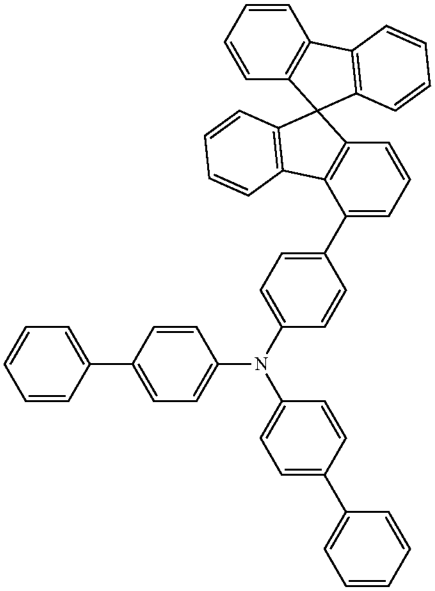
H10
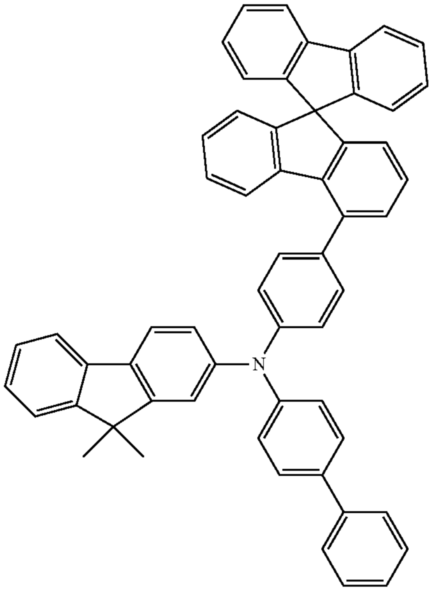
H12
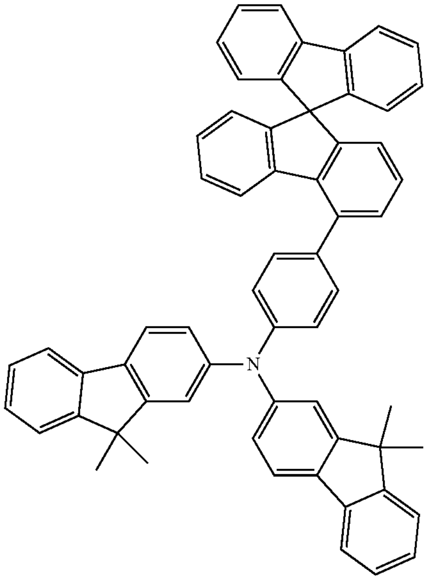

-continued
H13
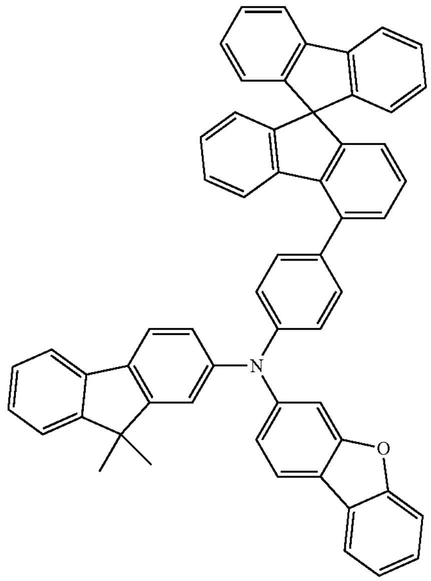
H14
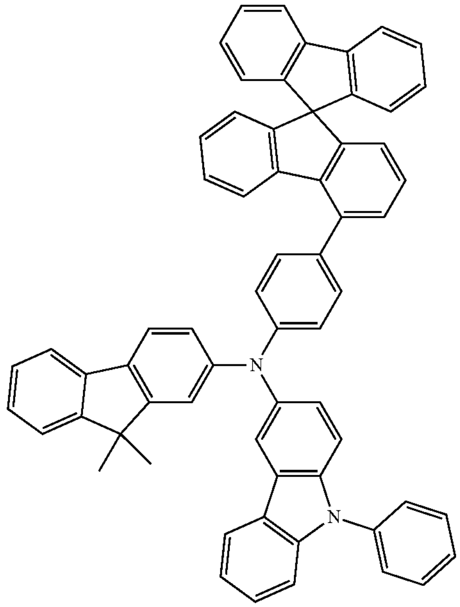
-continued
H15
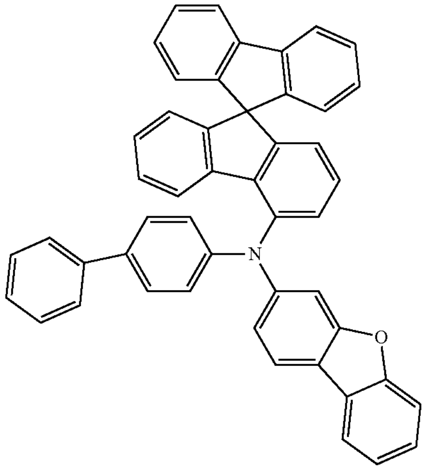
H16
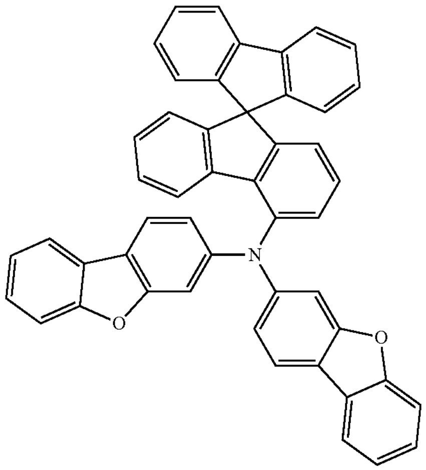
H17
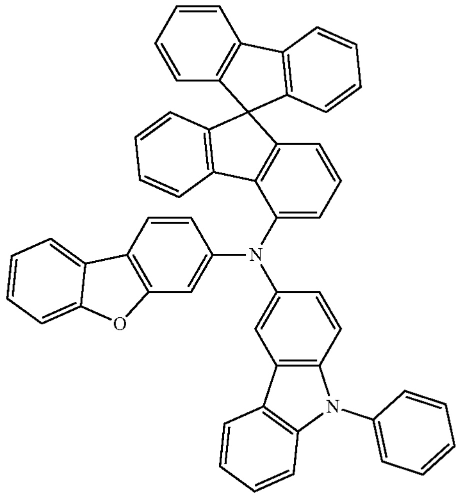

-continued

H18

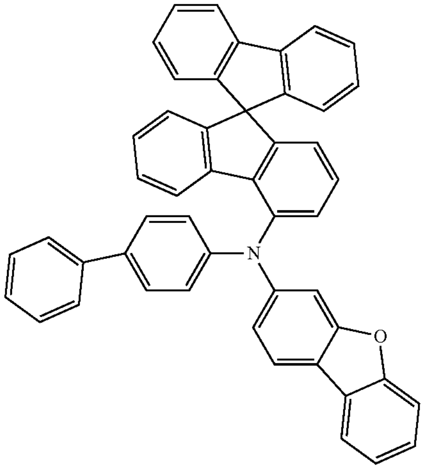

H19

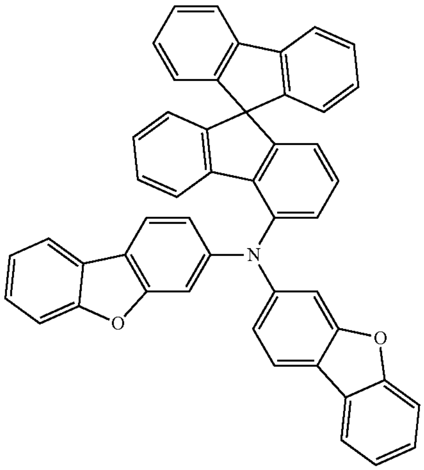

H20

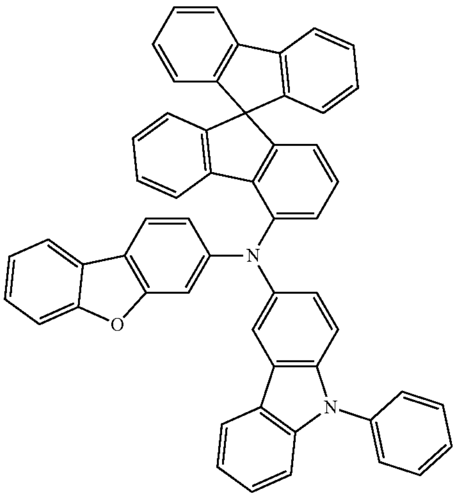

-continued

H21

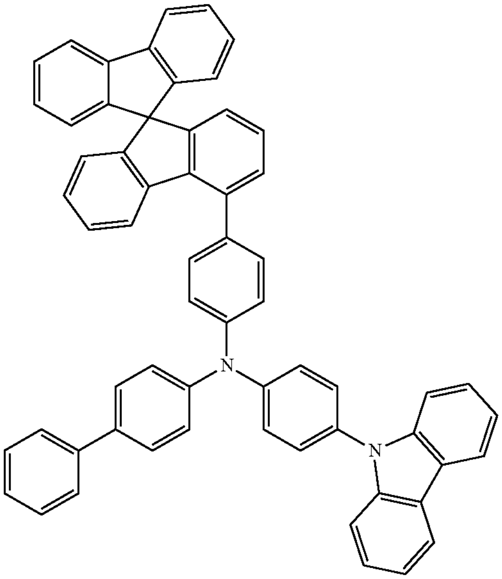

H22

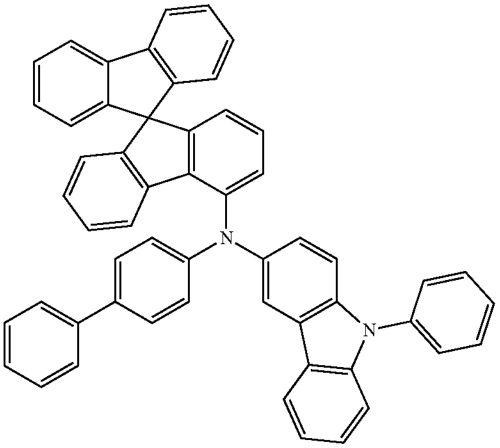

H23

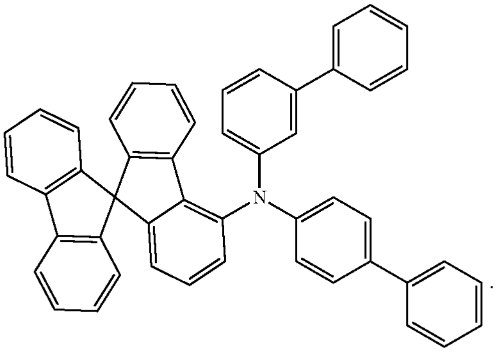

Alternatively, the OLED D1 may further include the HBL 350 which prevents holes from transporting from the EML 340 to the second electrode 220. As an example, the HBL 350 may include a hole blocking material 352 of an azine-based compound having the following structure of Formula 7 and/or a benzimidazole-based compound having the following structure of Formula 9.

[Formula 7]

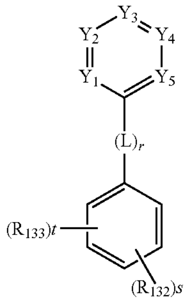

wherein each of $Y_1$ to $Y_5$ is independently $CR_{131}$ or N, one to three of $Y_1$ to $Y_5$ is N, and $R_{131}$ is a $C_6$-$C_{30}$ aryl group; L is a $C_6$-$C_{30}$ arylene group; $R_{132}$ is a $C_6$-$C_{30}$ aryl group or a $C_5$-$C_{30}$ hetero aryl group, wherein the $C_6$-$C_{30}$ aryl group is optionally substituted with another $C_6$-$C_{30}$ aryl or $C_5$-$C_{30}$ hetero aryl or forms a spiro structure with a $C_{10}$-$C_{30}$ fused aryl ring or a $C_{10}$-$C_{30}$ fused hetero aryl ring, wherein the another $C_6$-$C_{30}$ aryl is optionally further substituted with other $C_6$-$C_{30}$ aryl or $C_5$-$C_{30}$ hetero aryl or forms a spiro structure with a $C_{10}$-$C_{30}$ fused aryl ring; $R_{133}$ is hydrogen or adjacent two of $R_{133}$ form a fused aromatic ring; r is 0 or 1; s is 1 or 2; and t is an integer of 0 to 4;

[Formula 9]

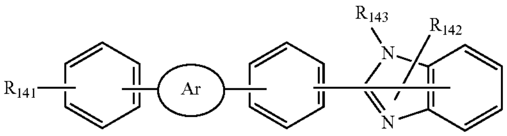

wherein Ar is $C_{10}$-$C_{30}$ arylene; $R_{141}$ is a $C_6$-$C_{30}$ aryl group or a $C_5$-$C_{30}$ hetero aryl group, each of the $C_6$-$C_{30}$ aryl group and the $C_5$-$C_{30}$ hetero aryl group is optionally substituted with $C_1$-$C_{10}$ alkyl; and each of $R_{142}$ and $R_{143}$ is independently hydrogen, a $C_1$-$C_{10}$ alkyl group or a $C_6$-$C_{30}$ aryl group.

In one exemplary embodiment, the aryl group constituting $R_{132}$ in Formula 7 may be unsubstituted or substituted further with another $C_6$-$C_{30}$ aryl group or $C_5$-$C_{30}$ hetero aryl group, or form a spiro structure with other fused aryl ring or fused hetero aryl ring. For example, the aryl or the hetero aryl group that may be substituted to $R_{132}$ may be a $C_{10}$-$C_{30}$ fused aryl group or a $C_{10}$-$C_{30}$ fused hetero aryl group. $R_{133}$ in Formula 7 may be fused to form a naphthyl group. In one exemplary embodiment, the azine-based compound as the hole blocking material 352 may be selected from any azine-based compounds having the following structure of Formula 8:

[Formula 8]

E1

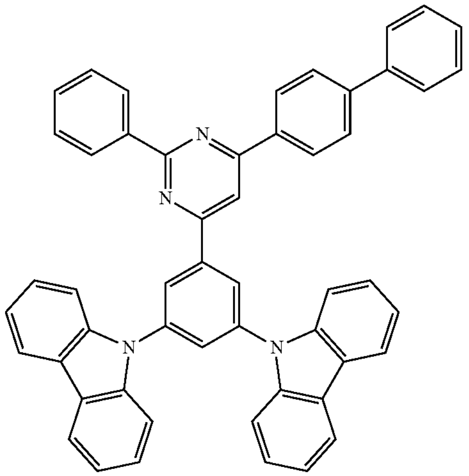

E2

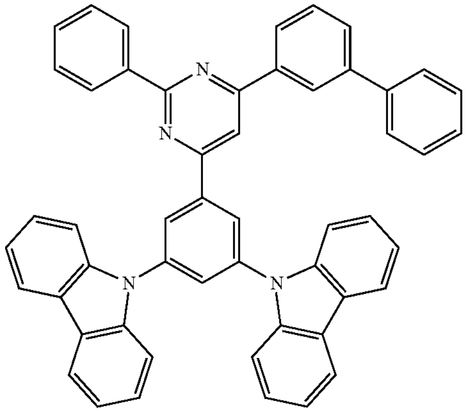

E3

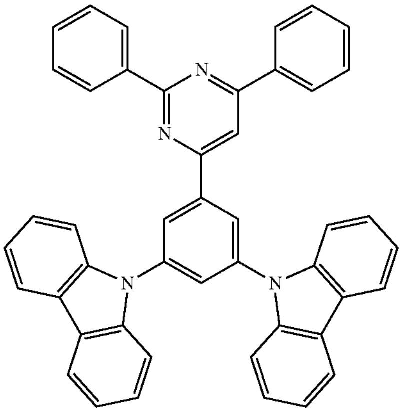

-continued
E4
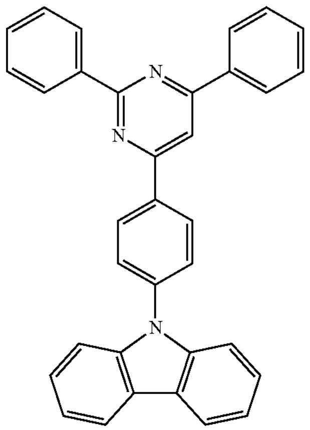
E5
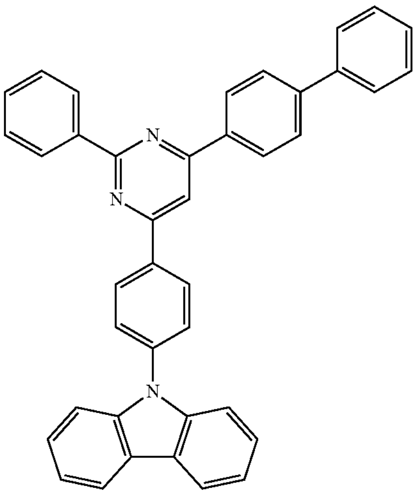
E6
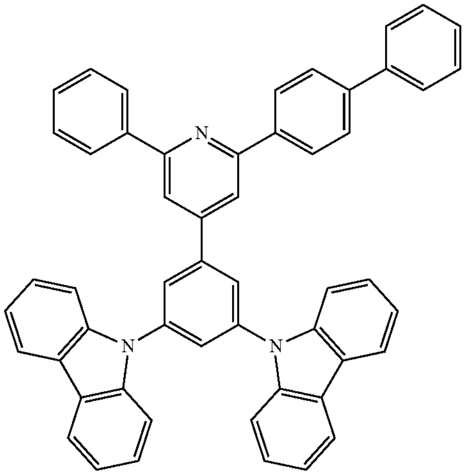
-continued
E7
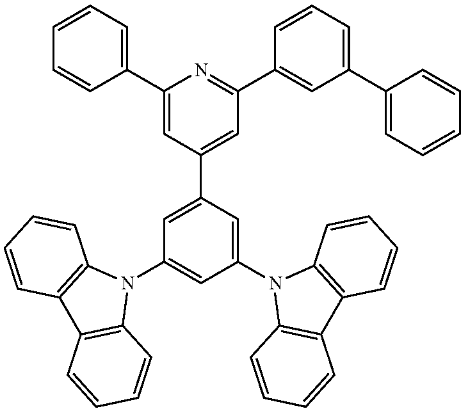
E8
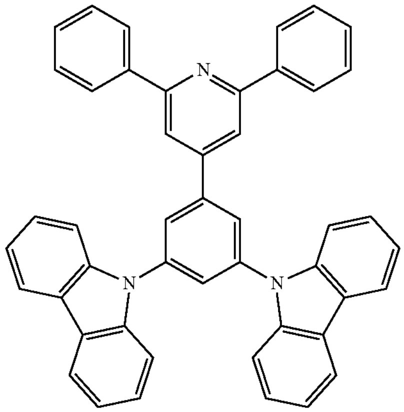
E9
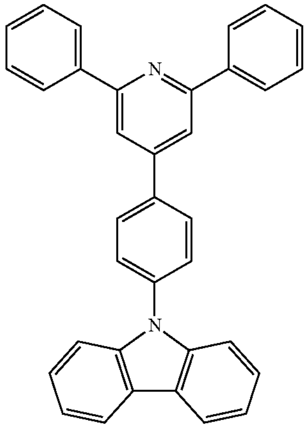

-continued
E10
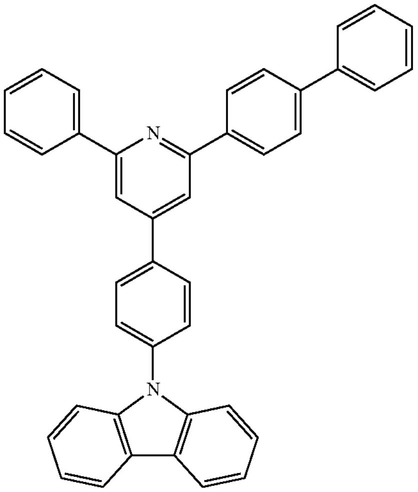
E11
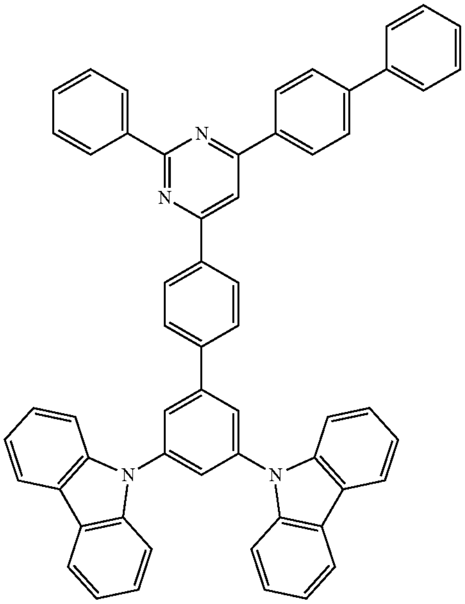
E12
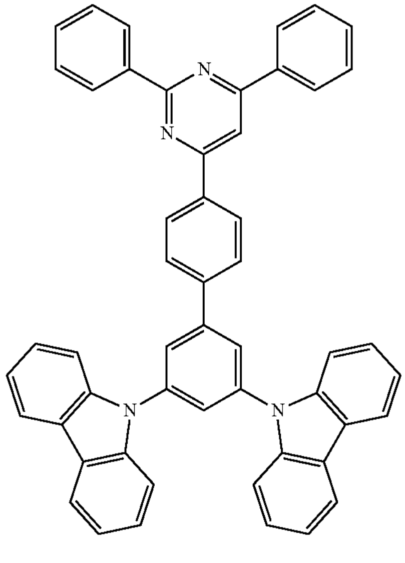
-continued
E13
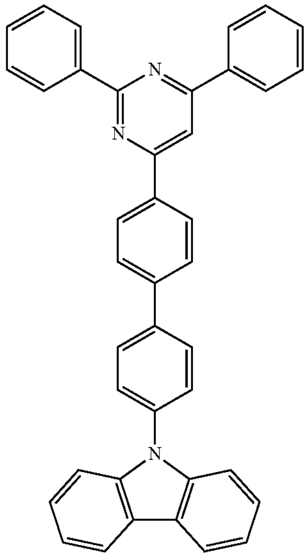
E14
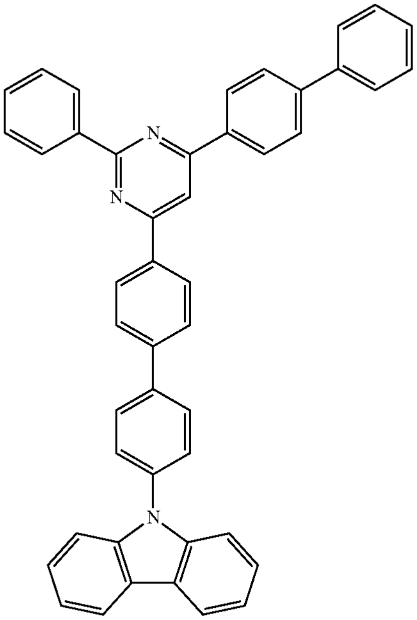
E15
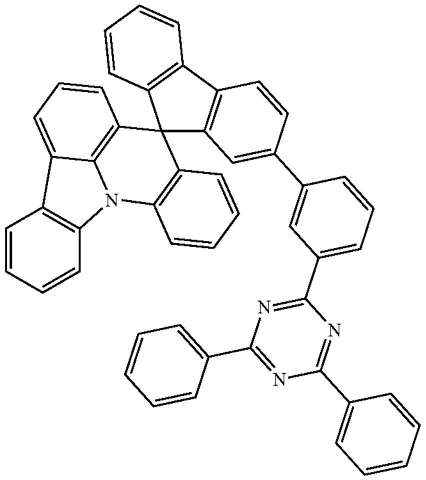

-continued

E16

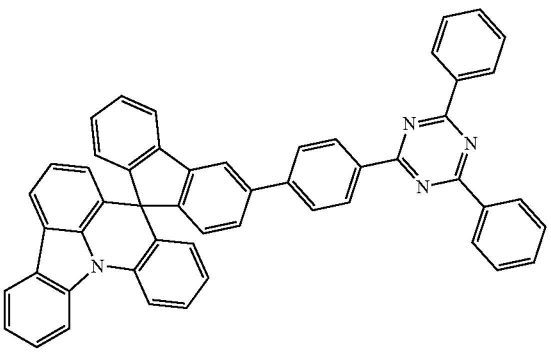

E17

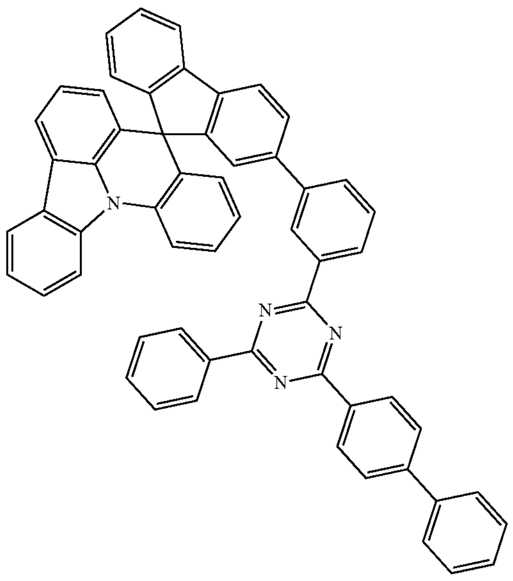

E18

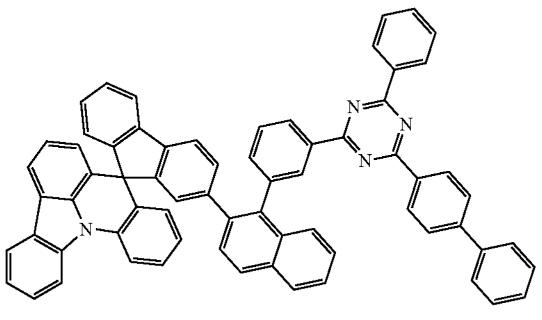

E19

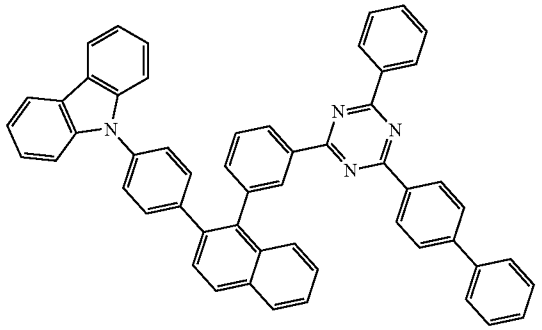

-continued

E20

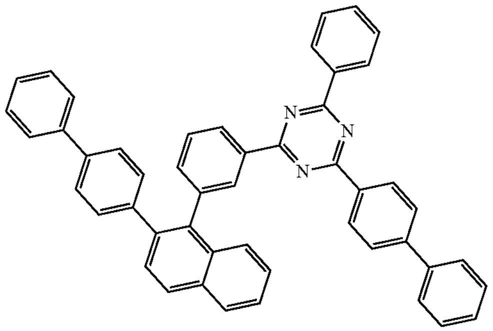

E21

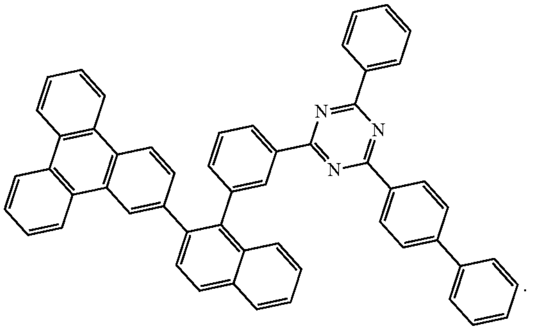

As an example, "Ar" in Formula 9 may be a naphthylene group or an anthracenylene group, $R_{141}$ in Formula 9 may be a phenyl group or a benzimidazole group, $R_{142}$ in Formula 9 may be a methyl group, an ethyl group or a phenyl group and $R_{143}$ in Formula 9 may be hydrogen, a methyl group or a phenyl group. In one exemplary embodiment, the benzimidazole compound as the hole blocking material 352 may be selected from any benzimidazole-based compounds having the following structure of Formula 10.

[Formula 10]

F1

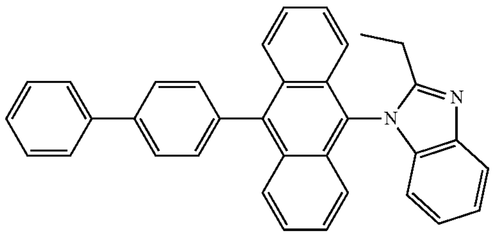

F2

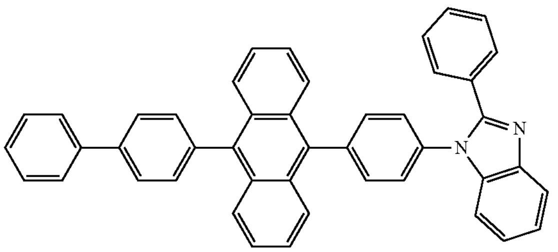

-continued

F3

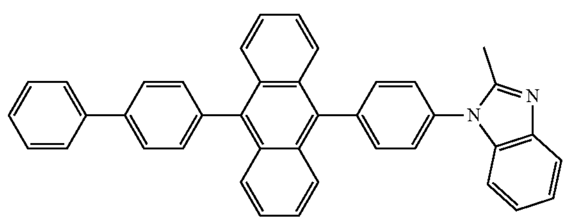

F4

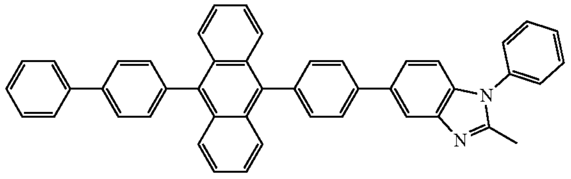

F5

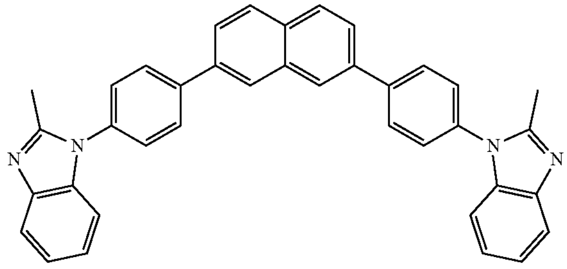

F6

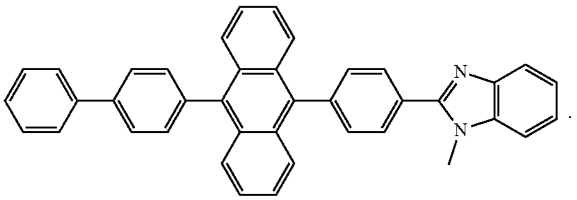

In an exemplary embodiment, each of the EBL 330 and the HBL 350 may independently have a thickness of, but is not limited to, about 5 nm to about 200 nm, for example, about 5 nm to about 100 nm.

The compound having the structure of Formulae 7 to 10 has good electron transport property as well as excellent hole blocking property. Accordingly, the HBL 350 including the compound having the structure of Formulae 7 to 10 may function as a hole blocking layer and an electron transport layer.

In an alternative embodiment, the OLED D1 may further include an ETL disposed between the HBL 350 and the EIL 360. In one exemplary embodiment, the ETL may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

Particularly, the ETL may include an electron transport material selected from, but is not limited to, the group consisting of tris-(8-hydroxyquinoline) aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ), Diphenyl-4-triphenylsilyl-phenylphosphine oxide (TSPO1), 2-[4-(9,10-Di-2-naphthalenyl-2-anthracenyl)phenyl]-1-phenyl-1H-benzimdazole (ZADN), 1,3-bis(9-phenyl-1,10-phenathrolin-2-yl)benzene, 1,4-bis(2-phenyl-1,10-phenanthrolin-4-yl)benzene (p-bPPhenB) and/or 1,3-bis(2-phenyl-1,10-phenanthrolin-4-yl)benzene (m-bPPhenB).

The EIL 360 is disposed between the HBL 350 and the second electrode 220, and can improve physical properties of the second electrode 320 and therefore, can enhance the life span of the OLED D1. In one exemplary embodiment, the EIL 360 may include, but is not limited to, an alkali metal halide or alkaline earth metal halide such as LiF, CsF, NaF, $BaF_2$ and the like, and/or an organic metal compound such as Liq, lithium benzoate, sodium stearate, and the like.

In an alternative embodiment, the EIL 360 may be an organic layer doped with the alkali metal such as Li, Na, K and/or Cs and/or the alkaline earth metal such as Mg, Sr, Ba and/or Ra. An organic host used in the EIL 360 may be the electron transport material and the contents of the alkali metal and/or the alkaline earth metal in the EIL 360 may be, but is not limited to, about 1 wt % to about 30 wt %. For example, the EIL 360 may include an electron transport material having the following structure of Formula 13:

[Formula 13]

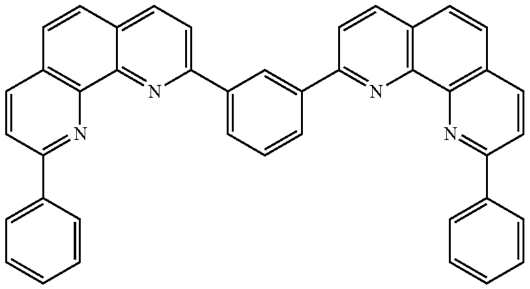

As an example, each of the ETL and the EIL 360 may independently have a thickness of, but is not limited to, about 10 nm to about 200 nm, for example, about 10 nm to 100 nm.

The OLED D1 can maximize its luminous efficiency and luminous lifespan by applying the dopant 342 of the boron-based compound having the structure of Formulae 1A to 2 and the host 344 of the anthracene-based compound having the structure of Formulae 3 to 4 into the EML 340, the aryl amine-based compound having the structure of Formulae 5 and 6 into the EBL 330, and optionally the azine-based compound having the structure of Formulae 7 to 8 and/or the benzimidazole-based compound having the structure of Formulae 9 to 10 into the HBL 350.

In the first exemplary embodiment, the OLED D1 may have single emitting part. An OLED in accordance with the present disclosure may have a tandem structure including multiple emitting parts. FIG. 4 is a schematic cross-sectional view illustrating an organic light emitting diode having two emitting parts in accordance with another exemplary embodiment of the present disclosure.

As illustrated in FIG. 4, the OLED D2 in accordance with the second embodiment of the present disclosure includes first and second electrodes 210 and 220 facing each other and an emissive layer 230A disposed between the first and second electrodes 210 and 220. The emissive layer 230A includes a first emitting part 400 disposed between the first electrode 210 and the second electrode 220, a second emitting part 500 disposed between the first emitting part 400 and the second electrode 220 and a charge generation layer (CGL) 470 disposed between the first and second emitting parts 400 and 500. The organic light emitting display device 100 (FIG. 2) includes the red pixel region, the green pixel region and the blue pixel region, and the OLED D2 may be located in the blue pixel region.

One of the first and second electrodes 210 and 220 may be an anode and the other of the first and second electrodes 210 and 220 may be a cathode. Also, one of the first and second electrodes 210 and 220 may be a transmissive (semi-transmissive) electrode and the other of the first and second electrodes 210 and 220 may be a reflective electrode.

The first emitting part 400 includes a first emitting material layer (EML1) 440 disposed between the first electrode 210 and the CGL 470. The first emitting part 400 may include a first electron blocking layer (EBL1) 430 disposed between the first electrode 210 and the EML1 440, and optionally a first hole blocking layer (HBL1) 450 disposed between the EML1 440 and CGL 470. In addition, the first emitting part 400 may further include an HIL 410 disposed between the first electrode 210 and the EBL1 430 and a first hole transport layer (HTL1) 420 disposed between the HIL 410 and the EBL1 430.

The second emitting part 500 includes a second emitting material layer (EML2) 540 disposed between the CGL 470 and the second electrode 220. The second emitting part 500 may include a second electron blocking layer (EBL2) 530 disposed between the CGL 470 and the EML2 540, and optionally a second hole blocking layer (HBL2) 550 disposed between the EML2 540 and the second electrode 220. In addition, the second emitting part 500 may further include a second hole transport layer (HTL2) 520 disposed between the CGL 470 and EBL2 530 and an EIL 560 disposed between the HBL2 550 and the second electrode 220. Each of the HIL 410, the HTL1 420, the HTL2 520 and the EIL 560 may independently include the same material as described above. The HTL1 420 may include the same material as or different material from the HTL2 520.

The EML1 440 includes a first dopant 442 of a boron-based compound and a first host 444 of an anthracene-based compound so that the EML1 440 emits blue (B) light. The EML2 540 includes a second dopant 542 of a boron-based compound and a second host 544 of an anthracene-based compound so that the EML2 540 emits blue (B) light.

Each of the first dopant 442 and the second dopant 542 of the born-based compound may not be deuterated or partially deuterated, and may have independently the structure of Formulae 1A to 2. Each of the first host 444 and the second host 544 of the anthracene-based compound may be at least partially deuterated, and may have independently the structure of Formulae 3 to 4. The first dopant 442 may be identical to or different from the second dopant 542, and the first host 444 may be identical to or different from the second host 544.

In one exemplary embodiment, each of the contents of the first host 444 and the second host 544 may be independently about 70 wt % to about 99.9 wt % and each of the contents of the first dopant 442 and the second dopant 542 may be independently about 0.1 wt % to about 30 wt % in the EML1 440 and in the EML2 540, respectively. For example, the contents of the first dopant 442 and the second dopant 542 in the EML1 440 and in the EML2 540, respectively, may be about 0.1 wt % to about 10 wt %, for example, about 1 wt % to about 5 wt % so that both the EML1 440 and the EML2 540 can implement sufficient luminous efficiency and luminous lifespan.

Each of the EBL1 430 and the EBL2 530 prevents electrons from transporting from the EML1 440 or EML2 540 to the first electrode 210 or the CGL 470, respectively. Each of the EBL1 430 and the EBL2 530 may include a first electron blocking material 432 and a second electron blocking material 532, respectively. Each of the first electron blocking material 432 and the second electron blocking material 532 may comprise independently the amine-based compound having the structure of Formulae 5 to 6, respectively. The first electron blocking material 432 may be identical to or different from the second electron blocking material 532.

Each of the HBL1 450 and the HBL2 550 prevents holes from transporting from the EML1 440 or EML2 540 to the CGL 470 or the second electrode 220, respectively. Each of the HBL1 450 and the HBL2 550 may include a first hole blocking material 452 and a second hole blocking material 552, respectively. Each of the first hole blocking material 452 and the second hole blocking material 552 may comprise independently the azine-based compound having the structure of Formulae 7 to 8 and/or the benzimidazole-based compound having the structure of Formulae 9 to 10, respectively. The first hole blocking material 452 may be identical to or different from the second hole blocking material 552.

As described above, the compound having the structure of Formulae 7 to 10 has excellent electron transport property as well as excellent hole blocking property. Therefore, each of the HBL1 450 and the HBL2 550 may function as a hole blocking layer and an electron transport layer.

In an alternative embodiment, the first emitting part 400 may further include a first electron transport layer (ETL1) disposed between the HBL1 450 and the CGL 470 and/or the second emitting part 500 may further include a second electron transport layer (ETL2) disposed between the HBL2 550 and the EIL 560.

The CGL 470 is disposed between the first emitting part 400 and the second emitting part 500 so that the first emitting part 400 and the second emitting part 500 are connected via the CGL 470. The CGL 470 may be a PN-junction CGL having an N-type CGL (N-CGL) 480 and a P-type CGL (P-CGL) 490. The N-CGL 480 is disposed between the HBL1 450 and the HTL2 520 and the P-CGL 490 is disposed between the N-CGL 480 and the HTL2 520. The N-CGL 480 injects electrons into the first emitting part 400 and the P-CGL 490 injects holes into the second emitting part 500.

As an example, the N-CGL 480 may be an organic layer doped with an alkali metal such as Li, Na, K and/or Cs and/or an alkaline earth metal such as Mg, Sr, Ba and/or Ra. For example, an organic host used in the N-CGL 480 may include, but is not limited to, an organic compound such as Bphen or MTDATA. The alkali metal and/or the alkaline earth metal may be doped by about 0.01 wt % to about 30 wt % in the N-type CGL 480.

The P-CGL 490 may include, but is not limited to, an inorganic material selected from the group consisting of tungsten oxide ($WO_x$), molybdenum oxide ($MoO_x$), beryllium oxide ($Be_2O_3$), vanadium oxide ($V_2O_5$) and combination thereof, and/or an organic material selected from the group consisting of NPD, HAT-CN, F4TCNQ, TPD, N,N,N',N'-Tetranaphthalenyl-benzidine (TNB), TCTA, N,N'-di-octyl-3,4,9,10-perylenedicarboximide (PTCDI-C8) and combination thereof.

Alternatively, the P-CGL 490 may include a P-type host having the structure of Formula 11 and a P-type dopant having the structure of Formula 12. When the P-CGL 490 includes the P-type host and the P-type dopant, the contents of the P-type dopant in the P-CGL 490 may be, but is not limited to, about 1 wt % to about 50 wt %, for example, about 1 wt % to about 30 wt %.

Each of the EML1 440 and the EML2 540 includes the first and second dopants 442 and 542 of the boron-based compound and the first and second hosts 444 and 544 of the anthracene-based compound where at least one carbon atoms are deuterated, respectively. Each of the first and second dopants 442 and 542 of the boron-based compound may have independently an asymmetric chemical structure such as Formula 1B and may not be deuterated or partially deuterated. Also, each of the first and second hosts 444 and 544 of the anthracene-based compound may have a structure where two naphthyl moieties are linked directly or via the linker to the anthracene moiety and at least one protium, for example, all protiums are deuterated. Accordingly, the OLED D2 and the organic light emitting display device 100 can improve their luminous efficiency and luminous lifespan.

In addition, the OLED D2 and the organic light emitting display device 100 can maximize their luminous efficiency and luminous lifespan by applying the aryl amine-based compound having the structure of Formulae 5 and 6 into the EBL1 430 and the EBL2 530 as the first and second electron blocking materials 432 and 532, respectively, and optionally the azine-based compound having the structure of Formulae 7 to 8 and/or the benzimidazole-based compound having the structure of Formulae 9 to 10 into the HBL1 450 and the HBL2 550 as the first and second hole blocking materials 452 and 552, respectively. In addition, the organic light emitting display device 100 (See, FIG. 2) can implement an image having high color purity by laminating double stack structure of two emitting parts 400 and 500 each of which emits blue color light.

In the second embodiment, the OLED D2 has a tandem structure of two emitting parts. Alternatively, an OLED may include three or more emitting parts, for example, may include a second CGL and a third emitting part disposed on the second emitting parts 500 except the EIL 560 (See, FIG. 7).

Figure 5:
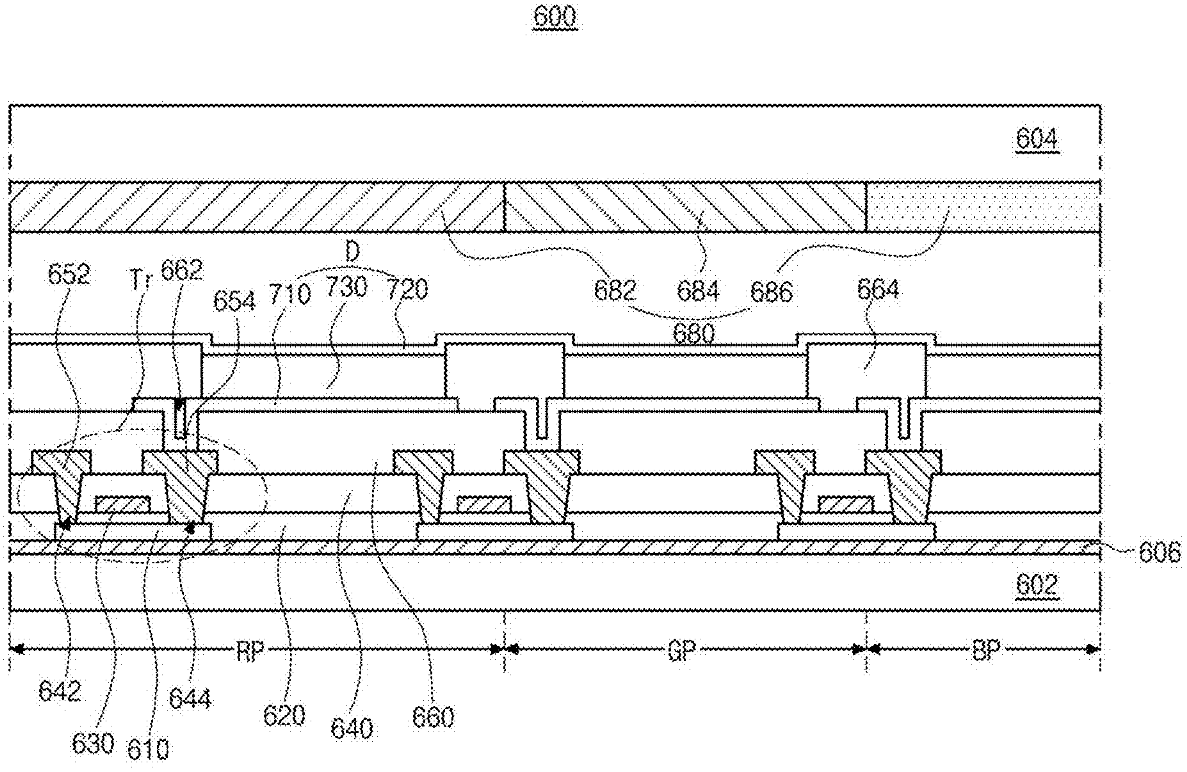
FIG. 5 is a cross-sectional view illustrating an organic light emitting display device in accordance with another exemplary aspect of the present disclosure.

In the above embodiment, the organic light emitting display device 100 and the OLEDs D1 and D2 implement blue (B) emission. Alternatively, an organic light emitting display device and an OLED can implement a full color display device including white (W) emission. FIG. 5 is a schematic cross-sectional view illustrating an organic light emitting display device in accordance with another exemplary embodiment of the present disclosure.

As illustrated in FIG. 5, the organic light emitting display device 600 comprises a first substrate 602 that defines each of a red pixel region RP, a green pixel region GP and a blue pixel region BP, a second substrate 604 facing the first substrate 602, a thin film transistor Tr over the first substrate 602, an organic light emitting diode D disposed between the first and second substrates 602 and 604 and emitting white (W) light and a color filter layer 680 disposed between the organic light emitting diode D and the second substrate 604.

Each of the first and second substrates 602 and 604 may include, but is not limited to, glass, flexible material and/or polymer plastics. For example, each of the first and second substrates 602 and 604 may be made of PI, PES, PEN, PET, PC and combination thereof. The first substrate 602, over which a thin film transistor Tr and an organic light emitting diode D are arranged, forms an array substrate.

A buffer layer 606 may be disposed over the first substrate 602, and the thin film transistor Tr is disposed over the buffer layer 606 correspondingly to each of the red pixel region RP, the green pixel region GP and the blue pixel region BP. The buffer layer 606 may be omitted.

A semiconductor layer 610 is disposed over the buffer layer 606. The semiconductor layer 610 may be made of oxide semiconductor material or polycrystalline silicon.

A gate insulating layer 620 including an insulating material, for example, inorganic insulating material such as silicon oxide ($SiO_x$) or silicon nitride ($SiN_x$) is disposed on the semiconductor layer 610.

A gate electrode 630 made of a conductive material such as a metal is disposed over the gate insulating layer 620 so as to correspond to a center of the semiconductor layer 610. An interlayer insulting layer 640 including an insulating material, for example, inorganic insulating material such as silicon oxide ($SiO_x$) or silicon nitride ($SiN_x$), or an organic insulating material such as benzocyclobutene or photo-acryl, is disposed on the gate electrode 630.

The interlayer insulating layer 640 has first and second semiconductor layer contact holes 642 and 644 that expose both sides of the semiconductor layer 610. The first and second semiconductor layer contact holes 642 and 644 are disposed over opposite sides of the gate electrode 630 with spacing apart from the gate electrode 630.

A source electrode 652 and a drain electrode 654, which are made of a conductive material such as a metal, are disposed on the interlayer insulating layer 640. The source electrode 652 and the drain electrode 654 are spaced apart from each other with respect to the gate electrode 630, and contact both sides of the semiconductor layer 610 through the first and second semiconductor layer contact holes 642 and 644, respectively.

The semiconductor layer 610, the gate electrode 630, the source electrode 652 and the drain electrode 654 constitute the thin film transistor Tr, which acts as a driving element.

Although not shown in FIG. 5, a gate line and a data line, which cross each other to define a pixel region, and a switching element, which is connected to the gate line and the data line, may be further formed in the pixel region. The switching element is connected to the thin film transistor Tr, which is a driving element. In addition, a power line is spaced apart in parallel from the gate line or the data line, and the thin film transistor Tr may further include a storage capacitor configured to constantly keep a voltage of the gate electrode for one frame.

A passivation layer 660 is disposed on the source and drain electrodes 652 and 654 with covering the thin film transistor Tr over the whole first substrate 602. The passivation layer 660 has a drain contact hole 662 that exposes the drain electrode 654 of the thin film transistor Tr.

The organic light emitting diode (OLED) D is located over the passivation layer 660. The OLED D includes a first electrode 710 that is connected to the drain electrode 654 of the thin film transistor Tr, a second electrode 720 facing from the first electrode 710 and an emissive layer 730 disposed between the first and second electrodes 710 and 720.

The first electrode 710 formed for each pixel region may be an anode and may include a conductive material having relatively high work function value, for example, TCO. As an example, the first electrode 710 may include, ITO, IZO, ITZO, SnO, ZnO, ICO, AZO, and the like.

When the organic light emitting display device 600 is a bottom-emission type, the first electrode 710 may have a single-layered structure of TCO. Alternatively, when the organic light emitting display device 600 is a top-emission type, a reflective electrode or a reflective layer may be disposed under the first electrode 710. For example, the reflective electrode or the reflective layer may include, but is not limited to, Ag or APC alloy. In the organic light emitting display device 600 of the top-emission type, the first electrode 710 may have a triple-layered structure of ITO/Ag/ITO or ITO/APC/ITO.

A bank layer 664 is disposed on the passivation layer 660 in order to cover edges of the first electrode 710. The bank layer 664 exposes a center of the first electrode 710 corresponding to each of the red pixel region RP, the green pixel region GP and the blue pixel region BP. The bank layer 664 may be omitted.

An emissive layer 730 including multiple emitting parts is disposed on the first electrode 710. Since the OLED D emits white light in each of the red, green and blue pixel regions RP, GP and BP, the emissive layer 730 may be formed of a common layer without separating in the red, green and blue pixel regions RP, GP and BP.

Figure 6:
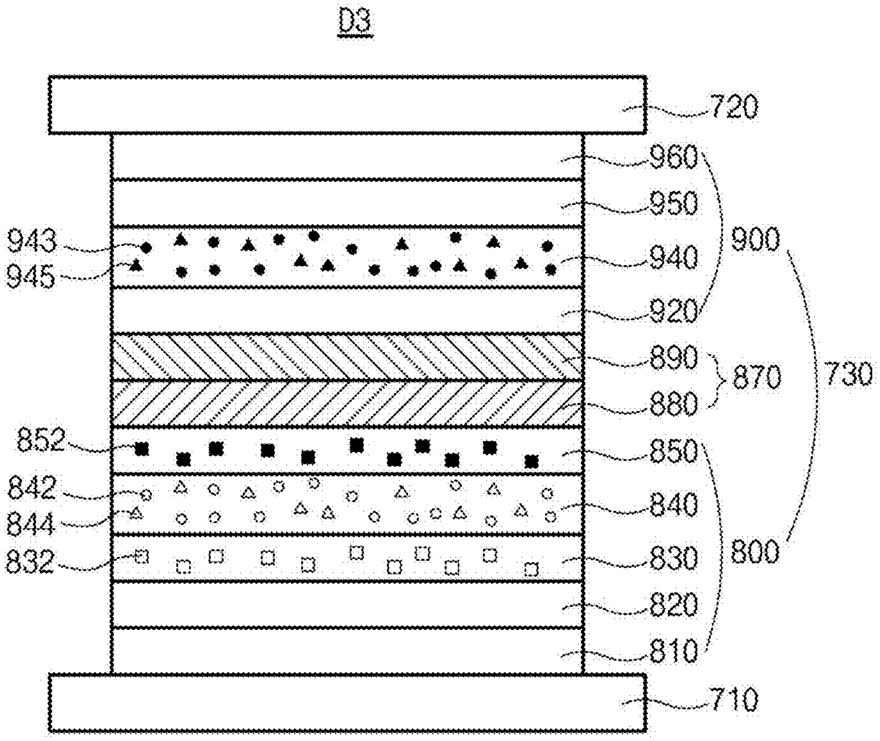
FIG. 6 is a cross-sectional view illustrating an organic light emitting diode having a double stack structure in accordance with still another exemplary aspect of the present disclosure.
Figure 7:
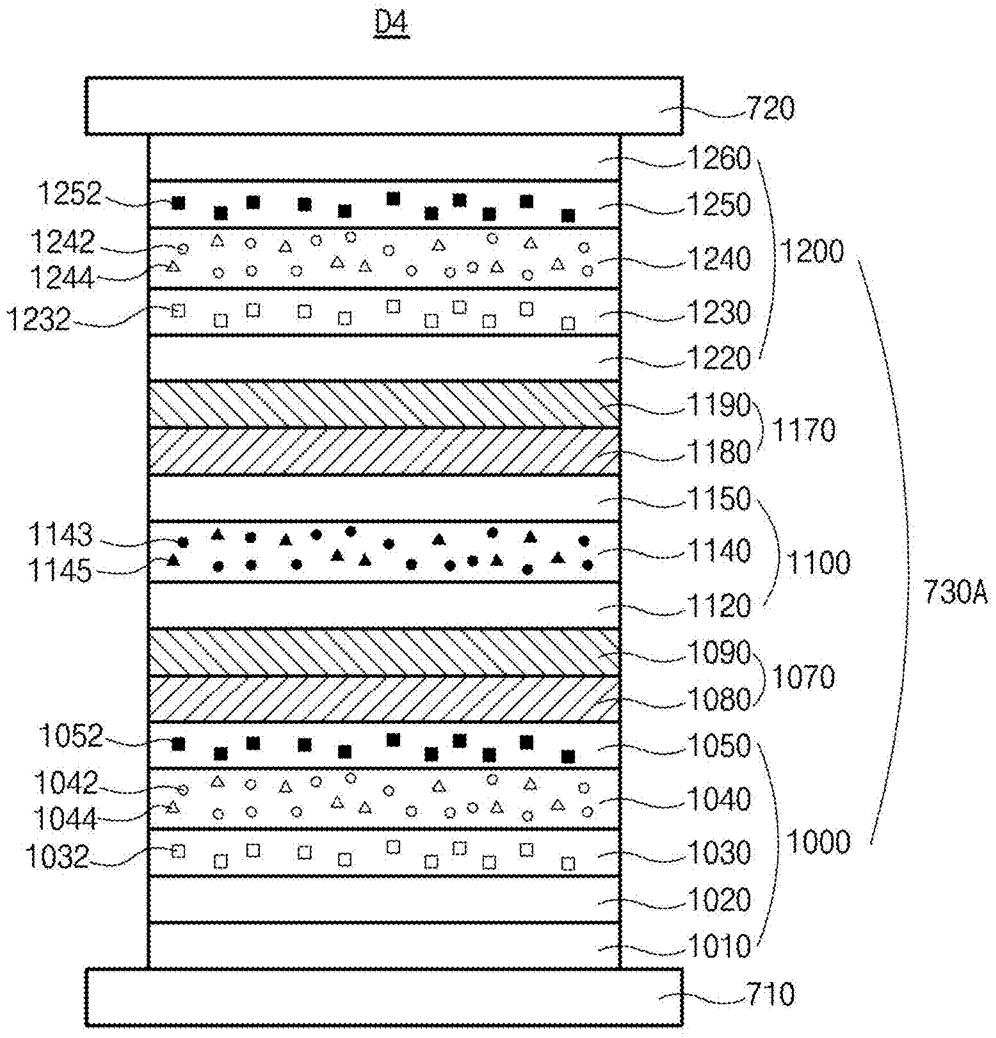
FIG. 7 is a cross-sectional view illustrating an organic light emitting diode having a triple stack structure in accordance with still further another exemplary aspect of the present disclosure.

As illustrated in FIGS. 6 and 7, the emissive layer 730 may include multiple emitting parts 800, 900, 1000, 1100 and 1200 and at least one charge generation layer 870, 1070 and 1170. Each of the emitting parts 800, 900, 1000, 1100 and 1200 may include EML and may further include at least one of HIL, HTL, EBL, HBL, ETL and/or EIL.

The second electrode 720 is disposed over the first substrate 602 above which the emissive layer 730 is disposed. The second electrode 720 may be disposed over a whole display area, and may include a conductive material with a relatively low work function value compared to the first electrode 710, and may be a cathode. For example, the second electrode 720 may include, but is not limited to, Al, Mg, Ca, Ag, alloy thereof and combination thereof such as Al—Mg.

Since the light emitted from the emissive layer 730 is incident to the color filter layer 680 through the second electrode 720 in the organic light emitting display device 600 in accordance with the second embodiment of the present disclosure, the second electrode 720 has a thin thickness so that the light can be transmitted.

The color filter layer 680 is disposed over the OLED D and includes a red color filter 682, a green color filter 684 and a blue color filter 686 each of which is disposed correspondingly to the red pixel region RP, the green pixel region GP and the blue pixel region BP, respectively. Although not shown in FIG. 5, the color filter layer 680 may be attached to the OLED through an adhesive layer. Alternatively, the color filter layer 680 may be disposed directly on the OLED D.

In addition, an encapsulation film may be disposed over the second electrode 720 in order to prevent outer moisture from penetrating into the OLED D. The encapsulation film may have, but is not limited to, a laminated structure of a first inorganic insulating film, an organic insulating film and a second inorganic insulating film (See, 170 in FIG. 2). In addition, the organic light emitting display device 600 may further include a polarizing plate.to reduce reflection of external light. For example, the polarizing plate may be a circular polarizing plate. When the organic light emitting display device 600 is a bottom-emission type, the polarizing plate may be located under the first substrate 602. Alternatively, when the organic light emitting display device 600 is a top emission type, the polarizing plate may be located over the second substrate 604.

In FIG. 5, the light emitted from the OLED D is transmitted through the second electrode 720 and the color filter layer 680 is disposed over the OLED D. Alternatively, the light emitted from the OLED D is transmitted through the first electrode 710 and the color filter layer 680 may be disposed between the OLED D and the first substrate 602. In addition, a color conversion layer may be formed between the OLED D and the color filter layer 680. The color conversion layer may include a red color conversion layer, a green color conversion layer and a blue color conversion layer each of which is disposed correspondingly to each pixel region (RP, GP and BP), respectively, so as to covert the white (W) color light to each of a red, green and blue color lights, respectively.

As described above, the white (W) color light emitted from the OLED D is transmitted through the red color filter 682, the green color filter 684 and the blue color filter 686 each of which is disposed correspondingly to the red pixel region RP, the green pixel region GP and the blue pixel region BP, respectively, so that red, green and blue color lights are displayed in the red pixel region RP, the green pixel region GP and the blue pixel region BP.

FIG. 6 is a schematic cross-sectional view illustrating an organic light emitting diode having a tandem structure of two emitting parts. As illustrated in FIG. 6, the organic light emitting diode (OLED) D3 in accordance with the exemplary embodiment includes first and second electrodes 710 and 720 and an emissive layer 730 disposed between the first and second electrodes 710 and 720. The emissive layer 730 includes a first emitting part 800 disposed between the first and second electrodes 710 and 720, a second emitting part 900 disposed between the first emitting part 800 and the second electrode 720 and a charge generation layer (CGL) 870 disposed between the first and second emitting parts 800 and 900.

One of the first and second electrodes 710 and 720 may be an anode and the other of the first and second electrodes 710 and 720 may be a cathode. Also, one of the first and second electrodes 710 and 720 may be a transmissive (semi-transmissive) electrode and the other of the first and second electrodes 710 and 720 may be a reflective electrode.

In addition, one of the first and second emitting parts 800 and 900 emit blue (B) light and the other of the first and second emitting parts 800 and 900 emits red-green (RG) or yellow-green (YG) light. Hereinafter, the OLED D3 where the first emitting part 800 emits blue (B) light and the second emitting part 900 emits red-green (RG) and/or yellow-green (YG) light will be described in detail.

The first emitting part 800 includes an EML1 840 disposed between the first electrode 710 and the CGL 870. The first emitting part 800 may include an EBL1 830 disposed between the first electrode 710 and the EML1 840, and optionally an HBL1 850 disposed between the EML1 840 and the CGL 870. In addition, the first emitting part 800 may further include an HIL 810 disposed between the first electrode and the EBL1 830 and an HTL1 820 disposed between the HIL 810 and the EBL1 830. Alternatively, the first emitting part 800 may further include an ETL1 disposed between the HBL1 850 and the CGL 870.

The second emitting part 900 includes an EML2 940 disposed between the CGL 870 and the second electrode 720. The second emitting part 900 may include an HTL 920 disposed between the CGL 870 and the EML2 940 and an ETL2 950 disposed between the second electrode 720 and the EML2 940 and an EIL 960 disposed between the second electrode 720 and the ETL2 950. Alternatively, the second emitting part 900 may further include an EBL2 disposed between the HTL2 920 and the EML2 940 and/or an HBL2 disposed between the EML2 940 and the ETL2 950.

The CGL 870 is disposed between the first emitting part 800 and the second emitting part 900. The CGL 870 may be a PN-junction CGL having an N-CGL 870 and a P-CGL 890. The N-CGL 880 is disposed between the HBL1 850 and the HTL2 920 and the P-CGL 890 is disposed between the N-CGL 880 and the HTL2 920.

Each of the HIL 810, the HTL1 820, the HTL2 920, the EIL 560 and the CGL 870 may independently include the same material as described above. The HTL1 820 may include the same material as or different material from the HTL2 920.

The EML1 840 includes a first dopant 842 of a boron-based compound and a first host 844 of an anthracene-based compound so that the EML1 840 emits blue (B) light. The first dopant 842 of the born-based compound may not be deuterated or partially deuterated, and may have the structure of Formulae 1A to 2. The first host 844 of the anthracene-based compound may be at least partially deuterated, and may have the structure of Formulae 3 to 4.

In one exemplary embodiment, the contents of the first host 844 may be about 70 wt % to about 99.9 wt % and the contents of the first dopant 842 may be about 0.1 wt % to about 30 wt % in the EML1 840. For example, the contents of the first dopant 844 in the EML1 840 may be about 0.1 wt % to about 10 wt %, for example, about 1 wt % to about 5 wt % so that the EML1 840 can implement sufficient luminous efficiency and luminous lifespan.

The EBL1 830 prevents electrons from transporting from the EML1 840 to the first electrode 710 and may include an electron blocking material 832. The electron blocking material 832 may include the amine-based compound having the structure of Formulae 5 to 6.

The HBL1 850 prevent holes from transporting form the EML1 840 to the CGL 870 and may include a hole blocking material 852. The hole blocking material 852 may include the azine-based compound having the structure of Formulae 7 to 8 and/or the benzimidazole-based compound having the structure of Formulae 9 to 10. As described above, the compound having the structure of Formulae 7 to 10 has excellent electron transport property as well as excellent hole blocking property. Therefore, the HBL1 850 may function as a hole blocking layer and an electron transport layer.

In one exemplary aspect, the EML2 940 may emit yellow-green (YG) light. For example, the EML2 940 may include yellow-green (YG) dopant 943 and a host 945.

The host 945 in the EML2 940 may include, but is not limited to, 9,9'-Diphenyl-9H,9'H-3,3'-bicarbazole (BCzPh), CBP, 1,3,5-Tris(carbazole-9-yl)benzene (TCP), TCTA, 4,4'-Bis(carbazole-9-yl)-2,2'-dimethylbipheyl (CDBP), 2,7-Bis (carbazole-9-yl)-9,9-dimethylfluorene (DMFL-CBP), 2,2',7,7'-Tetrakis(carbazole-9-yl)-9,9-spirofluorene (Spiro-CBP), Bis[2-(diphenylphosphine)phenyl] ether oxide (DPEPO), 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-Bis(carbazole-9-yl)-9-(2-ethyl-hexyl)-9H-carbazole (TCz1), Bis(2-hydroxylphenyl)-pyridine)beryllium (Bepp2), Bis(10-hydroxylbenzo[h] quinolinato)beryllium (Bebg2) and/or 1,3,5-Tris(1-pyrenyl)benzene (TPB3).

The yellow-green (YG) dopant 943 may include at least one of yellow-green (YG) fluorescent material, yellow-green (YG) phosphorescent material and yellow-green (YG) delayed fluorescent material. As an example, the yellow-green (YG) dopant 943 may include, but is not limited to, 5,6,11,12-Tetraphenylnaphthalene (Rubrene), 2,8-Di-tert-butyl-5,11-bis(4-tert-butylphenyl)-6,12-diphenyltetracene (TBRb), Bis(2-phenylbenzothiazolato)(acetylacetonate) iridium(III) ($Ir(BT)_2(acac)$), Bis(2-(9,9-diethytl-fluoren-2-yl)-1-phenyl-1H-benzo[d]imdiazolato)(acetylacetonate) iridium(III) ($Ir(fbi)_2(acac)$), Bis(2-phenylpyridine)(3-(pyridine-2-yl)-2H-chromen-2-onate)iridium(III) (fac-$Ir(ppy)_2Pc$), Bis(2-(2,4-difluorophenyl)quinoline)(picolinate) iridium(III) (FPQIrpic), and the like.

Alternatively, the EML2 940 may emit red-green (RG) light. In this case, the EML2 940 may include green (G) and red (R) dopant 943 and a host 945. In this case, the EML2 940 may have a single-layered structure including the host, green (G) dopant and red (R) dopant, or may have a double-layered structure comprising a lower layer (first layer) including a host and green (G) dopant (or red (R) dopant) and an upper layer (second layer) including a host and red (R) dopant (or green (G) dopant).

The host 945 in the EML2 940 emitting red-green (RG) light may be the same as the host emitting yellow-green (YG) light.

The green (G) dopant 943 in the EML2 940 may include at least one of green fluorescent material, green phosphorescent material and green delayed fluorescent material. As an example, the green (G) dopant 943 may include, but is not limited to, [Bis(2-phenylpyridine)](pyridyl-2-benzofuro[2,3-b]pyridine)iridium, fac-Tris(2-phenylpyridine)iridium (III) (fac-$Ir(ppy)_3$), Bis(2-phenylpyridine)(acetylacetonate) iridium(III) ($Ir(ppy)_2(acac)$), Tris[2-(p-tolyl)pyridine] iridium(III) ($Ir(mppy)_3$), Bis(2-(naphthalene-2-yl)pyridine) (acetylacetonate)iridium(III) ($Ir(npy)_2acac$), Tris(2-phenyl-3-methyl-pyridine)iridium ($Ir(3mppy)_3$), fac-Tris(2-(3-p-xylyl)phenyl)pyridine iridium(III) (TEG), and the like The red (R) dopant 943 in the EML2 940 may include at least one of red fluorescent material, red phosphorescent material and red delayed fluorescent material. As an example, the red (R) dopant 943 may include, but is not limited to, [Bis(2-(4,6-dimethyl)phenylquinoline)](2,2,6,6-tetramethylheptane-3,5-dionate)iridium(III), Bis[2-(4-n-hexylphenyl)quinoline](acetylacetonate)iridium(III) (Hex-$Ir(phq)_2(acac)$), Tris[2-(4-n-hexylphenyl)quinoline]iridium (III) (Hex-$Ir(phq)_3$), Tris[2-phenyl-4-methylquinoline] iridium(III) ($Ir(Mphq)_3$), Bis(2-phenylquinoline)(2,2,6,6-tetramethylheptene-3,5-dionate)iridium(III) ($Ir(dpm)PQ_2$), Bis(phenylisoquinoline)(2,2,6,6-tetramethylheptene-3,5-dionate)iridium(III) ($Ir(dpm)(piq)_2$), Bis[(4-n-hexylphenyl) isoquinoline](acetylacetonate)iridium(III) (Hex-$Ir(piq)_2(acac)$), Tris[2-(4-n-hexylphenyl)quinoline]iridium(III) (Hex-$Ir(piq)_3$), Tris(2-(3-methylphenyl)-7-methyl-quinolato)iridium ($Ir(dmpq)_3$), Bis[2-(2-methylphenyl)-7-methyl-quinoline](acetylacetonate)iridium(III) ($Ir(dmpq)_2(acac)$), Bis[2-(3,5-dimethylphenyl)-4-methyl-quinoline](acetylacetonate)iridium(III) ($Ir(mphmq)_2(acac)$), and the like.

In an alternative aspect, the EML2 940 may have a triple-layered structure of a first layer including a host and red (R) dopant, a second layer including a host and yellow-green (YG) dopant and a third layer including a host and green (G) dopant.

When the EML2 940 emits red-green (RG) or yellow-green (YG) light, the contents of the host 945 may be about 70 wt % to about 99.9 wt % and the contents of the dopant 943 may be about 0.01 wt % to about 30 wt %, respectively, in the EML2 940. For example, the contents of the dopant 943 in the EML2 940 may be about 0.1 wt % to about 10 wt %, for example, about 1 wt % to about 5 wt % so that the EML2 940 can implement sufficient luminous efficiency and luminous lifespan.

Each of the ETL1 and the ETL2 950 may include independently oxadiazole-based compounds, triazole-based compounds, phenanthroline-based compounds, benzoxazole-based compounds, benzothiazole-based compounds, benzimidazole-based compounds, triazine-based compounds, and the like. For example, each of the ETL1 and the ETL2 950 may include independently electron transport material selected from, but is not limited to, $Alq_3$, PBD, spiro-PBD, Liq, TPBi, BAlq, Bphen, NBphen, BCP, TAZ, NTAZ, TpPyPB, TmPPPyTz, PFNBr, TPQ, TSPO1, ZADN, 1,3-bis(9-phenyl-1,10-phenathrolin-2-yl)benzene, p-bPPhenB, m-bPPhenB and combination thereof.

The EBL2, which may be disposed between the HTL2 920 and the EML2 940, may include a second electron blocking material. As an example, the second electron blocking material may include the amine-based compound having the structure of Formulae 5 to 6.

Alternatively, the EBL2 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl)benzene (mCP), 3,3-di(9H-carbazol-9-yl)biphenyl (mCBP), CuPc, DNTPD, TDAPB, DCDPA, 2,8-bis(9-phenyl-9H-carbazol-3-yl)dibenzo[b,d]thiophene, 3,6-bis(N-carbazolyl)-N-phenyl-carbazole and combination thereof.

The HBL2, which may be disposed between the EML2 940 and the ETL2 960, may include a second hole blocking material. As an example, the second hole blocking material may include the azine-based compound having the structure of Formulae 7 to 8 and/or the benzimidazole-based compound having the structure of Formulae 9 to 10. Alternatively, the HBL2 may include oxadiazole-based compounds, triazole-based compounds, phenanthroline-based compounds, benzoxazole-based compounds, benzothiazole-based compounds, benzimidazole-based compounds, triazine-based compounds, and the like, which can be used as the electron transport material in the ETL2 950.

In the OLED D3, the EML1 840 includes the dopant 842 of the boron-based compound and the host 844 of the anthracene-based compound in which at least one protium is substituted with deuterium, and the EML2 940 emits red-green (RG) and/or yellow-green (YG) light. Alternatively, the EML1 840 may emit red-green (RG) and/or yellow green light and the EML2 940 may include the dopant 842 of the boron-based compound and the host 844 of the anthracene-based compound to emit blue (B) light.

In the OLED D3, the EML1 840 includes the dopant 842 of the boron-based compound and the host 844 of the anthracene-based compound which is at least partially deuterated. The dopant 842 of the boron-based compound may have an asymmetric chemical structure such as Formula 1B and may not be deuterated or partially deuterated. Also, the host 844 of the anthracene-based compound may have a structure where two naphthyl moieties are linked directly or via the linker to the anthracene moiety and at least one protium, for example, all protiums are deuterated. Accordingly, the OLED D3 and the organic light emitting display device 600 can improve their luminous efficiency and luminous lifespan.

In addition, the OLED D3 and the organic light emitting display device 600 can maximize their luminous efficiency and luminous lifespan by applying the aryl amine-based compound having the structure of Formulae 5 and 6 into the EBL1 830 as the first electron blocking materials 832, and optionally the azine-based compound having the structure of Formulae 7 to 8 and/or the benzimidazole-based compound having the structure of Formulae 9 to 10 into the HBL1 850 as the first hole blocking layers 852.

Alternatively, an organic light emitting diode may have three or more emitting parts. FIG. 7 is a schematic cross-sectional view illustrating an organic light emitting diode in accordance with still another exemplary aspect of the present disclosure. As illustrated in FIG. 7, the organic light emitting diode (OLED) D4 includes first and second electrodes 710 and 720 facing each other and an emissive layer 730A disposed between the first and second electrodes 710 and 720. The emissive layer 730A includes a first emitting part 1000 disposed between the first and second electrodes 710 and 720, a second emitting part 1100 disposed between the first emitting part 1000 and the second electrode 720, a third emitting part 1200 disposed between the second emitting part 1100 and the second electrode 720, a first charge generation layer (CGL1) 1070 disposed between the first and second emitting parts 1000 and 1100, and a second charge generation layer (CGL2) 1170 disposed between the second and third emitting parts 1100 and 1200.

At least one of the first to third emitting parts 1000, 1100 and 1200 may emit blue (B) light and at least another of the first to third emitting parts 1000, 1100 and 1200 may emit red green (RG) or yellow green (YG) light. Hereinafter, the OLED D4, where the first and third emitting parts 1000 and 1200 emit blue (B) light and the second emitting part 1100 emits red green (RG) and/or yellow green (YG) light, will be explained in detail.

The first emitting part 1000 includes an EML1 1040 disposed between the first electrode 710 and the CGL1 1070. The first emitting part 1000 may include an EBL1 1030 disposed between the first electrode 710 and the EML1 1040, and optionally an HBL1 1050 disposed between the EML1 1040 and the CGL1 1070. In addition, the first emitting part 1000 may further include an HIL 1010 disposed between the first electrode 710 and the EBL1 1030, an HTL1 1020 disposed between the HIL 1010 and the EBL1 1030, and optionally a first electron transport layer (ETL1) disposed between the HBL1 1050 and the CGL1 1070.

The second emitting part 1100 includes an EML2 1140 disposed between the CGL1 1070 and the CGL2 1170. The second emitting part 1100 may include an HTL2 1120 disposed between the CGL1 1070 and the EML2 1140 and an ETL2 1150 disposed between the EML2 1140 and the CGL2 1170. In addition, the second emitting part 1100 may further include an EBL2 disposed between the HTL2 1120 and the EML2 1140 and/or an HBL2 disposed between the EML2 1140 and the ETL2 1150.

The third emitting part 1200 includes a third emitting material layer (EML3) 1240 disposed between the CGL2 1170 and the second electrode 720. The third emitting part 1200 may include a third electron blocking layer (EBL3) 1230 disposed between the CGL2 1170 and the EML3 1240, and optionally a third hole blocking layer (HBL3) 1250 disposed between the EML3 1240 and the second electrode 720. In addition, the third emitting part 1200 may further include a third hole transport layer (HTL3) 1220 disposed between the CGL2 1170 and the EBL3 1230, an EIL 1260 disposed between the HBL3 1250 and the second electrode 720, and optionally a third electron transport layer (ETL3) disposed between the HBL3 1250 and the EIL 1260.

The CGL1 1070 is disposed between the first emitting part 1000 and the second emitting part 1100. The CGL1 1070 may be a PN-junction CGL having a first N-type CGL (N-CGL1) 1080 and a first P-type CGL (P-CGL1) 1090. The N-CGL1 1080 is disposed between the HBL1 1050 and the HTL2 1120 and the P-CGL1 1090 is disposed between the N-CGL1 1080 and the HTL2 1120. The N-CGL1 1080 injects electrons into the first emitting part 1000 and the P-CGL1 1090 injects holes into the second emitting part 1100.

The CGL2 1170 is disposed between the second emitting part 1100 and the third emitting part 1200. The CGL2 1170 may be a PN-junction CGL having a second N-type CGL (N-CGL2) 1180 and a second P-type CGL (P-CGL2) 1190. The N-CGL2 1080 is disposed between the ETL2 1150 and the HTL3 1220 and the P-CGL2 1190 is disposed between the N-CGL2 1180 and the HTL3 1220. The N-CGL2 1180 injects electrons into the second emitting part 1100 and the P-CGL2 1190 injects holes into the third emitting part 1200.

Each of the HIL 1010, the HTL1 1020, the HTL2 1120, the HTL3 1130, the EIL 120, the CGL1 1070 and the CGL2 1170 may independently include the same material as described above. Each of the HTL1 1020, the HTL2 1120 and the HTL3 1220 may comprise the same material or different material to each other. In addition, the CGL1 1070 may comprise the same material as or different material from the CGL2 1170.

The EML1 1040 includes a first dopant 1042 of a boron-based compound and a first host 1044 of an anthracene-based compound so that the EML1 1040 emits blue (B) light. The EML3 1240 includes a second dopant 1242 of a boron-based compound and a second host 1244 of an anthracene-based compound so that the EML3 1240 emits blue (B) light.

Each of the first dopant 1042 and the second dopant 1242 of the born-based compound may not be deuterated or partially deuterated, and may have independently the structure of Formulae 1A to 2. Each of the first host 1044 and the second host 1244 of the anthracene-based compound may be at least partially deuterated, and may have independently the structure of Formulae 3 to 4. The first dopant 1042 may be identical to or different from the second dopant 1242, and the first host 1044 may be identical to or different from the second host 1244.

In one exemplary embodiment, each of the contents of the first host 1044 and the second host 1244 may be independently about 70 wt % to about 99.9 wt % and each of the contents of the first dopant 1042 and the second dopant 1242 may be independently about 0.1 wt % to about 30 wt % in the EML1 1040 and in the EML3 1240, respectively. For example, the contents of the first dopant 1042 and the second dopant 1242 in the EML1 1040 and in the EML3 1240, respectively, may be about 0.1 wt % to about 10 wt %, for example, about 1 wt % to about 5 wt % so that both the EML1 1040 and the EML3 1240 can implement sufficient luminous efficiency and luminous lifespan.

Each of the EBL1 1030 and the EBL3 1230 prevents electrons from transporting from the EML1 1040 or EML3 1240 to the first electrode 710 or the CGL2 1170, respectively. Each of the EBL1 1030 and the EBL3 1230 may include a first electron blocking material 1032 and a third electron blocking material 1232, respectively. Each of the first electron blocking material 1032 and the third electron blocking material 1232 may comprise independently the amine-based compound having the structure of Formulae 5 to 6, respectively. The first electron blocking material 1032 may be identical to or different from the third electron blocking material 1232.

Each of the HBL1 1050 and the HBL3 1250 prevents holes from transporting from the EML1 1040 or EML3 1240 to the CGL1 1070 or the second electrode 720, respectively. Each of the HBL1 1050 and the HBL3 1250 may include a first hole blocking material 1052 and a third hole blocking material 1252, respectively. Each of the first hole blocking material 1052 and the third hole blocking material 1252 may comprise independently the azine-based compound having the structure of Formulae 7 to 8 and/or the benzimidazole-based compound having the structure of Formulae 9 to 10, respectively. The first hole blocking material 1052 may be identical to or different from the third hole blocking material 1252.

As described above, the compound having the structure of Formulae 7 to 10 has excellent electron transport property as well as excellent hole blocking property. Therefore, each of the HBL1 1050 and the HBL3 1250 may function as a hole blocking layer and an electron transport layer.

In one exemplary aspect, the EML2 1140 may emit yellow-green (YG) light. For example, the EML2 1140 may include yellow-green (YG) dopant 1143 and a host 1145.

Alternatively, the EML2 1140 may emit red-green (RG) light and may include red (R) dopant and green (G) dopant 1143 and a host 1145. In this case, the EML2 1140 may have a single-layered structure including the host, green (G) dopant and red (R) dopant, or may have a double-layered structure comprising a lower layer (first layer) including a host and green (G) dopant (or red (R) dopant) and an upper layer (second layer) including a host and red (R) dopant (or green (G) dopant).

In an alternative aspect, the EML2 1140 may have a triple-layered structure of a first layer including a host and red (R) dopant, a second layer including a host and yellow-green (YG) dopant and a third layer including a host and green (G) dopant. The dopant 1143 and the host 1145 in the EML2 1140 may be identical to the corresponding materials as described above referring to FIG. 6.

Each of the ETL1, the ETL2 1150, the ETL3, the EBL2 disposed between the HTL2 1120 and the EML2 1140 and the HBL2 disposed between the EML2 1140 and the ETL2 1150 may comprise the identical compounds to the corresponding material as described above.

Each of the EML1 1040 and the EML3 1240 includes the first and second dopants 1042 and 1242 of the boron-based compound and the first and second hosts 1044 and 1244 of the anthracene-based compound where at least one carbon atoms are deuterated, respectively. Each of the first and second dopants 1042 and 1242 of the boron-based compound may have independently an asymmetric chemical structure such as Formula 1B and may not be deuterated or partially deuterated. Also, each of the first and second hosts 1044 and 1244 of the anthracene-based compound may have a structure where two naphthyl moieties are linked directly or via the linker to the anthracene moiety and at least one protium, for example, all protiums are deuterated. Accordingly, the OLED D4 and the organic light emitting display device 600 can improve their luminous efficiency and luminous lifespan.

In addition, the OLED D4 and the organic light emitting display device 600 can maximize their luminous efficiency and luminous lifespan by applying the aryl amine-based compound having the structure of Formulae 5 and 6 into the EBL1 1030 and the EBL3 1230 as the first and third electron blocking materials 1032 and 1232, respectively, and optionally the azine-based compound having the structure of Formulae 7 to 8 and/or the benzimidazole-based compound having the structure of Formulae 9 to 10 into the HBL1 1050 and the HBL3 1250 as the first and third hole blocking materials 1052 and 1252, respectively. In addition, the OLED D4 includes the first and third emitting parts 1000 and 1020 each of which emits blue (B) light and the second emitting part 1100 emitting yellow-green (YG) or red-green (RG) light so that the OLED D4 can emit white (W) light In FIG. 7, a tandem-structured OLED D4 having three emitting parts are illustrated. Alternatively, an OLED may further include at least one additional emitting parts and at least one additional charge generation layer.

Figure 8:
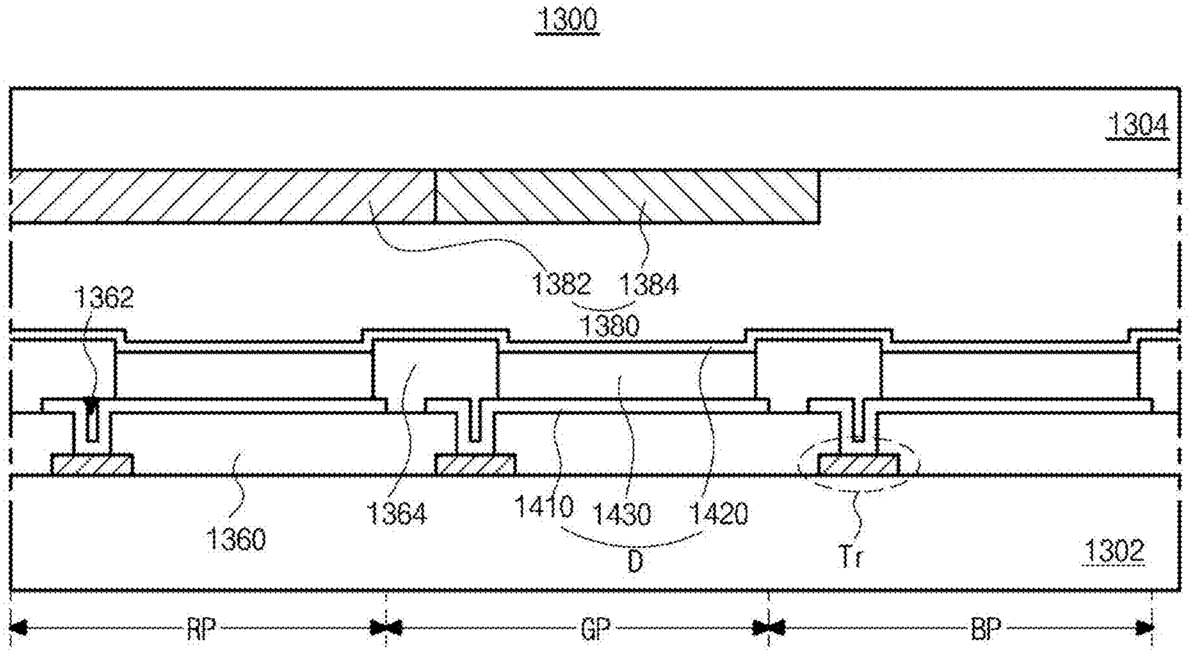
FIG. 8 is a cross-section view illustrating an organic light emitting display device in accordance with still another exemplary aspect of the present disclosure.

In addition, an organic light emitting device in accordance with the present disclosure may include a color conversion layer. FIG. 8 is a schematic cross-sectional view illustrating an organic light emitting display device in still another exemplary embodiment of the present disclosure.

As illustrated in FIG. 8, the organic light emitting display device 1300 comprises a first substrate 1302 that defines each of a red pixel region RP, a green pixel region GP and a blue pixel region BP, a second substrate 1304 facing the first substrate 1302, a thin film transistor Tr over the first substrate 1302, an organic light emitting diode (OLED) D disposed between the first and second substrates 1302 and 1304 and emitting blue (B) light and a color conversion layer 1380 disposed between the OLED D and the second substrate 1304. Although not shown in FIG. 8, a color filter layer may be disposed between the second substrate 1304 and the respective color conversion layer 1380.

The thin film transistor Tr is disposed over the first substrate 1302 correspondingly to each of the red pixel region RP, the green pixel region GP and the blue pixel region BP. A passivation layer 1360, which has a drain contact hole 1362 exposing one electrode, for example a drain electrode, constituting the thin film transistor Tr, is formed with covering the thin film transistor Tr over the whole first substrate 1302.

The OLED D, which includes a first electrode 1410, an emissive layer 1430 and the second electrode 1420, is disposed over the passivation layer 1360. The first electrode 1410 may be connected to the drain electrode of the thin film transistor Tr through the drain contact hole 1362. In addition, a bank layer 1364 covering edges of the first electrode 1410 is formed at the boundary between the red pixel region RP, the green pixel region GP and the blue pixel region BP. In this case, the OLED D may have a structure of FIG. 3 or FIG. 4 and can emit blue (B) light. The OLED D is disposed in each of the red pixel region RP, the green pixel region GP and the blue pixel region BP to provide blue (B) light.

The color conversion layer 1380 may include a first color conversion layer 1382 corresponding to the red pixel region RP and a second color conversion layer 1384 corresponding to the green pixel region GP. As an example, the color conversion layer 1380 may include an inorganic luminescent material such as quantum dot (QD).

The blue (B) light emitted from the OLED D in the red pixel region RP is converted into red (R) color light by the first color conversion layer 1382 and the blue (B) light emitted from the OLED D in the green pixel region GP is converted into green (G) color light by the second color conversion layer 1384. Accordingly, the organic light emitting display device 1300 can implement a color image.

In addition, when the light emitted from the OLED D is displayed through the first substrate 1302, the color conversion layer 1380 may be disposed between the OLED D and the first substrate 1302.

Synthesis Example 1: Synthesis of Compound 1-1

(1) Synthesis of Intermediate 1-1C

[Reaction Formula 1-1]

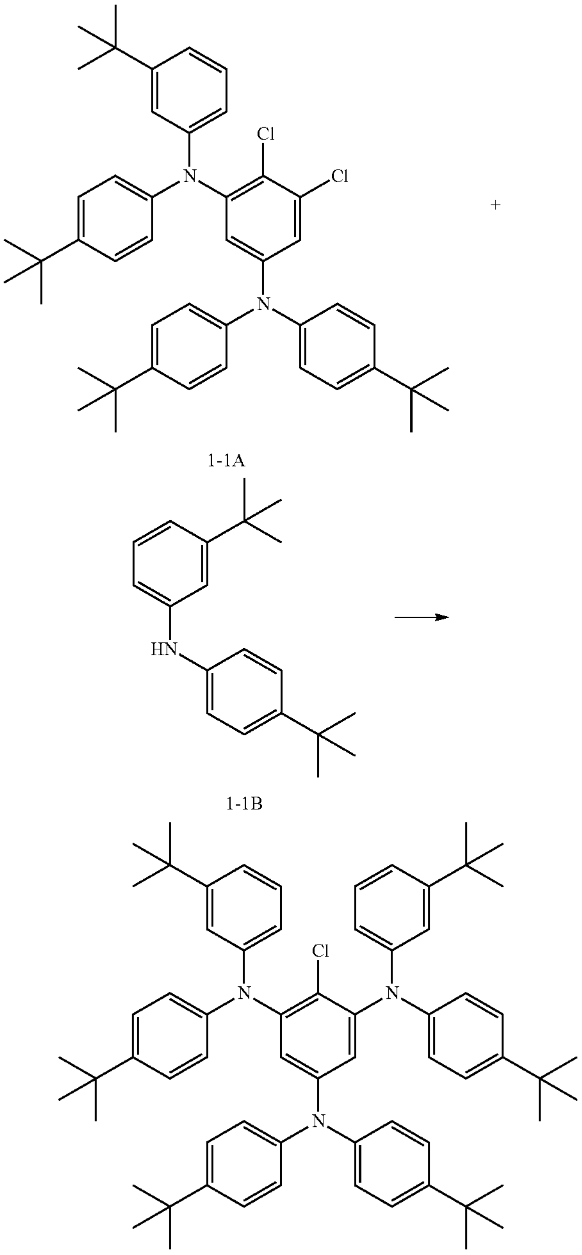

1-1A 1-1B 1-1C

Compound 1-1A (69.2 g, 98 mmol), Compound 1-1B (27.6 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-1C (58.1 g, yield: 84%).

(2) Synthesis of Compound 1-1

[Reaction Formula 1-2]

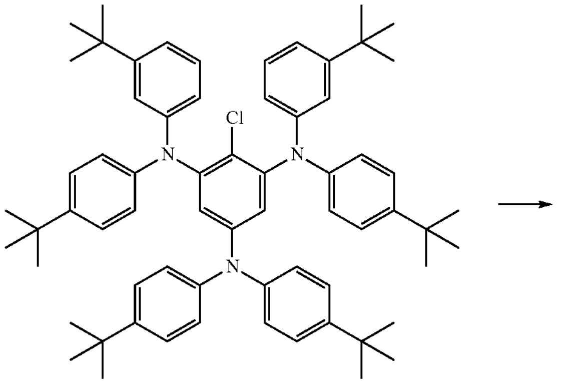

1-1C

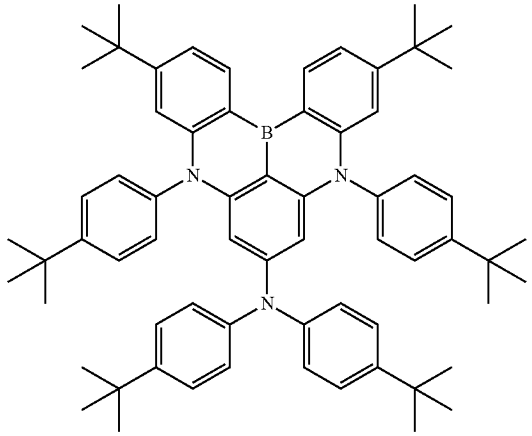

1-1

The Intermediate 1-1C (11.9 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at room temperature (RT) for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-1 (2.3 g, yield: 20%).

Synthesis Example 2: Synthesis of Compound 1-4

(1) Synthesis of Intermediate 1-4C

[Reaction Formula 2-1]

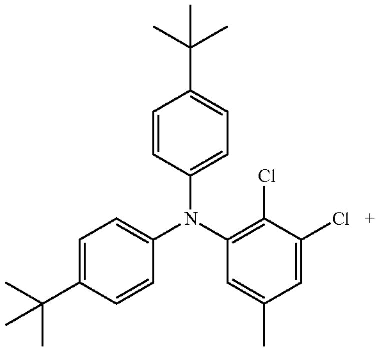

1-4A

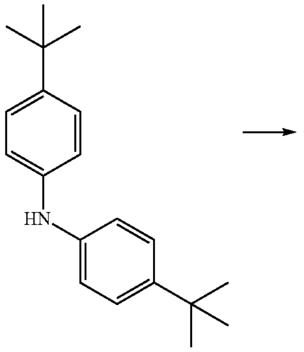

1-4B

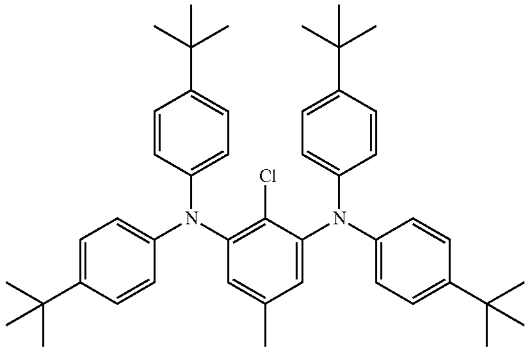

1-4C

Compound 1-4A (43.1 g, 98 mmol), Compound 1-4B (27.6 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-4C (57.1 g, yield: 85%).

(2) Synthesis of Compound 1-4

[Reaction Formula 2-2]

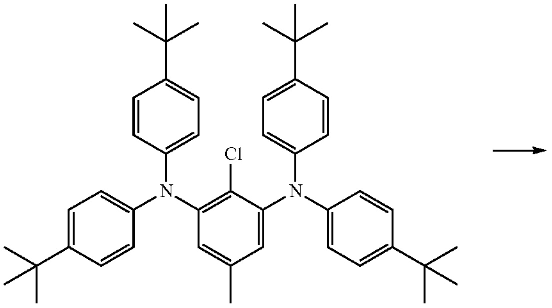

1-4C

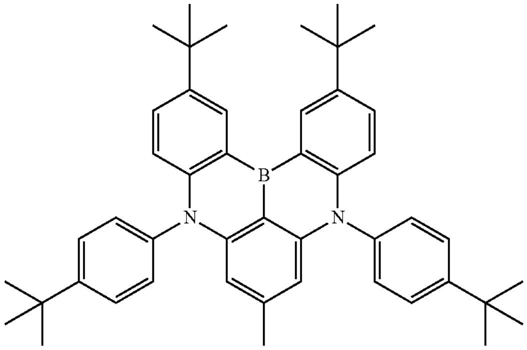

1-4

The Intermediate 1-4C (8.6 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-4 (1.9 g, yield: 23%).

Synthesis Example 3: Synthesis of Compound 1-6

(1) Synthesis of Intermediate 1-6C

[Reaction Formula 3-1]

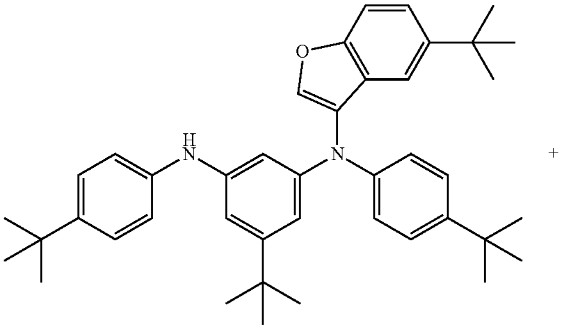

1-6A

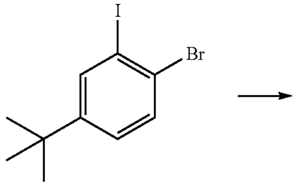

1-6B

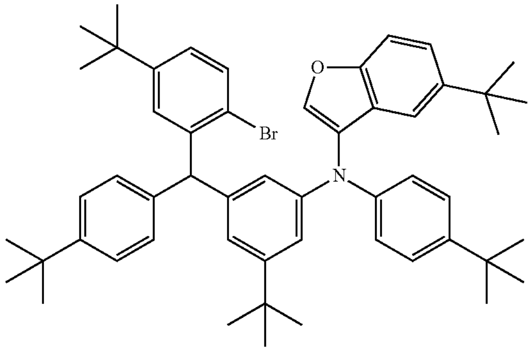

1-6C

Compound 1-6A (58.9 g, 98 mmol), Compound 1-6B (33.2 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-6C (59.7 g, yield: 75%).

(2) Synthesis of Compound 1-6

[Reaction Formula 3-2]

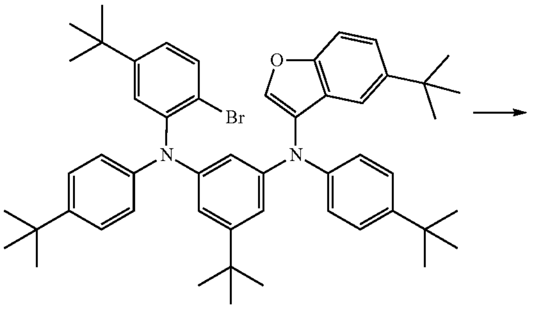

1-6C

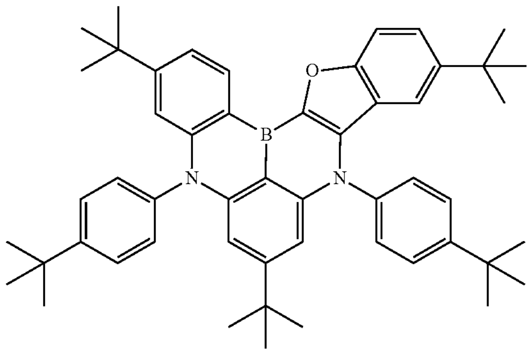

1-6

The Intermediate 1-6C (10.1 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-6 (1.9 g, yield: 21%).

Synthesis Example 4: Synthesis of Compound 1-8

(1) Synthesis of Intermediate 1-8C

[Reaction Formula 4-1]

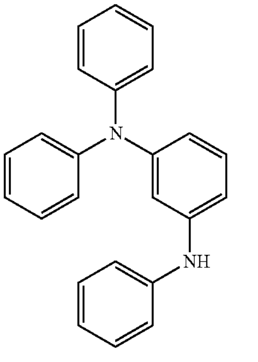

+

1-8A

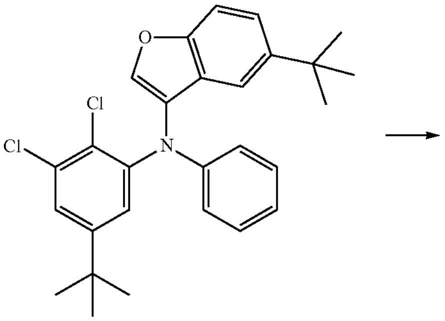

1-8B

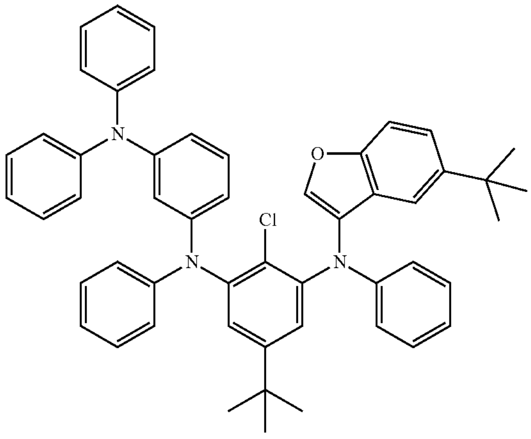

1-8C

Compound 1-8A (33.0 g, 98 mmol), Compound 1-8B (45.7 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-8C (54.1 g, yield: 72%).

(2) Synthesis of Compound 1-8

[Reaction Formula 4-2]

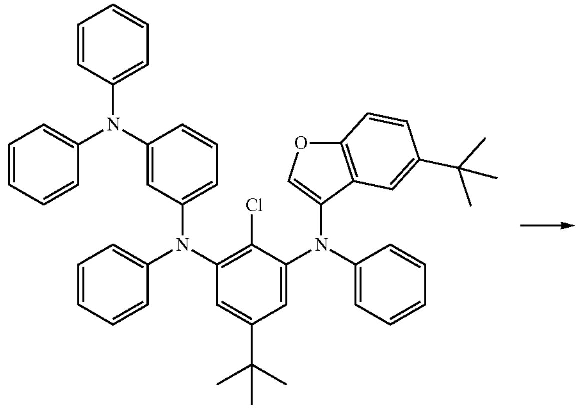

1-8C

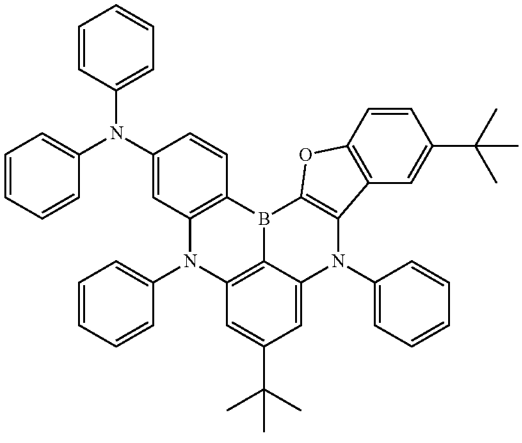

1-8

The Intermediate 1-8C (9.6 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-8 (2.0 g, yield: 21%).

Synthesis Example 5: Synthesis of Compound 1-11

(1) Synthesis of Intermediate 1-11C

[Reaction Formula 5-1]

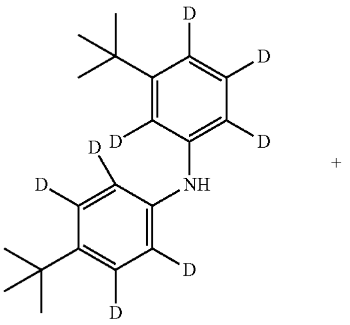

1-11A

+

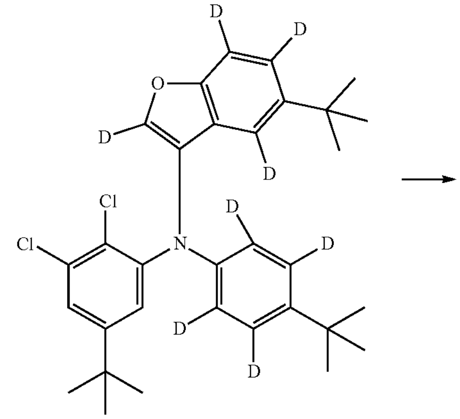

1-11B

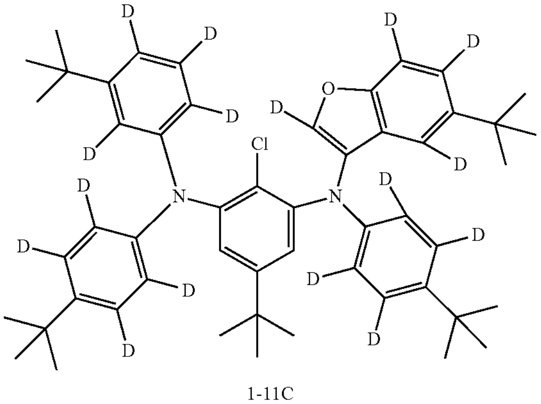

1-11C

Compound 1-11A (28.4 g, 98 mmol), Compound 1-11B (52.0 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-11C (39.9 g, yield: 52%).

(2) Synthesis of Compound 1-11

[Reaction Formula 5-2]

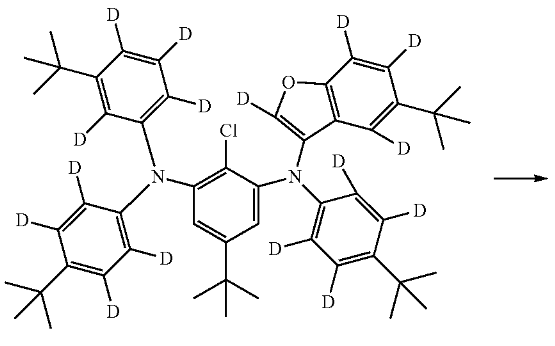

1-11C

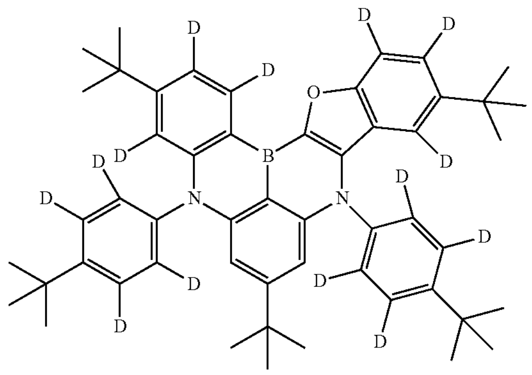

1-11

The Intermediate 1-11C (9.8 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-11 (1.4 g, yield: 15%).

Synthesis Example 6: Synthesis of Compound 1-12

(1) Synthesis of Intermediate 1-12C

[Reaction Formula 6-1]

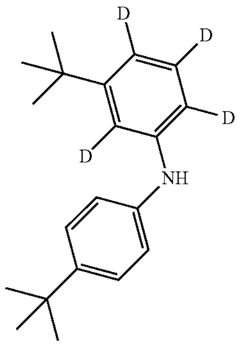

1-12A

+

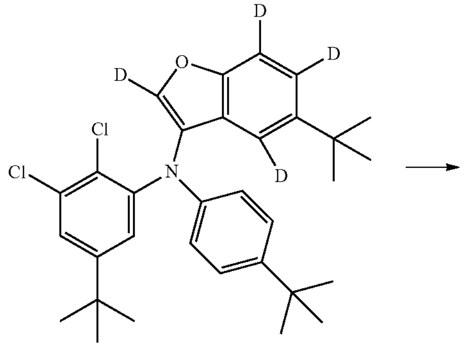

1-12B

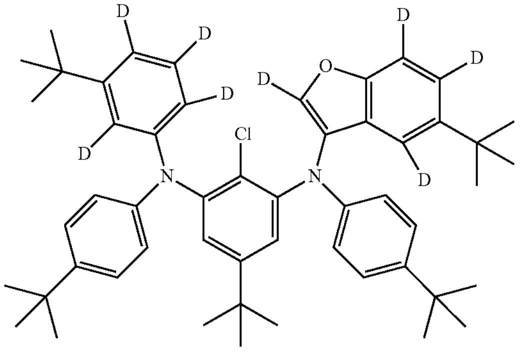

1-12C

Compound 1-12A (28.0 g, 98 mmol), Compound 1-12B (51.6 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-12C (44.1 g, yield: 58%).

(2) Synthesis of Compound 1-12

[Reaction Formula 6-2]

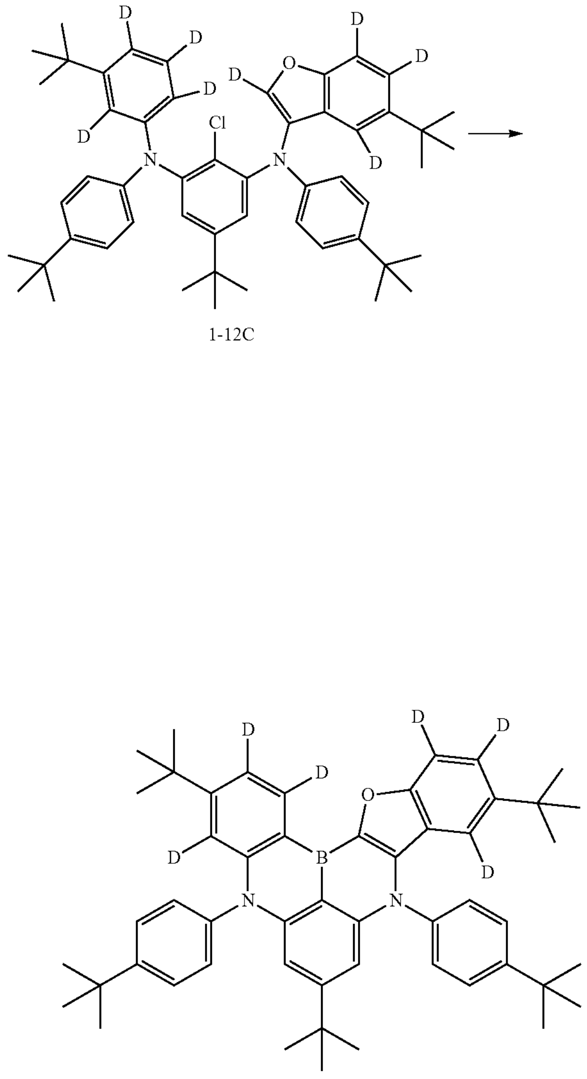

1-12C 1-12

The Intermediate 1-12C (9.7 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-12 (1.7 g, yield: 18%).

Synthesis Example 7: Synthesis of Compound 1-13

(1) Synthesis of Intermediate 1-13C

[Reaction Formula 7-1]

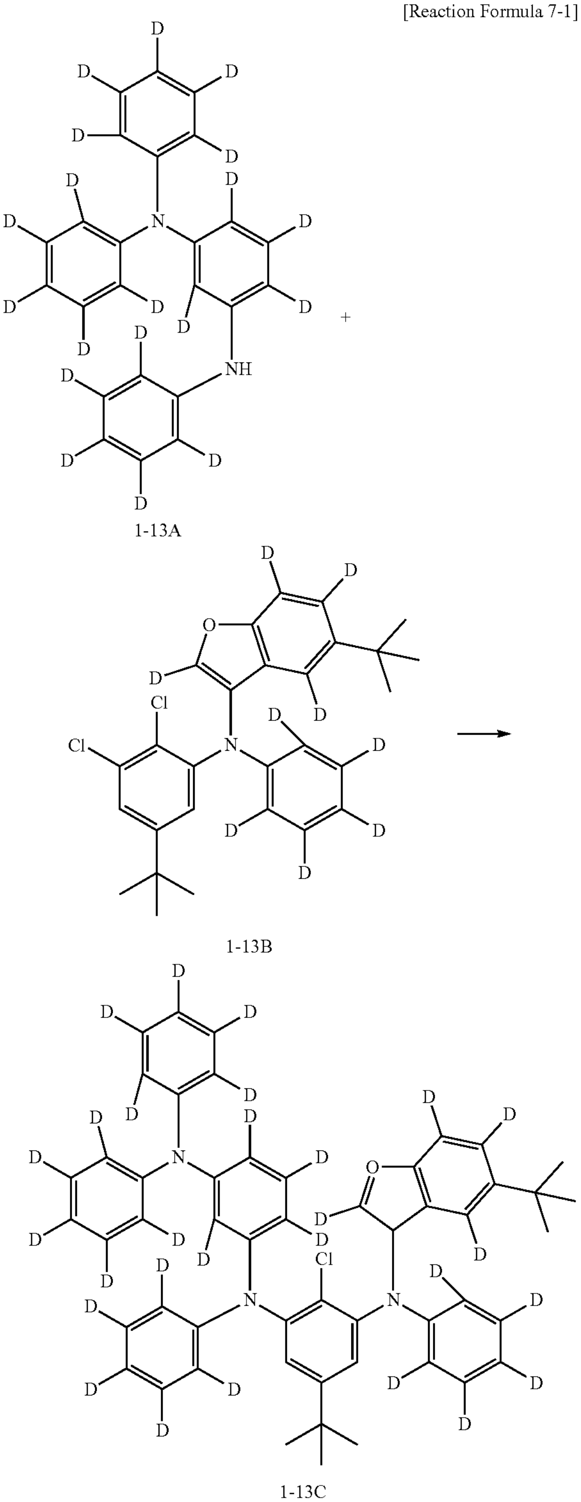

1-13A 1-13B 1-13C

Compound 1-13A (34.8 g, 98 mmol), Compound 1-13B (46.6 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-13C (41.3 g, yield: 53%).

(2) Synthesis of Compound 1-13

[Reaction Formula 7-2]

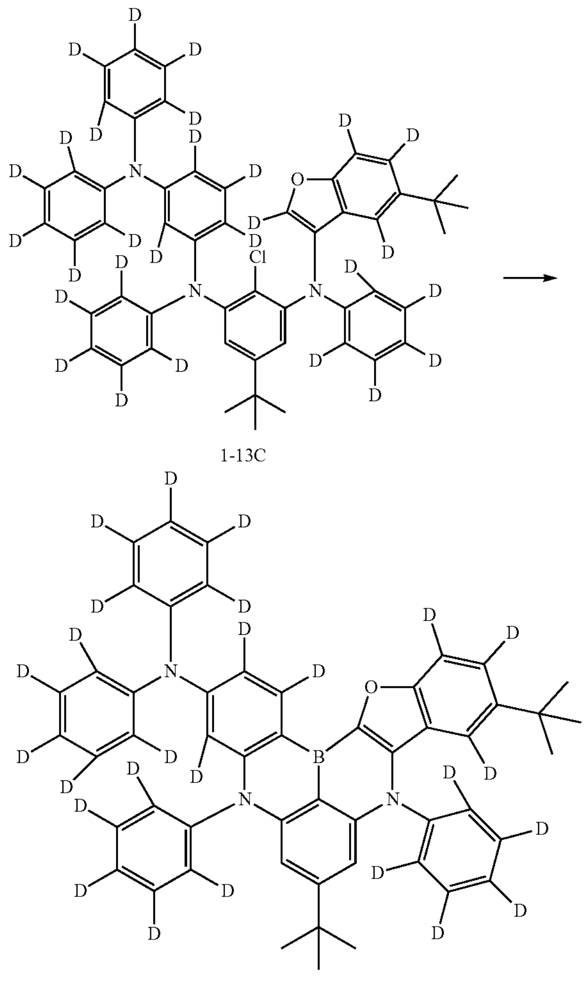

1-13C 1-13

The Intermediate 1-13C (9.9 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-13 (1.4 g, yield: 15%).

Synthesis Example 8: Synthesis of Compound 1-17

(1) Synthesis of Intermediate 1-17C

[Reaction Formula 8-1]

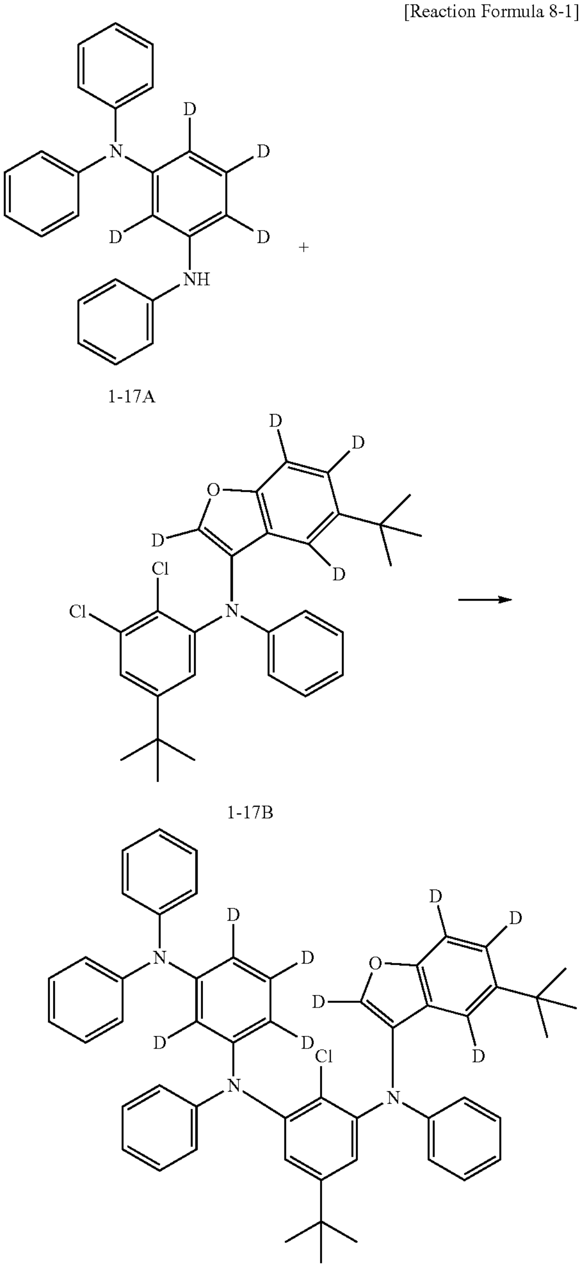

1-17A 1-17B 1-17C

Compound 1-17A (33.4 g, 98 mmol), Compound 1-17B (46.1 g, 98 mmol), palladium acetate (0.45 g, 2 mmol), sodium tert-butoxide (18.9 g, 196 mmol), tri-tert-butylphosphine (0.8 g, 4 mmol) and toluene (300 ml) were put into a 500 ml reaction vessel, and then the solution was refluxed for 5 hours with stirring. After the reaction was complete, the solution was filtered, and then the filtrate was concentrated. A crude product was purified with column chromatography to give the Intermediate 1-17C (47.1 g, yield: 62%).

(2) Synthesis of Compound 1-17

[Reaction Formula 8-2]

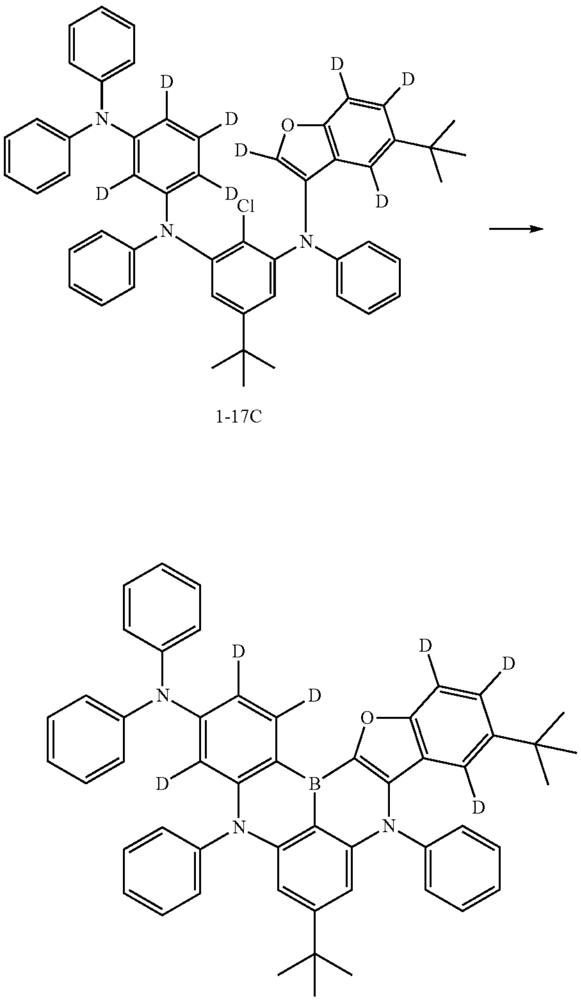

1-17C 1-17

The Intermediate 1-17C (9.7 g, 12.5 mmol) and tert-butyl benzene (60 ml) were put into a 500 ml reaction vessel. N-butyl lithium (45 ml, 37.5 mmol) was added dropwisely into the reaction vessel at −78° C., and then the solution was stirred at 60° C. for 3 hours. Nitrogen gas was blown into the reaction vessel at 60° C. to remove a byproduct, boron tribromide (6.3 g, 25 mmol) was added dropwisely to the solution at −78° C., and then the solution was stirred at RT for 1 hour. N,N-diisopropyl ethyl amine (3.2 g, 25 mmol) was added dropwisely to the solution at 0° C., and then the solution was stirred at 120° C. for 2 hours. After the reaction was complete, sodium acetate aqueous solution was added into the reaction vessel at RT, and then the solution was stirred. An organic layer was extracted with ethyl acetate and was concentrated, and then a crude product was purified with column chromatography to give Compound 1-17 (1.6 g, yield: 17%).

Synthesis Example 9: Synthesis of Compound 2-1

[Reaction Formula 9]

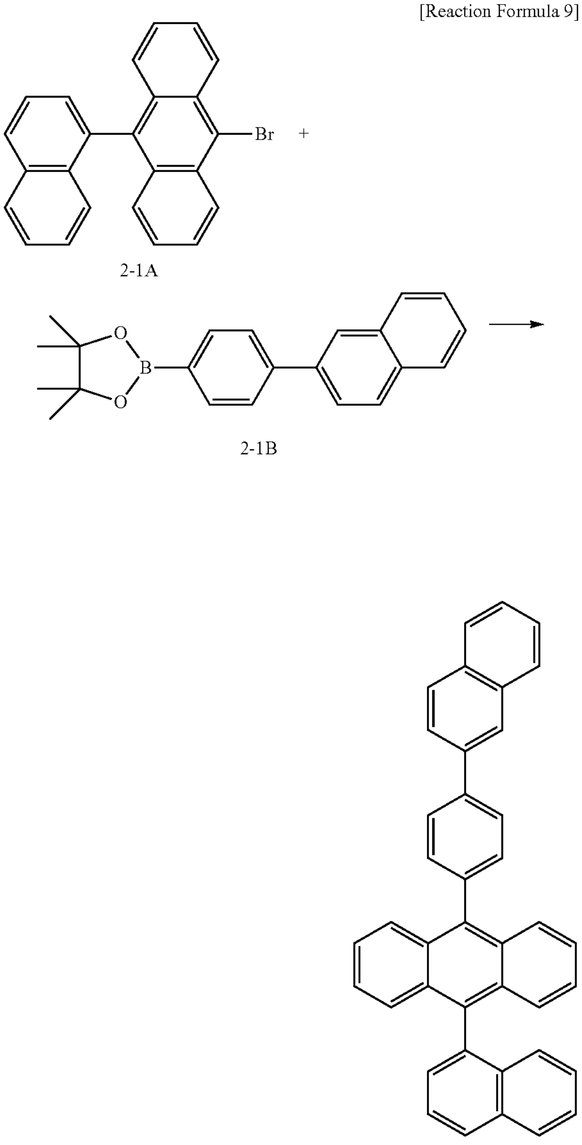

2-1A 2-1B 2-1

Compound 2-1A (2.0 g, 5.2 mmol), Compound 2-1B (1.5 g, 5.7 mmol), tris(dibenzylideneacetone)dipalladium(0) ($Pd_2(dba)_3$, 0.24 g, 0.26 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC (high-performance liquid chromatography). After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-1 (2.3 g, yield: 86%) of white powder.

Synthesis Example 10: Synthesis of Compound 2-2

[Reaction Formula 10]

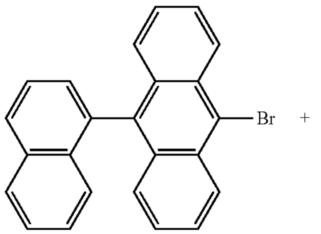

2-2A

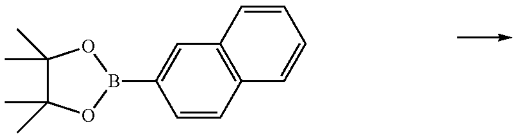

2-2B

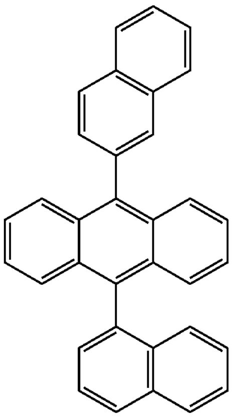

2-2

Compound 2-2A (2.0 g, 5.2 mmol), Compound 2-2B (1.5 g, 5.7 mmol), $Pd_2(dba)_3$ (0.24 g, 0.26 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC. After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-2 (2.0 g, yield: 89%) of white powder.

Synthesis Example 11: Synthesis of Compound 2-3

[Reaction Formula 11]

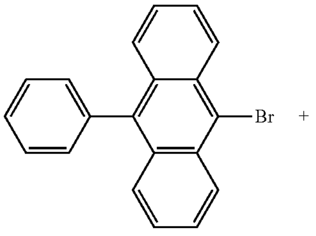

2-3A

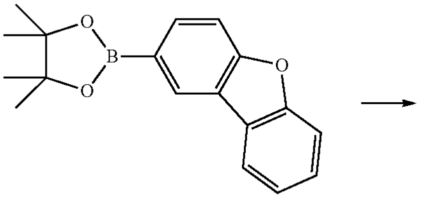

2-3B

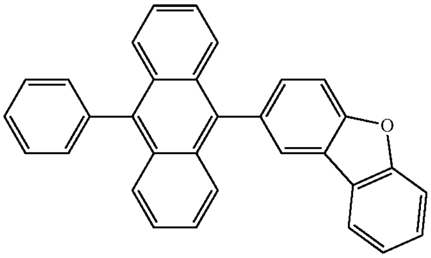

2-3

Compound 2-3A (2.0 g, 6.0 mmol), Compound 2-3B (1.9 g, 6.6 mmol), $Pd_2(dba)_3$ (0.3 g, 0.3 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC. After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-3 (2.0 g, yield: 79%) of white powder.

Synthesis Example 12: Synthesis of Compound 2-4

[Reaction Formula 12]

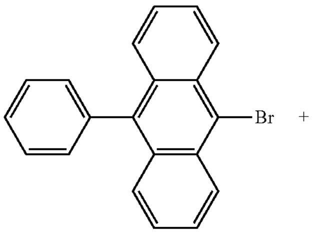

2-4A

-continued

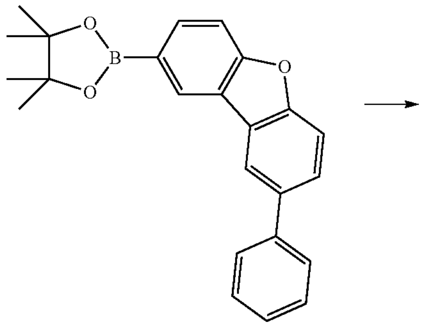

2-4B

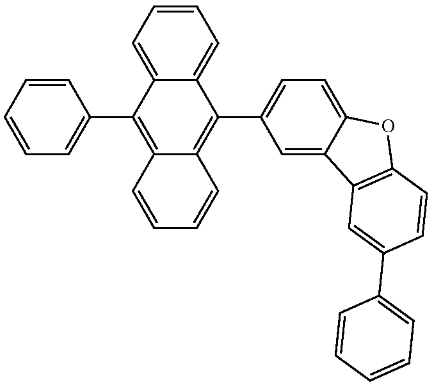

2-4

Compound 2-4A (2.0 g, 6.0 mmol), Compound 2-4B (2.4 g, 6.6 mmol), $Pd_2(dba)_3$ (0.3 g, 0.3 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC. After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-4 (2.0 g, yield: 67%) of white powder.

Synthesis Example 13: Synthesis of Compound 2-5

[Reaction Formula 13]

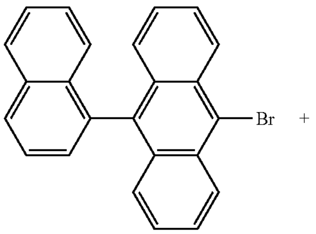

2-5A

-continued

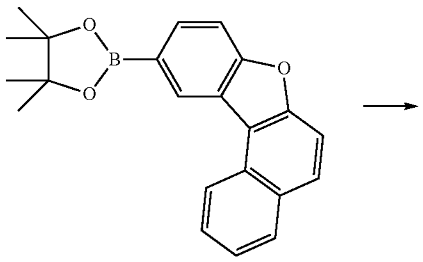

2-5B

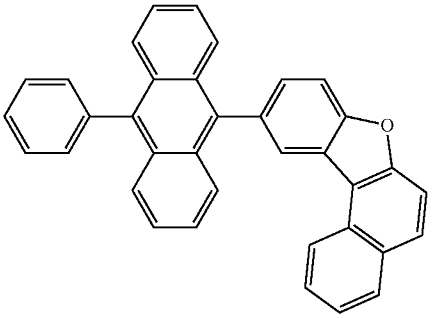

2-5

Compound 2-5A (2.0 g, 5.2 mmol), Compound 2-5B (2.0 g, 5.7 mmol), $Pd_2(dba)_3$ (0.24 g, 0.26 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC. After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-5 (2.0 g, yield: 81%) of white powder.

Synthesis Example 14: Synthesis of Compound 2-6

[Reaction Formula 14]

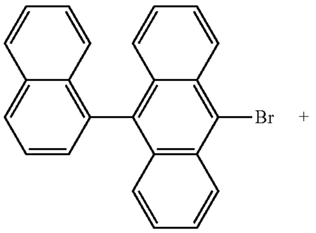

2-6A

-continued

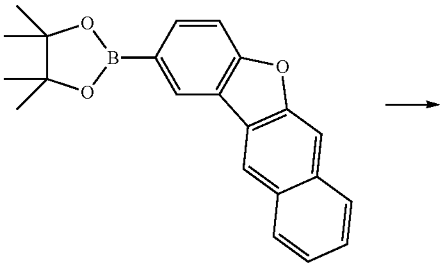

2-6B

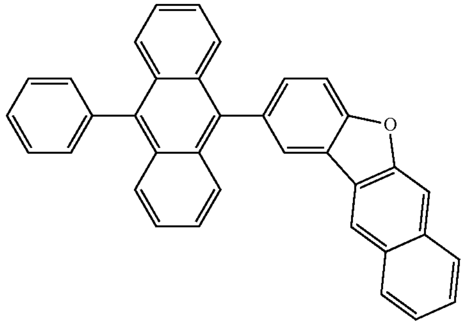

2-6

Compound 2-6A (2.0 g, 5.2 mmol), Compound 2-6B (2.0 g, 5.7 mmol), $Pd_2(dba)_3$ (0.24 g, 0.26 mmol) and toluene (50 ml) were put into a 250 ml reaction vessel in a dry box. The reaction vessel was removed from the dry box, and then sodium carbonate anhydrous (2M, 20 ml) was added into the solution. The reactants were stirred and heated at 90° C. overnight. The reaction was monitored by HPLC. After the solution was cooled to RT, an organic layer was separated. An aqueous layer was washed with dichloromethane and the organic layer was concentrated with rotary evaporation to obtain a gray powder. The gray powder was purified with alumina, precipitated with hexane, and purified with silica-gel column chromatography to give Compound 2-6 (2.0 g, yield: 81%) of white powder.

Synthesis Example 15: Synthesis of Compound 2-7

[Reaction Formula 15]

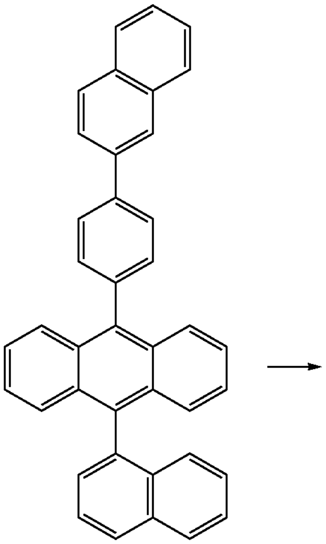

2-1

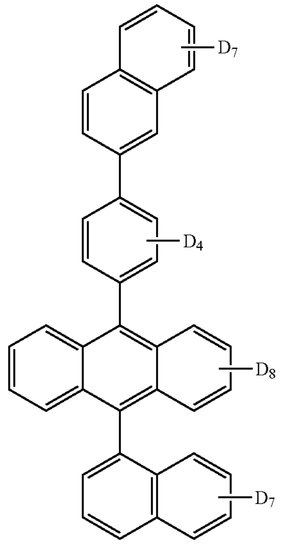

2-7

Aluminum chloride (0.5 g, 3.6 mmol) was added into a solution of Compound 2-1 (5.0 g, 9.9 mmol) dissolved in perdeuterobenzene (100 ml) under nitrogen atmosphere. Obtained mixture was stirred at RT for 6 hours, and then $D_2O$ (50 ml) was added into the mixture. After an organic layer was separated from an aqueous layer, the aqueous layer was washed with dichloromethane (30 ml). The obtained organic layer was dried with $MgSO_4$ and volatile components were removed by rotary evaporation. A crude product was purified with column chromatography to give Compound 2-7 (4.5 g, yield: 85%) of white powder.

Synthesis Example 16: Synthesis of Compound 2-8

[Reaction Formula 15]

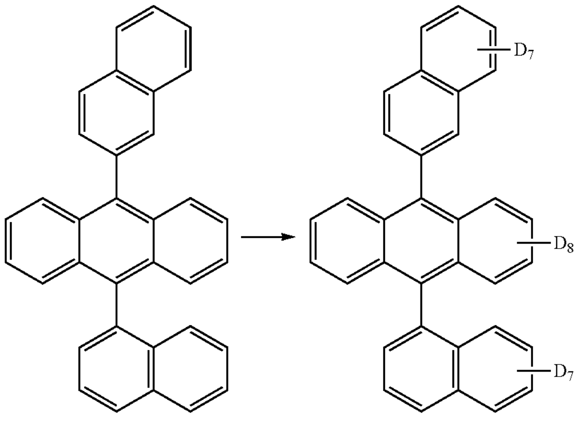

2-2 2-8

Aluminum chloride (0.9 g, 4.3 mmol) was added into a solution of Compound 2-2 (5.0 g, 11.6 mmol) dissolved in perdeuterobenzene (120 ml) under nitrogen atmosphere. Obtained mixture was stirred at RT for 6 hours, and then $D_2O$ (70 ml) was added into the mixture. After an organic layer was separated from an aqueous layer, the aqueous layer was washed with dichloromethane (50 ml). The obtained organic layer was dried with $MgSO_4$ and volatile components were removed by rotary evaporation. A crude product was purified with column chromatography to give Compound 2-8 (4.0 g, yield: 76%) of white powder.

Synthesis Example 17: Synthesis of Compound 2-9

[Reaction Formula 17]

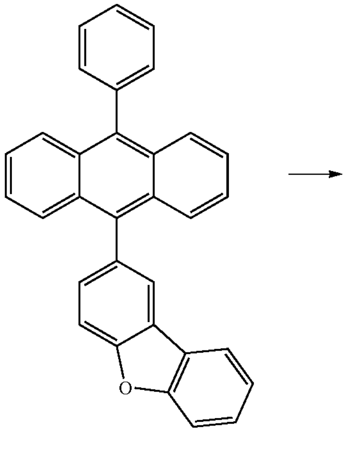

2-3

-continued

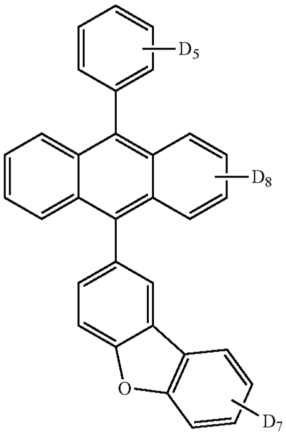

2-9

Aluminum chloride (0.9 g, 4.3 mmol) was added into a solution of Compound 2-3 (5.0 g, 11.9 mmol) dissolved in perdeuterobenzene (120 ml) under nitrogen atmosphere. Obtained mixture was stirred at RT for 6 hours, and then $D_2O$ (70 ml) was added into the mixture. After an organic layer was separated from an aqueous layer, the aqueous layer was washed with dichloromethane (50 ml). The obtained organic layer was dried with $MgSO_4$ and volatile components were removed by rotary evaporation. A crude product was purified with column chromatography to give Compound 2-9 (3.0 g, yield: 57%) of white powder.

Synthesis Example 18: Synthesis of Compound 2-10

[Reaction Formula 18]

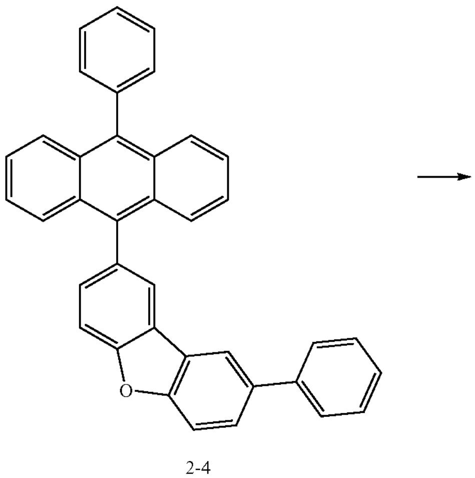

2-4

-continued

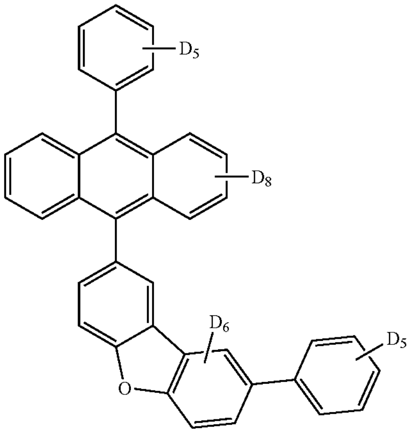

2-10

Aluminum chloride (0.9 g, 4.3 mmol) was added into a solution of Compound 2-4 (5.0 g, 10.1 mmol) dissolved in perdeuterobenzene (120 ml) under nitrogen atmosphere. Obtained mixture was stirred at RT for 6 hours, and then $D_2O$ (70 ml) was added into the mixture. After an organic layer was separated from an aqueous layer, the aqueous layer was washed with dichloromethane (50 ml). The obtained organic layer was dried with $MgSO_4$ and volatile components were removed by rotary evaporation. A crude product was purified with column chromatography to give Compound 2-10 (3.5 g, yield: 67%) of white powder.

Synthesis Example 19: Synthesis of Compound 2-11

[Reaction Formula 19]

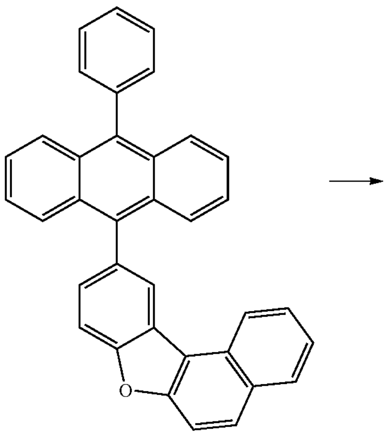

2-5

-continued

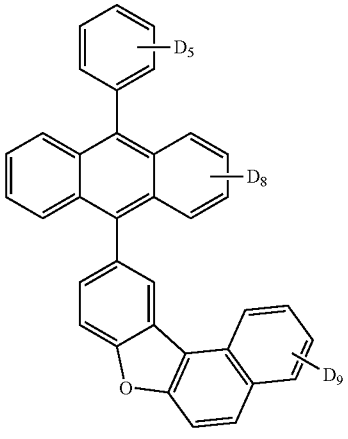

2-11

Aluminum chloride (0.9 g, 4.3 mmol) was added into a solution of Compound 2-5 (5.0 g, 10.6 mmol) dissolved in perdeuterobenzene (120 ml) under nitrogen atmosphere. Obtained mixture was stirred at RT for 6 hours, and then $D_2O$ (70 ml) was added into the mixture. After an organic layer was separated from an aqueous layer, the aqueous layer was washed with dichloromethane (50 ml). The obtained organic layer was dried with $MgSO_4$ and volatile components were removed by rotary evaporation. A crude product was purified with column chromatography to give Compound 2-11 (4.0 g, yield: 77%) of white powder.

Synthesis Example 20: Synthesis of Compound 2-12

[Reaction Formula 20]

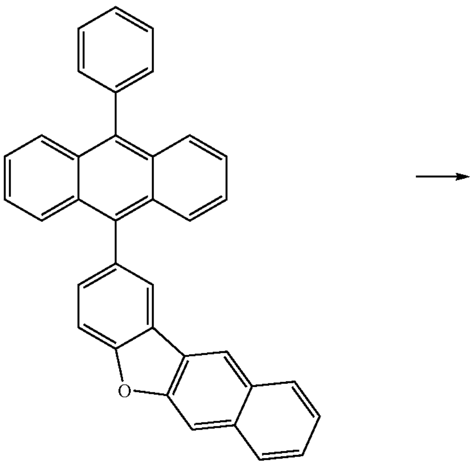

2-6

-continued

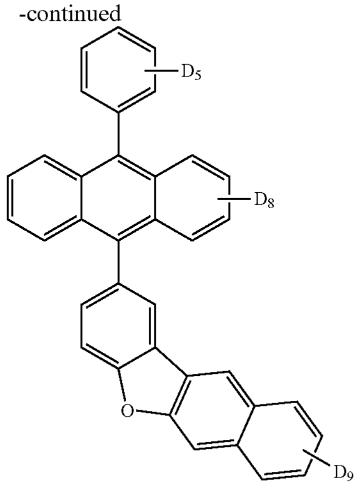

2-12

Aluminum chloride (0.9 g, 4.3 mmol) was added into a solution of Compound 2-6 (5.0 g, 10.6 mmol) dissolved in perdeuterobenzene (120 ml) under nitrogen atmosphere. Obtained mixture was stirred at RT for 6 hours, and then $D_2O$ (70 ml) was added into the mixture. After an organic layer was separated from an aqueous layer, the aqueous layer was washed with dichloromethane (50 ml). The obtained organic layer was dried with $MgSO_4$ and volatile components were removed by rotary evaporation. A crude product was purified with column chromatography to give Compound 2-12 (4.3 g, yield: 82%) of white powder.

Fabrication of Organic Light Emitting Diode (OLED) 1

A glass substrate (40 mm×40 mm×0.5 mm) onto which ITO was coated as a thin film was washed and ultrasonically cleaned by solvent such as isopropyl alcohol, acetone and distilled water for 5 minutes and dried at 100° C. oven. After cleaning the substrate, the substrate was treated with $O_2$ plasma under vacuum for 2 minutes and then transferred to a vacuum chamber for depositing emission layer. Subsequently, an emissive layer and a cathode were deposited by evaporation from a heating boat under about 5~7×$10^{-7}$ Torr with a deposition rate of 1 Å/s as the following order:

An HIL (Formula 11 (97 wt %) and Formula 12 (3 wt %), 100 Å); an HTL (Formula 11, 100 Å); an EBL (H23 in Formula 6, 100 Å); an EML (Host (H, 98 wt %) and Dopant (D, 2 wt %), 200 Å); an HBL (E1 in Formula 8, 100 Å); an EIL (Formula 13 (98 wt %), Li (2 wt %), 200 Å); and a cathode (Al, 500 Å).

And then, the OLED was encapsulated with UV-curable epoxy and moisture getter.

Comparative Examples 1-8 (Ref.1-8): Fabrication of OLED

An OLED where the EML includes Compound 2-1 as a host and each of Compound 1-1 (Ref.1), Compound 1-4 (Ref.2), Compound 1-6 (Ref.3), Compound 1-8 (Ref.4), Compound 1-11 (Ref.5), Compound 1-12 (Ref.6), Compound 1-13 (Ref.7) and Compound 1-17 (Ref.8) in Formula 3 as a dopant, respectively, was fabricated.

Comparative Examples 9-16 (Ref.9-16): Fabrication of OLED

An OLED where the EML includes Compound 2-2 as a host and each of Compound 1-1 (Ref.9), Compound 1-4 (Ref.10), Compound 1-6 (Ref.11), Compound 1-8 (Ref.12), Compound 1-11 (Ref.13), Compound 1-12 (Ref.14), Compound 1-13 (Ref.15) and Compound 1-17 (Ref.18) in Formula 3 as a dopant, respectively, was fabricated.

Experimental Example 1: Measurement of Luminous Properties of OLEDs

Each of the OLEDs, having 9 $mm^2$ of emission area, fabricated in Comparative Examples 1 to 16 connected to an external power source and then luminous properties for all the OLEDs were evaluated using a constant current source (KEITHILEY) and a photometer PR650 at room temperature. In particular, driving voltage (V), current efficiency (cd/A) and CIE color coordinates at a current density of 10 $mA/cm^2$ and time period ($T_{95}$) at which the luminance was reduced to 95% from initial luminance at 40° C. and at a current density of 22.5 $mA/m^2$. The measurement results are indicated in the following Table 1.

TABLE 1

Luminous Properties of OLED

| Sample | Dopant | Host | V | EQE (%) | CIE(x,y) | $T_{95}$ (hr) |
|---|---|---|---|---|---|---|
| Ref. 1 | 1-1 | 2-1 | 3.99 | 6.35 | (0.140, 0.061) | 63 |
| Ref. 2 | 1-4 | 2-1 | 3.94 | 6.33 | (0.131, 0.089) | 68 |
| Ref. 3 | 1-6 | 2-1 | 3.90 | 6.61 | (0.139, 0.074) | 88 |
| Ref. 4 | 1-8 | 2-1 | 3.88 | 6.63 | (0.137, 0.079) | 82 |
| Ref. 5 | 1-11 | 2-1 | 3.89 | 6.61 | (0.140, 0.074) | 101 |
| Ref. 6 | 1-12 | 2-1 | 3.90 | 6.59 | (0.140, 0.073) | 95 |
| Ref. 7 | 1-13 | 2-1 | 3.91 | 6.64 | (0.137, 0.080) | 94 |
| Ref. 8 | 1-17 | 2-1 | 3.91 | 6.58 | (0.137, 0.079) | 89 |
| Ref. 9 | 1-1 | 2-2 | 4.20 | 6.24 | (0.140, 0.060) | 69 |
| Ref. 10 | 1-4 | 2-2 | 4.20 | 6.22 | (0.131, 0.090) | 74 |
| Ref. 11 | 1-6 | 2-2 | 4.15 | 6.49 | (0.138, 0.074) | 96 |
| Ref. 12 | 1-8 | 2-2 | 4.19 | 6.51 | (0.137, 0.079) | 106 |
| Ref. 13 | 1-11 | 2-2 | 4.20 | 6.50 | (0.140, 0.074) | 110 |
| Ref. 14 | 1-12 | 2-2 | 4.21 | 6.47 | (0.141, 0.074) | 103 |
| Ref. 15 | 1-13 | 2-2 | 4.20 | 6.53 | (0.138, 0.080) | 102 |
| Ref. 16 | 1-17 | 2-2 | 4.19 | 6.47 | (0.137, 0.079) | 96 |

Comparative Examples 17-24 (Ref.17-24): Fabrication of OLED

An OLED where the EML includes Compound 2-3 as a host and Compound 1-1 (Ref.17), Compound 1-4 (Ref.18), Compound 1-6 (Ref.19), Compound 1-8 (Ref.20), Compound 1-11 (Ref.21), Compound 1-12 (Ref.22), Compound 1-13 (Ref.23) and Compound 1-17 (Ref.24) in Formula 3 as a dopant, respectively, was fabricated.

Comparative Examples 25-32 (Ref.25-32): Fabrication of OLED

An OLED where the EML includes Compound 2-4 as a host and Compound 1-1 (Ref.25), Compound 1-4 (Ref.26), Compound 1-6 (Ref.27), Compound 1-8 (Ref.28), Compound 1-11 (Ref.29), Compound 1-12 (Ref.30), Compound 1-13 (Ref.31) and Compound 1-17 (Ref.32) in Formula 3 as a dopant, respectively, was fabricated.

Experimental Example 2: Measurement of Luminous Properties of OLEDs

Luminous properties for each of the OLEDs fabricated in Comparative Examples 17-32 were measured using the same procedure as in Experimental Example 1. The measurement results are indicated in the following Table 2.

TABLE 2

| Luminous Properties of OLEDs | | | | | | |
|---|---|---|---|---|---|---|
| Sample | Dopant | Host | V | EQE (%) | CIE(x,y) | $T_{95}$ (hr) |
| Ref. 17 | 1-1 | 2-3 | 3.80 | 6.21 | (0.140, 0.063) | 56 |
| Ref. 18 | 1-4 | 2-3 | 3.79 | 6.17 | (0.130, 0.092) | 61 |
| Ref. 19 | 1-6 | 2-3 | 3.80 | 6.45 | (0.139, 0.076) | 79 |
| Ref. 20 | 1-8 | 2-3 | 3.78 | 6.47 | (0.138, 0.081) | 73 |
| Ref. 21 | 1-11 | 2-3 | 3.78 | 6.46 | (0.141, 0.075) | 90 |
| Ref. 22 | 1-12 | 2-3 | 3.78 | 6.44 | (0.141, 0.075) | 85 |
| Ref. 23 | 1-13 | 2-3 | 3.80 | 6.49 | (0.136, 0.081) | 84 |
| Ref. 24 | 1-17 | 2-3 | 3.79 | 6.42 | (0.136, 0.081) | 79 |
| Ref. 25 | 1-1 | 2-4 | 3.80 | 6.22 | (0.139, 0.062) | 56 |
| Ref. 26 | 1-4 | 2-4 | 3.79 | 6.20 | (0.131, 0.092) | 60 |
| Ref. 27 | 1-6 | 2-4 | 3.80 | 6.43 | (0.137, 0.081) | 80 |
| Ref. 28 | 1-8 | 2-4 | 3.79 | 6.42 | (0.136, 0.084) | 73 |
| Ref. 29 | 1-11 | 2-4 | 3.81 | 6.47 | (0.139, 0.076) | 91 |
| Ref. 30 | 1-12 | 2-4 | 3.80 | 6.44 | (0.139, 0.077) | 84 |
| Ref. 31 | 1-13 | 2-4 | 3.79 | 6.50 | (0.136, 0.084) | 83 |
| Ref. 32 | 1-17 | 2-4 | 3.80 | 6.43 | (0.135, 0.087) | 80 |

Comparative Examples 33-40 (Ref.33-40): Fabrication of OLED

An OLED where the EML includes Compound 2-5 as a host and Compound 1-1 (Ref.33), Compound 1-4 (Ref.34), Compound 1-6 (Ref.35), Compound 1-8 (Ref.36), Compound 1-11 (Ref.37), Compound 1-12 (Ref.38), Compound 1-13 (Ref.39) and Compound 1-17 (Ref.40) in Formula 3 as a dopant, respectively, was fabricated.

Comparative Examples 41-48 (Ref.41-48): Fabrication of OLED

An OLED where the EML includes Compound 2-6 as a host and Compound 1-1 (Ref.41), Compound 1-4 (Ref.42), Compound 1-6 (Ref.43), Compound 1-8 (Ref.44), Compound 1-11 (Ref.45), Compound 1-12 (Ref.46), Compound 1-13 (Ref.47) and Compound 1-17 (Ref.48) in Formula 3 as a dopant, respectively, was fabricated.

Experimental Example 3: Measurement of Luminous Properties of OLEDs

Luminous properties for each of the OLEDs fabricated in Comparative Examples 33-48 were measured using the same procedure as in Experimental Example 1. The measurement results are indicated in the following Table 3.

TABLE 3

| Luminous Properties of OLEDs | | | | | | |
|---|---|---|---|---|---|---|
| Sample | Dopant | Host | V | EQE (%) | CIE(x,y) | $T_{95}$ (hr) |
| Ref. 33 | 1-1 | 2-5 | 3.65 | 6.15 | (0.140, 0.064) | 51 |
| Ref. 34 | 1-4 | 2-5 | 3.61 | 6.12 | (0.130, 0.094) | 55 |
| Ref. 35 | 1-6 | 2-5 | 3.62 | 6.10 | (0.138, 0.082) | 75 |
| Ref. 36 | 1-8 | 2-5 | 3.60 | 6.12 | (0.138, 0.085) | 68 |
| Ref. 37 | 1-11 | 2-5 | 3.62 | 6.10 | (0.141, 0.080) | 86 |
| Ref. 38 | 1-12 | 2-5 | 3.63 | 6.15 | (0.141, 0.080) | 79 |
| Ref. 39 | 1-13 | 2-5 | 3.62 | 6.15 | (0.136, 0.085) | 78 |
| Ref. 40 | 1-17 | 2-5 | 3.63 | 6.16 | (0.136, 0.088) | 75 |
| Ref. 41 | 1-1 | 2-6 | 3.65 | 6.16 | (0.140, 0.064) | 50 |
| Ref. 42 | 1-4 | 2-6 | 3.60 | 6.13 | (0.130, 0.094) | 54 |
| Ref. 43 | 1-6 | 2-6 | 3.61 | 6.11 | (0.138, 0.082) | 76 |
| Ref. 44 | 1-8 | 2-6 | 3.59 | 6.11 | (0.138, 0.085) | 69 |

TABLE 3-continued

| Luminous Properties of OLEDs | | | | | | |
|---|---|---|---|---|---|---|
| Sample | Dopant | Host | V | EQE (%) | CIE(x,y) | $T_{95}$ (hr) |
| Ref. 45 | 1-11 | 2-6 | 3.61 | 6.11 | (0.141, 0.080) | 85 |
| Ref. 46 | 1-12 | 2-6 | 3.62 | 6.14 | (0.141, 0.080) | 80 |
| Ref. 47 | 1-13 | 2-6 | 3.61 | 6.14 | (0.136, 0.085) | 79 |
| Ref. 48 | 1-17 | 2-6 | 3.62 | 6.15 | (0.136, 0.088) | 76 |

Examples 1-8 (Ex.1-8): Fabrication of OLED

An OLED where the EML includes Compound 2-7 as a host and Compound 1-1 (Ex.1), Compound 1-4 (Ex.2), Compound 1-6 (Ex.3), Compound 1-8 (Ex.4), Compound 1-11 (Ex.5), Compound 1-12 (Ex.6), Compound 1-13 (Ex.7) and Compound 1-17 (Ex.8) in Formula 3 as a dopant, respectively, was fabricated.

Examples 9-16 (Ref.9-16): Fabrication of OLED

An OLED where the EML includes Compound 2-8 as a host and Compound 1-1 (Ex.9), Compound 1-4 (Ex.10), Compound 1-6 (Ex.11), Compound 1-8 (Ex.12), Compound 1-11 (Ex.13), Compound 1-12 (Ex.14), Compound 1-13 (Ex.15) and Compound 1-17 (Ex.16) in Formula 3 as a dopant, respectively, was fabricated.

Experimental Example 4: Measurement of Luminous Properties of OLEDs

Luminous properties for each of the OLEDs fabricated in Examples 1-16 were measured using the same procedure as in Experimental Example 1. The measurement results are indicated in the following Table 4.

TABLE 4

| Luminous Properties of OLEDs | | | | | | |
|---|---|---|---|---|---|---|
| Sample | Dopant | Host | V | EQE (%) | CIE(x,y) | $T_{95}$ (hr) |
| Ex. 1 | 1-1 | 2-7 | 3.98 | 6.28 | (0.140, 0.060) | 95 |
| Ex. 2 | 1-4 | 2-7 | 3.95 | 6.30 | (0.131, 0.089) | 102 |
| Ex. 3 | 1-6 | 2-7 | 3.91 | 6.57 | (0.140, 0.074) | 133 |
| Ex. 4 | 1-8 | 2-7 | 3.88 | 6.59 | (0.137, 0.080) | 123 |
| Ex. 5 | 1-11 | 2-7 | 3.89 | 6.60 | (0.139, 0.074) | 151 |
| Ex. 6 | 1-12 | 2-7 | 3.89 | 6.54 | (0.140, 0.072) | 142 |
| Ex. 7 | 1-13 | 2-7 | 3.90 | 6.62 | (0.137, 0.079) | 141 |
| Ex. 8 | 1-17 | 2-7 | 3.91 | 6.55 | (0.137, 0.079) | 133 |
| Ex. 9 | 1-1 | 2-8 | 4.21 | 6.19 | (0.140, 0.061) | 103 |
| Ex. 10 | 1-4 | 2-8 | 4.20 | 6.20 | (0.131, 0.089) | 111 |
| Ex. 11 | 1-6 | 2-8 | 4.16 | 6.47 | (0.139, 0.074) | 144 |
| Ex. 12 | 1-8 | 2-8 | 4.20 | 6.48 | (0.137, 0.078) | 159 |
| Ex. 13 | 1-11 | 2-8 | 4.20 | 6.45 | (0.140, 0.074) | 165 |
| Ex. 14 | 1-12 | 2-8 | 4.20 | 6.32 | (0.141, 0.073) | 154 |
| Ex. 15 | 1-13 | 2-8 | 4.19 | 6.51 | (0.138, 0.079) | 153 |
| Ex. 16 | 1-17 | 2-8 | 4.20 | 6.33 | (0.137, 0.078) | 144 |

Examples 17-24 (Ex.17-24): Fabrication of OLED

An OLED where the EML includes Compound 2-9 as a host and Compound 1-1 (Ex.17), Compound 1-4 (Ex.18), Compound 1-6 (Ex.19), Compound 1-8 (Ex.20), Compound 1-11 (Ex.21), Compound 1-12 (Ex.22), Compound 1-13 (Ex.23) and Compound 1-17 (Ex.24) in Formula 3 as a dopant, respectively, was fabricated.

Examples 25-32 (Ref.25-32): Fabrication of OLED

An OLED where the EML includes Compound 2-10 as a host and Compound 1-1 (Ex.25), Compound 1-4 (Ex.26), Compound 1-6 (Ex.27), Compound 1-8 (Ex.28), Compound 1-11 (Ex.29), Compound 1-12 (Ex.30), Compound 1-13 (Ex.31) and Compound 1-17 (Ex.32) in Formula 3 as a dopant, respectively, was fabricated.

Experimental Example 5: Measurement of Luminous Properties of OLEDs

Luminous properties for each of the OLEDs fabricated in Examples 17-32 were measured using the same procedure as in Experimental Example 1. The measurement results are indicated in the following Table 5.

TABLE 5

Luminous Properties of OLEDs

| Sample | Dopant | Host | V | EQE (%) | CIE(x,y) | $T_{95}$ (hr) |
|---|---|---|---|---|---|---|
| Ex. 17 | 1-1 | 2-9 | 3.81 | 6.21 | (0.139, 0.062) | 84 |
| Ex. 18 | 1-4 | 2-9 | 3.80 | 6.19 | (0.131, 0.092) | 90 |
| Ex. 19 | 1-6 | 2-9 | 3.79 | 6.42 | (0.137, 0.081) | 120 |
| Ex. 20 | 1-8 | 2-9 | 3.78 | 6.41 | (0.136, 0.084) | 109 |
| Ex. 21 | 1-11 | 2-9 | 3.80 | 6.45 | (0.139, 0.076) | 136 |
| Ex. 22 | 1-12 | 2-9 | 3.81 | 6.42 | (0.139, 0.077) | 126 |
| Ex. 23 | 1-13 | 2-9 | 3.80 | 6.49 | (0.136, 0.084) | 124 |
| Ex. 24 | 1-17 | 2-9 | 3.80 | 6.41 | (0.135, 0.087) | 120 |
| Ex. 25 | 1-1 | 2-10 | 3.80 | 6.21 | (0.139, 0.062) | 84 |
| Ex. 26 | 1-4 | 2-10 | 3.79 | 6.22 | (0.131, 0.092) | 90 |
| Ex. 27 | 1-6 | 2-10 | 3.80 | 6.42 | (0.137, 0.081) | 120 |
| Ex. 28 | 1-8 | 2-10 | 3.79 | 6.41 | (0.136, 0.084) | 109 |
| Ex. 29 | 1-11 | 2-10 | 3.81 | 6.45 | (0.139, 0.076) | 136 |
| Ex. 30 | 1-12 | 2-10 | 3.80 | 6.45 | (0.139, 0.077) | 126 |
| Ex. 31 | 1-13 | 2-10 | 3.79 | 6.49 | (0.136, 0.084) | 124 |
| Ex. 32 | 1-17 | 2-10 | 3.80 | 6.42 | (0.135, 0.087) | 120 |

Examples 33-40 (Ex.33-40): Fabrication of OLED

An OLED where the EML includes Compound 2-11 as a host and Compound 1-1 (Ex.33), Compound 1-4 (Ex.34), Compound 1-6 (Ex.35), Compound 1-8 (Ex.36), Compound 1-11 (Ex.37), Compound 1-12 (Ex.38), Compound 1-13 (Ex.39) and Compound 1-17 (Ex.40) in Formula 3 as a dopant, respectively, was fabricated.

Examples 41-48 (Ref.41-48): Fabrication of OLED

An OLED where the EML includes Compound 2-12 as a host and Compound 1-1 (Ex.41), Compound 1-4 (Ex.42), Compound 1-6 (Ex.43), Compound 1-8 (Ex.44), Compound 1-11 (Ex.45), Compound 1-12 (Ex.46), Compound 1-13 (Ex.47) and Compound 1-17 (Ex.48) in Formula 3 as a dopant, respectively, was fabricated.

Experimental Example 6: Measurement of Luminous Properties of OLEDs

Luminous properties for each of the OLEDs fabricated in Examples 33-48 were measured using the same procedure as in Experimental Example 1. The measurement results are indicated in the following Table 6.

TABLE 6

Luminous Properties of OLEDs

| Sample | Dopant | Host | V | EQE (%) | CIE(x,y) | $T_{95}$ (hr) |
|---|---|---|---|---|---|---|
| Ex. 33 | 1-1 | 2-11 | 3.64 | 6.14 | (0.140, 0.064) | 76 |
| Ex. 34 | 1-4 | 2-11 | 3.62 | 6.11 | (0.130, 0.094) | 82 |
| Ex. 35 | 1-6 | 2-11 | 3.61 | 6.09 | (0.138, 0.082) | 112 |
| Ex. 36 | 1-8 | 2-11 | 3.61 | 6.11 | (0.138, 0.085) | 102 |
| Ex. 37 | 1-11 | 2-11 | 3.61 | 6.11 | (0.141, 0.080) | 129 |
| Ex. 38 | 1-12 | 2-11 | 3.62 | 6.14 | (0.141, 0.080) | 119 |
| Ex. 39 | 1-13 | 2-11 | 3.63 | 6.13 | (0.136, 0.085) | 117 |
| Ex. 40 | 1-17 | 2-11 | 3.64 | 6.15 | (0.136, 0.088) | 112 |
| Ex. 41 | 1-1 | 2-12 | 3.64 | 6.15 | (0.140, 0.064) | 75 |
| Ex. 42 | 1-4 | 2-12 | 3.61 | 6.14 | (0.130, 0.094) | 81 |
| Ex. 43 | 1-6 | 2-12 | 3.60 | 6.12 | (0.138, 0.082) | 114 |
| Ex. 44 | 1-8 | 2-12 | 3.58 | 6.12 | (0.138, 0.085) | 103 |
| Ex. 45 | 1-11 | 2-12 | 3.60 | 6.12 | (0.141, 0.080) | 127 |
| Ex. 46 | 1-12 | 2-12 | 3.61 | 6.13 | (0.141, 0.080) | 120 |
| Ex. 47 | 1-13 | 2-12 | 3.60 | 6.15 | (0.136, 0.085) | 118 |
| Ex. 48 | 1-17 | 2-12 | 3.61 | 6.14 | (0.136, 0.088) | 114 |

Summarizing the results in Tables 1 to 6, compared to the OLEDs fabricated in Ref.1 to Ref.48 where the EML includes a non-deuterated anthracene-based compound (Compounds 2-1 to Compound 2-6) as the host, the OLEDs fabricated in Ex.1 to Ex.48 where the EML includes a deuterated anthracene-based compound (Compounds 2-7 to Compound 2-12) as the host improved their luminous efficiency and luminous lifespan.

In addition, compared to the OLEDs fabricated in Ex.17-48, the OLEDs fabricated in Ex.1-8 where the EML includes the Compound 2-7 as the host and the OLEDs fabricated in Ex. 9-16 wherein the EML includes the Compound 2-9 as the host improved their luminous efficiency and luminous lifespan. In other words, when the anthracene-based compound, where a naphthyl moiety (1-naphthyl) is linked directly to one side of an anthracene moiety and other naphthyl moiety (2-naphthyl) is linked directly or via a bridging group (linker) to the other side of the anthracene moiety and is deuterated, are used as the host in the EML, the luminous efficiency and the luminous lifespan of the OLEDs are further increased.

Also, compared to the OLEDs fabricated in Ex.1-8 where the EML includes the Compound 2-7 as the host, the OLEDs fabricated in Ex.9-16 where the EML includes the Compound 2-8 as the host showed sufficient luminous lifespan. On the contrary, the OLEDs where the EML includes the Compound 2-7 as the host lowered their driving voltages. In other words, the OLEDs where the EML includes the anthracene-based compound, where a naphthyl moiety (1-naphthyl) is linked to directly to one side of the anthracene moiety and the other naphthyl moiety (2-naphthyl) is linked directly or via the bridging group and is deuterated, lowered its driving voltage and improved their luminous efficiency and luminous lifespan.

Also, compared to the OLEDs where the EML includes the boron-based compound having symmetrical chemical structure (Compounds 1-1 and 1-4) as the dopant, the OLEDs where the EML includes the boron-based compound having asymmetrical chemical structure (Compounds 1-6 and 1-8) as the dopant improved their luminous efficiency and luminous lifespan.

In addition, the OLEDs where the EML includes the boron-based compound which is deuterated and having the asymmetric structure (Compounds, 1-11, 1-12, 1-13 and 1-17) as the dopant enhanced their luminous efficiency and luminous lifespan further. Particularly, when the HIL and the HTL includes the compound in Formula 11 and the EBL includes the amine-based compound of Formula 5, the OLED can improve its luminous properties.

Fabrication of Organic Light Emitting Diode (OLED) 2

A glass substrate (40 mm×40 mm×0.5 mm) onto which ITO was coated as a thin film was washed and ultrasonically cleaned by solvent such as isopropyl alcohol, acetone and distilled water for 5 minutes and dried at 100° C. oven. After cleaning the substrate, the substrate was treated with $O_2$ plasma under vacuum for 2 minutes and then transferred to a vacuum chamber for depositing emission layer. Subsequently, an emissive layer and a cathode were deposited by evaporation from a heating boat under about 5~7×$10^{-7}$ Torr with a deposition rate of 1 Å/s as the following order:

An HIL (Formula 11 (97 wt %) and Formula 12 (3 wt %), 100 Å); an HTL (Formula 11, 100 Å); an EBL (100 Å); an EML (Host (H, 98 wt %) and Dopant (D, 2 wt %), 200 Å); an HBL (100 Å); an EIL (Formula 13 (98 wt %), Li (2 wt %), 200 Å); and a cathode (Al, 500 Å).

And then, the OLED was encapsulated with UV-curable epoxy and moisture getter.

Comparative Example 49 (Ref.49): Fabrication of OLED

An OLED where the EBL includes the following Ref.EBL, the EML includes Compound 1-1 (dopant) in Formula 2 and Compound 2-1 (host) and the HBL includes the following Ref.HBL was fabricated.

Examples 49-56 (Ex.49-56): Fabrication of OLEDs

An OLED where the EML includes the Compound 1-1 (dopant) in Formula 2 and Compound 2-7 (host) in Formula 4, the EBL includes the following Ref.EBL (Ex.49-51), H4 in Formula 6 (Ex.52-54) or H3 in Formula 6 (Ex.55-57), and the HBL includes the following Ref.HBL (Ex.49, 52 and 55), E1 in Formula 8 (Ex.50, 53 and 56) or F1 in Formula 10 (Ex.51, 54 and 57), respectively, were fabricated.

[Reference Compounds]

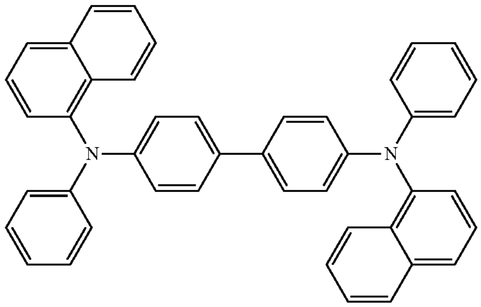

Ref. EBL

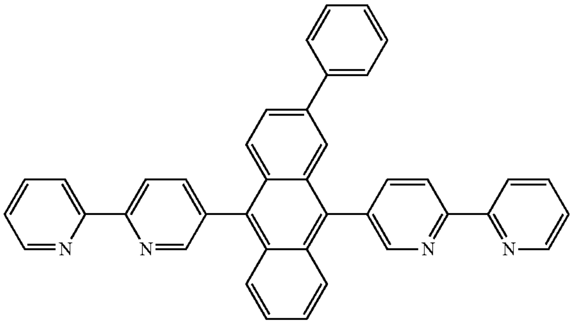

Ref. HBL

Experimental Example 7: Measurement of Luminous Properties of OLEDs

Luminous properties for each of the OLEDs fabricated in Examples 49-57 and Comparative Example 49 were measured using the same procedure as in Experimental Example 1. The measurement results are indicated in the following Table 7.

TABLE 7

Luminous Properties of OLEDs

| Sample | EBL | D | H | HBL | V | EQE (%) | CIE(x) | CIE(y) | $T_{95}$ (hr) |
|---|---|---|---|---|---|---|---|---|---|
| Ref. 49 | Ref. | 1-1 | 2-1 | Ref. | 4.00 | 3.00 | 0.140 | 0.063 | 22 |
| Ex. 49 | Ref. | 1-1 | 2-7 | Ref. | 4.02 | 2.97 | 0.140 | 0.062 | 30 |
| Ex. 50 | Ref. | 1-1 | 2-7 | E1 | 4.01 | 2.99 | 0.140 | 0.061 | 38 |
| Ex. 51 | Ref. | 1-1 | 2-7 | F1 | 3.96 | 3.04 | 0.140 | 0.060 | 46 |
| Ex. 52 | H4 | 1-1 | 2-7 | Ref. | 4.01 | 5.85 | 0.139 | 0.060 | 87 |
| Ex. 53 | H4 | 1-1 | 2-7 | E1 | 3.98 | 5.99 | 0.140 | 0.060 | 115 |
| Ex. 54 | H4 | 1-1 | 2-7 | F1 | 3.98 | 6.17 | 0.140 | 0.060 | 133 |
| Ex. 55 | H3 | 1-1 | 2-7 | Ref. | 4.01 | 6.20 | 0.139 | 0.62 | 85 |
| Ex. 56 | H3 | 1-1 | 2-7 | E1 | 4.00 | 6.31 | 0.141 | 0.059 | 114 |
| Ex. 57 | H3 | 1-1 | 2-7 | F1 | 3.96 | 6.48 | 0.141 | 0.060 | 124 |

Comparative Example 50 (Ref.50): Fabrication of OLED

An OLED where the EBL includes the Ref.EBL, the EML includes Compound 1-1 (dopant) in Formula 2 and Compound 2-3 (host) and the HBL includes the Ref.HBL was fabricated.

Examples 58-66 (Ex.58-66): Fabrication of OLEDs

An OLED where the EML includes the Compound 1-1 (dopant) in Formula 2 and Compound 2-9 (host) in Formula 4, the EBL includes the Ref.EBL (Ex.58-60), H4 in Formula 6 (Ex.61-63) or H3 in Formula 6 (Ex.64-66), respectively, and the HBL includes the Ref.HBL (Ex.58, 61 and 64), E1 in Formula 8 (Ex.59, 62 and 65) or F1 in Formula 10 (Ex.60, 63 and 66), respectively, were fabricated.

Experimental Example 8: Measurement of Luminous Properties of OLEDs

Luminous properties for each of the OLEDs fabricated in Examples 58-66 and Comparative Example 50 were measured using the same procedure as in Experimental Example 1. The measurement results are indicated in the following Table 8.

TABLE 8

Luminous Properties of OLEDs

| Sample | EBL | D | H | HBL | V | EQE (%) | CIE(x) | CIE(y) | $T_{95}$ (hr) |
|---|---|---|---|---|---|---|---|---|---|
| Ref 50 | Ref. | 1-1 | 2-3 | Ref. | 3.86 | 2.92 | 0.139 | 0.064 | 21 |
| Ex. 58 | Ref. | 1-1 | 2-9 | Ref. | 3.87 | 2.93 | 0.140 | 0.063 | 28 |
| Ex. 59 | Ref. | 1-1 | 2-9 | E1 | 3.83 | 2.98 | 0.139 | 0.062 | 36 |
| Ex. 60 | Ref. | 1-1 | 2-9 | F1 | 3.90 | 3.08 | 0.141 | 0.062 | 39 |
| Ex. 61 | H4 | 1-1 | 2-9 | Ref. | 3.86 | 5.81 | 0.140 | 0.063 | 83 |
| Ex. 62 | H4 | 1-1 | 2-9 | E1 | 3.81 | 5.93 | 0.139 | 0.062 | 102 |
| Ex. 63 | H4 | 1-1 | 2-9 | F1 | 3.90 | 6.11 | 0.140 | 0.063 | 116 |
| Ex. 64 | H3 | 1-1 | 2-9 | Ref. | 3.89 | 6.15 | 0.139 | 0.064 | 79 |
| Ex. 65 | H3 | 1-1 | 2-9 | E1 | 3.82 | 6.22 | 0.139 | 0.062 | 97 |
| Ex. 66 | H3 | 1-1 | 2-9 | F1 | 3.89 | 6.41 | 0.140 | 0.061 | 115 |

Comparative Example 51 (Ref.51): Fabrication of OLED

An OLED where the EBL includes the Ref.EBL, the EML includes Compound 1-4 (dopant) in Formula 2 and Compound 2-1 (host) and the HBL includes the Ref.HBL was fabricated.

Examples 67-75 (Ex.67-75): Fabrication of OLEDs

An OLED where the EML includes the Compound 1-4 (dopant) in Formula 2 and Compound 2-7 (host) in Formula 4, the EBL includes the Ref.EBL (Ex.67-69), H4 in Formula 6 (Ex.70-72) or H3 in Formula 6 (Ex.73-75), respectively, and the HBL includes the Ref.HBL (Ex.67, 70 and 73), E1 in Formula 8 (Ex.68, 71 and 74) or F1 in Formula 10 (Ex.69, 72 and 75), respectively, were fabricated.

Experimental Example 9: Measurement of Luminous Properties of OLEDs

Luminous properties for each of the OLEDs fabricated in Examples 67-75 and Comparative Example 51 were measured using the same procedure as in Experimental Example 1. The measurement results are indicated in the following Table 9.

TABLE 9

Luminous Properties of OLEDs

| Sample | EBL | D | H | HBL | V | EQE (%) | CIE(x) | CIE(y) | $T_{95}$ (hr) |
|---|---|---|---|---|---|---|---|---|---|
| Ref. 51 | Ref. | 1-4 | 2-1 | Ref. | 3.99 | 2.95 | 0.132 | 0.062 | 23 |
| Ex. 67 | Ref. | 1-4 | 2-7 | Ref. | 4.00 | 2.96 | 0.131 | 0.091 | 34 |
| Ex. 68 | Ref. | 1-4 | 2-7 | E1 | 3.92 | 3.01 | 0.132 | 0.090 | 44 |
| Ex. 69 | Ref. | 1-4 | 2-7 | F1 | 3.92 | 3.10 | 0.130 | 0.090 | 49 |
| Ex. 70 | H4 | 1-4 | 2-7 | Ref. | 3.99 | 5.88 | 0.131 | 0.090 | 92 |
| Ex. 71 | H4 | 1-4 | 2-7 | E1 | 3.95 | 6.01 | 0.131 | 0.089 | 123 |
| Ex. 72 | H4 | 1-4 | 2-7 | F1 | 3.95 | 6.19 | 0.130 | 0.090 | 148 |

TABLE 9-continued

| Luminous Properties of OLEDs | | | | | | | | | |
|---|---|---|---|---|---|---|---|---|---|
| Sample | EBL | D | H | HBL | V | EQE (%) | CIE(x) | CIE(y) | $T_{95}$ (hr) |
| Ex. 73 | H3 | 1-4 | 2-7 | Ref. | 3.95 | 6.18 | 0.131 | 0.090 | 88 |
| Ex. 74 | H3 | 1-4 | 2-7 | E1 | 3.97 | 6.31 | 0.130 | 0.090 | 121 |
| Ex. 75 | H3 | 1-4 | 2-7 | F1 | 3.92 | 6.55 | 0.130 | 0.089 | 138 |

Comparative Example 52 (Ref.52): Fabrication of OLED

An OLED where the EBL includes the Ref.EBL, the EML includes Compound 1-4 (dopant) in Formula 2 and Compound 2-3 (host) and the HBL includes the Ref.HBL was fabricated.

Examples 76-84 (Ex.76-84): Fabrication of OLEDs

An OLED where the EML includes the Compound 1-4 (dopant) in Formula 2 and Compound 2-9 (host) in Formula 4, the EBL includes the Ref.EBL (Ex.76-78), H4 in Formula 6 (Ex.79-81) or H3 in Formula 6 (Ex.82-84), respectively, and the HBL includes the Ref.HBL (Ex.76, 79 and 82), E1 in Formula 8 (Ex.77, 80 and 83) or F1 in Formula 10 (Ex.78, 81 and 84), respectively, were fabricated.

Experimental Example 10: Measurement of Luminous Properties of OLEDs

Luminous properties for each of the OLEDs fabricated in Examples 76-84 and Comparative Example 52 were measured using the same procedure as in Experimental Example 1. The measurement results are indicated in the following Table 10.

TABLE 10

| Luminous Properties of OLEDs | | | | | | | | | |
|---|---|---|---|---|---|---|---|---|---|
| Sample | EBL | D | H | HBL | V | EQE (%) | CIE(x) | CIE(y) | $T_{95}$ (hr) |
| Ref. 52 | Ref. | 1-4 | 2-3 | Ref. | 3.82 | 2.89 | 0.131 | 0.092 | 20 |
| Ex. 76 | Ref. | 1-4 | 2-9 | Ref. | 3.87 | 2.89 | 0.131 | 0.092 | 29 |
| Ex. 77 | Ref. | 1-4 | 2-9 | E1 | 3.80 | 2.97 | 0.131 | 0.091 | 36 |
| Ex. 78 | Ref. | 1-4 | 2-9 | F1 | 3.87 | 3.08 | 0.132 | 0.091 | 44 |
| Ex. 79 | H4 | 1-4 | 2-9 | Ref. | 3.85 | 5.77 | 0.130 | 0.092 | 84 |
| Ex. 80 | H4 | 1-4 | 2-9 | E1 | 3.80 | 5.91 | 0.131 | 0.092 | 109 |
| Ex. 81 | H4 | 1-4 | 2-9 | F1 | 3.82 | 6.09 | 0.131 | 0.091 | 133 |
| Ex. 82 | H3 | 1-4 | 2-9 | Ref. | 3.85 | 6.09 | 0.131 | 0.091 | 83 |
| Ex. 83 | H3 | 1-4 | 2-9 | E1 | 3.77 | 6.23 | 0.131 | 0.092 | 110 |
| Ex. 84 | H3 | 1-4 | 2-9 | F1 | 3.85 | 6.39 | 0.130 | 0.092 | 131 |

Comparative Example 53 (Ref.53): Fabrication of OLED

An OLED where the EBL includes the Ref.EBL, the EML includes Compound 1-6 (dopant) in Formula 2 and Compound 2-1 (host) and the HBL includes the Ref.HBL was fabricated.

Examples 85-93 (Ex.85-93): Fabrication of OLEDs

An OLED where the EML includes the Compound 1-6 (dopant) in Formula 2 and Compound 2-7 (host) in Formula 4, the EBL includes the Ref.EBL (Ex.85-87), H4 in Formula 6 (Ex.88-90) or H3 in Formula 6 (Ex.91-93), respectively, and the HBL includes the Ref.HBL (Ex.85, 88 and 91), E1 in Formula 8 (Ex.86, 89 and 92) or F1 in Formula 10 (Ex.87, 90 and 93), respectively, were fabricated.

Experimental Example 11: Measurement of Luminous Properties of OLEDs

Luminous properties for each of the OLEDs fabricated in Examples 85-93 and Comparative Example 53 were measured using the same procedure as in Experimental Example 1. The measurement results are indicated in the following Table 11.

TABLE 11

| Luminous Properties of OLEDs | | | | | | | | | |
|---|---|---|---|---|---|---|---|---|---|
| Sample | EBL | D | H | HBL | V | EQE (%) | CIE(x) | CIE(y) | $T_{95}$ (hr) |
| Ref. 53 | Ref. | 1-6 | 2-1 | Ref. | 3.93 | 3.11 | 0.140 | 0.076 | 26 |
| Ex. 85 | Ref. | 1-6 | 2-7 | Ref. | 3.95 | 3.09 | 0.140 | 0.075 | 45 |
| Ex. 86 | Ref. | 1-6 | 2-7 | E1 | 3.95 | 3.14 | 0.141 | 0.074 | 54 |
| Ex. 87 | Ref. | 1-6 | 2-7 | F1 | 3.91 | 3.19 | 0.140 | 0.075 | 61 |
| Ex. 88 | H4 | 1-6 | 2-7 | Ref. | 3.96 | 6.13 | 0.140 | 0.076 | 122 |
| Ex. 89 | H4 | 1-6 | 2-7 | E1 | 3.91 | 6.27 | 0.140 | 0.074 | 161 |
| Ex. 90 | H4 | 1-6 | 2-7 | F1 | 3.91 | 6.38 | 0.140 | 0.074 | 190 |
| Ex. 91 | H3 | 1-6 | 2-7 | Ref. | 3.93 | 6.45 | 0.139 | 0.077 | 110 |
| Ex. 92 | H3 | 1-6 | 2-7 | E1 | 3.92 | 6.58 | 0.140 | 0.074 | 150 |
| Ex. 93 | H3 | 1-6 | 2-7 | F1 | 3.92 | 6.70 | 0.140 | 0.074 | 177 |

Comparative Example 54 (Ref.54): Fabrication of OLED

An OLED where the EBL includes the Ref.EBL, the EML includes Compound 1-6 (dopant) in Formula 2 and Compound 2-3 (host) and the HBL includes the Ref.HBL was fabricated.

Examples: 94-102 (Ex.94-102): Fabrication of OLEDs

An OLED where the EML includes the Compound 1-6 (dopant) in Formula 2 and Compound 2-9 (host) in Formula 4, the EBL includes the Ref.EBL (Ex.94-96), H4 in Formula 6 (Ex.97-99) or H3 in Formula 6 (Ex.100-102), respectively, and the HBL includes the Ref.HBL (Ex.94, 97 and 100), E1 in Formula 8 (Ex.95, 98 and 101) or F1 in Formula 10 (Ex.96, 99 and 102), respectively, were fabricated.

Experimental Example 12: Measurement of Luminous Properties of OLEDs

Luminous properties for each of the OLEDs fabricated in Examples 94-102 and Comparative Example 54 were measured using the same procedure as in Experimental Example 1. The measurement results are indicated in the following Table 12.

TABLE 12

| Luminous Properties of OLEDs | | | | | | | | | |
|---|---|---|---|---|---|---|---|---|---|
| Sample | EBL | D | H | HBL | V | EQE (%) | CIE(x) | CIE(y) | $T_{95}$ (hr) |
| Ref. 54 | Ref. | 1-6 | 2-3 | Ref. | 3.82 | 3.01 | 0.139 | 0.076 | 28 |
| Ex. 94 | Ref. | 1-6 | 2-9 | Ref. | 3.84 | 3.03 | 0.138 | 0.081 | 38 |
| Ex. 95 | Ref. | 1-6 | 2-9 | E1 | 3.81 | 3.09 | 0.137 | 0.080 | 49 |
| Ex. 96 | Ref. | 1-6 | 2-9 | F1 | 3.82 | 3.19 | 0.138 | 0.081 | 58 |
| Ex. 97 | H4 | 1-6 | 2-9 | Ref. | 3.85 | 6.05 | 0.138 | 0.081 | 112 |
| Ex. 98 | H4 | 1-6 | 2-9 | E1 | 3.79 | 6.13 | 0.137 | 0.081 | 145 |
| Ex. 99 | H4 | 1-6 | 2-9 | F1 | 3.80 | 6.31 | 0.137 | 0.082 | 174 |
| Ex. 100 | H3 | 1-6 | 2-9 | Ref. | 3.83 | 6.36 | 0.138 | 0.081 | 106 |
| Ex. 101 | H3 | 1-6 | 2-9 | E1 | 3.79 | 6.41 | 0.138 | 0.079 | 136 |
| Ex. 102 | H3 | 1-6 | 2-9 | F1 | 3.80 | 6.60 | 0.137 | 0.082 | 169 |

Comparative Example 55 (Ref.55): Fabrication of OLED

An OLED where the EBL includes the Ref.EBL, the EML includes Compound 1-8 (dopant) in Formula 2 and Compound 2-1 (host) and the HBL includes the Ref.HBL was fabricated.

Examples: 103-111 (Ex.103-111): Fabrication of OLEDs

An OLED where the EML includes the Compound 1-8 (dopant) in Formula 2 and Compound 2-7 (host) in Formula 4, the EBL includes the Ref.EBL (Ex.103-105), H4 in Formula 6 (Ex.106-108) or H3 in Formula 6 (Ex.109-111), respectively, and the HBL includes the Ref.HBL (Ex.103, 106 and 109), E1 in Formula 8 (Ex.104, 107 and 110) or F1 in Formula 10 (Ex.105, 108 and 111), respectively, were fabricated.

Experimental Example 13: Measurement of Luminous Properties of OLEDs

Luminous properties for each of the OLEDs fabricated in Examples 103-111 and Comparative Example 55 were measured using the same procedure as in Experimental Example 1. The measurement results are indicated in the following Table 13.

TABLE 13

Luminous Properties of OLEDs

| Sample | EBL | D | H | HBL | V | EQE (%) | CIE(x) | CIE(y) | $T_{95}$ (hr) |
|---|---|---|---|---|---|---|---|---|---|
| Ref. 55 | Ref. | 1-8 | 2-1 | Ref. | 3.92 | 3.12 | 0.136 | 0.081 | 28 |
| Ex. 103 | Ref. | 1-8 | 2-7 | Ref. | 3.93 | 3.08 | 0.139 | 0.082 | 42 |
| Ex. 104 | Ref. | 1-8 | 2-7 | E1 | 3.87 | 3.17 | 0.137 | 0.081 | 50 |
| Ex. 105 | Ref. | 1-8 | 2-7 | F1 | 3.91 | 3.22 | 0.137 | 0.082 | 59 |
| Ex. 106 | H4 | 1-8 | 2-7 | Ref. | 3.92 | 6.17 | 0.138 | 0.081 | 119 |
| Ex. 107 | H4 | 1-8 | 2-7 | E1 | 3.88 | 6.29 | 0.137 | 0.080 | 149 |
| Ex. 108 | H4 | 1-8 | 2-7 | F1 | 3.89 | 6.44 | 0.137 | 0.081 | 175 |
| Ex. 109 | H3 | 1-8 | 2-7 | Ref. | 3.90 | 6.48 | 0.138 | 0.081 | 118 |
| Ex. 110 | H3 | 1-8 | 2-7 | E1 | 3.88 | 6.67 | 0.138 | 0.081 | 142 |
| Ex. 111 | H3 | 1-8 | 2-7 | F1 | 3.89 | 6.72 | 0.136 | 0.082 | 167 |

Comparative Example 56 (Ref.56): Fabrication of OLED

An OLED where the EBL includes the Ref.EBL, the EML includes Compound 1-8 (dopant) in Formula 2 and Compound 2-3 (host) and the HBL includes the Ref.HBL was fabricated.

Examples: 112-120 (Ex.112-120): Fabrication of OLEDs

An OLED where the EML includes the Compound 1-8 (dopant) in Formula 2 and Compound 2-9 (host) in Formula 4, the EBL includes the Ref.EBL (Ex.112-114), H4 in Formula 6 (Ex.115-117) or H3 in Formula 6 (Ex.118-120), respectively, and the HBL includes the Ref.HBL (Ex.112, 115 and 118), E1 in Formula 8 (Ex.113, 116 and 119) or F1 in Formula 10 (Ex.114, 117 and 120), respectively, were fabricated.

Experimental Example 14: Measurement of Luminous Properties of OLEDs

Luminous properties for each of the OLEDs fabricated in Examples 112-120 and Comparative Example 56 were measured using the same procedure as in Experimental Example 1. The measurement results are indicated in the following Table 14.

TABLE 14

Luminous Properties of OLEDs

| Sample | EBL | D | H | HBL | V | EQE (%) | CIE(x) | CIE(y) | $T_{95}$ (hr) |
|---|---|---|---|---|---|---|---|---|---|
| Ref. 56 | Ref. | 1-8 | 2-3 | Ref. | 3.80 | 3.05 | 0.137 | 0.081 | 27 |
| Ex. 112 | Ref. | 1-8 | 2-9 | Ref. | 3.81 | 3.07 | 0.138 | 0.083 | 36 |
| Ex. 113 | Ref. | 1-8 | 2-9 | E1 | 3.76 | 3.06 | 0.137 | 0.083 | 42 |

TABLE 14-continued

| Luminous Properties of OLEDs | | | | | | | | | |
|---|---|---|---|---|---|---|---|---|---|
| Sample | EBL | D | H | HBL | V | EQE (%) | CIE(x) | CIE(y) | $T_{95}$ (hr) |
| Ex. 114 | Ref. | 1-8 | 2-9 | F1 | 3.80 | 3.18 | 0.137 | 0.083 | 52 |
| Ex. 115 | H4 | 1-8 | 2-9 | Ref. | 3.82 | 6.05 | 0.137 | 0.083 | 107 |
| Ex. 116 | H4 | 1-8 | 2-9 | E1 | 3.78 | 6.12 | 0.136 | 0.084 | 132 |
| Ex. 117 | H4 | 1-8 | 2-9 | F1 | 3.79 | 6.30 | 0.136 | 0.084 | 156 |
| Ex. 118 | H3 | 1-8 | 2-9 | Ref. | 3.84 | 6.38 | 0.137 | 0.083 | 102 |
| Ex. 119 | H3 | 1-8 | 2-9 | E1 | 3.76 | 6.42 | 0.136 | 0.084 | 129 |
| Ex. 120 | H3 | 1-8 | 2-9 | F1 | 3.81 | 6.62 | 0.136 | 0.083 | 144 |

Summarizing the results in Tables 7 to 14, compared to the OLEDs fabricated in Ref.49 to Ref.56 where the EML includes a non-deuterated anthracene-based compound (Compound 2-1 or Compound 2-3) as the host, the OLEDs fabricated in Ex.49 to Ex.120 where the EML includes a deuterated anthracene-based compound (Compound 2-7 or Compound 2-9) as the host improved luminous efficiency and luminous lifespan.

In addition, compared to the OLEDs fabricated in Ex.58-66, 76-84, 94-102 and 112-120 where the EML includes the Compound 2-9 as the host, the OLEDs fabricated in Ex.49-57, 67-75, 85-93 and 103-111 where the EML includes the Compound 2-7 as the host improved their luminous efficiency and luminous lifespan. In other words, when the anthracene-based compound, where a naphthyl moiety (1-naphthyl) is linked directly to one side of an anthracene moiety and other naphthyl moiety (2-naphthyl) is linked directly or via a bridging group (linker) to the other side of the anthracene moiety and is deuterated, are used as the host in the EML, the luminous efficiency and the luminous lifespan of the OLEDs are further increased.

Also, when the boron-based compound (Compound 1-6 or Compound 1-8) having an asymmetric chemical structure was used as the dopant in the EML, the luminous efficiency and the luminous lifespan of the OLEDs are further improved. Particularly, when the Compound 1-6 ($R_{91}$ is alkyl (tert-butyl), each of $R_{81}$ and $R_{82}$ is aryl (phenyl) substituted with alkyl (tert-butyl) in Formula 1B), is used as the dopant in the EML, the luminous efficiency and the luminous lifespan of the OLEDs are improved significantly.

Moreover, when the HBL includes the azine-based compound of Formula 8 or the benzimidazole-based compound of Formula 10, the OLEDs showed very excellent luminous efficiency and luminous lifespan. Also, when the HBL includes the amine-based compound of Formula 6, the luminous efficiency and the luminous lifespan of the OLED can be maximized.

In addition, when the EML includes the deuterated anthracene-based compound (Compound 2-7 or Compound 2-9) and the boron-based compound of Formula 1B, the EBL includes the amine-based compound of Formula 5 and the HBL includes the azine-based compound of Formula 7 or the benzimidazole-based compound of Formula 9, the luminous efficiency and the luminous lifespan of the OLED are remarkably improved.

It will be apparent to those skilled in the art that various modifications and variations can be made in the organic light emitting device of the present disclosure without departing from the scope of the disclosure. Thus, it is intended that the present disclosure cover the modifications and variations of the present disclosure provided they come within the scope of the appended claims.

What is claimed is:

1. An organic light emitting device, comprising:

a substrate; and an organic light emitting diode over the substrate, the organic light emitting diode including a first electrode, a second electrode facing the first electrode and an emissive layer disposed between the first electrode and the second electrode, wherein the emissive layer comprises a first emitting material layer including a first dopant and a first host, a first electron blocking layer disposed between the first electrode and the first emitting material layer and a first hole blocking layer disposed between the first emitting material layer and the second electrode, wherein the first emitting material layer emits blue light, wherein the first dopant includes a boron-based compound selected from the group consisting of:

1-5

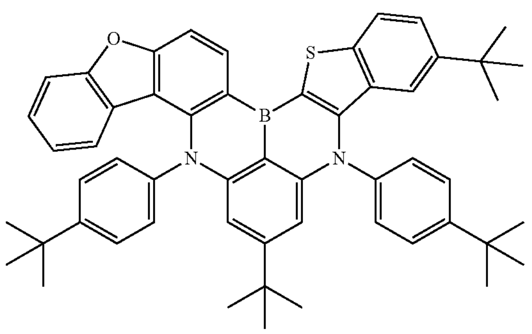

1-6

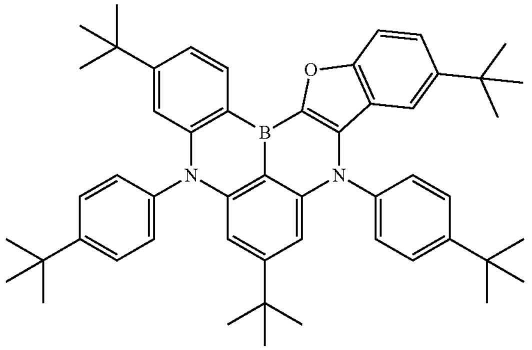

-continued
1-7
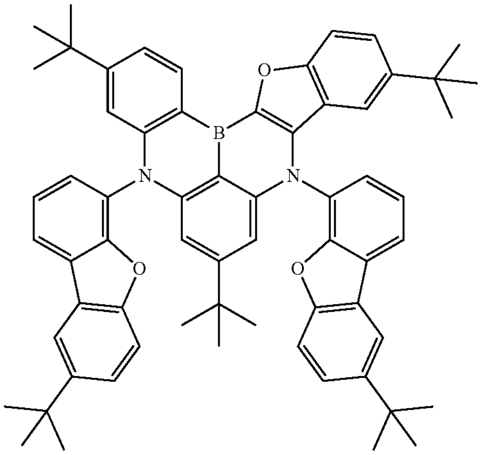
1-8
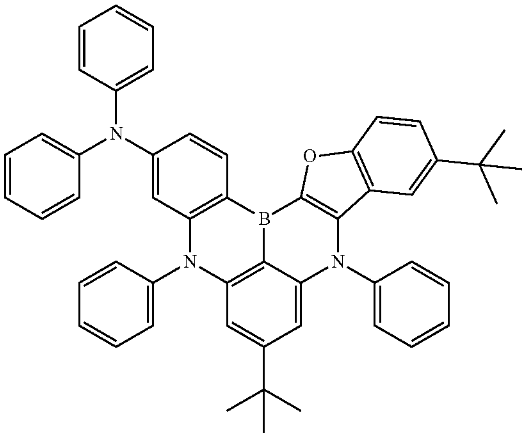
1-9
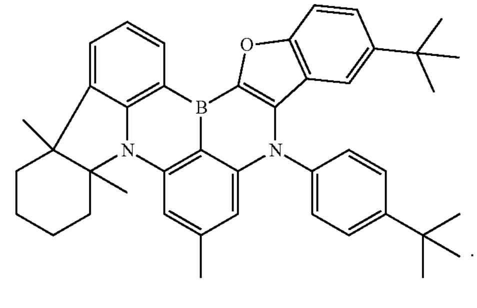
1-10
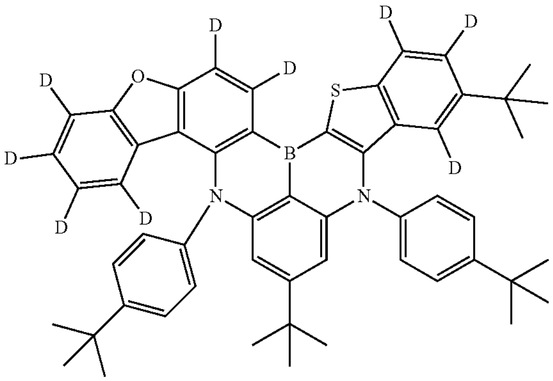
1-11
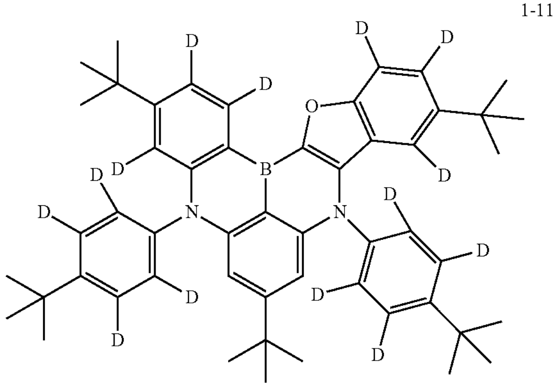
1-12
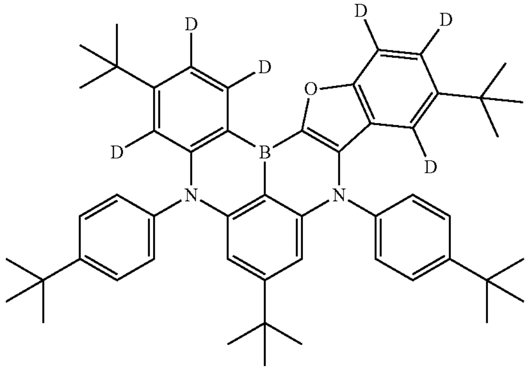
1-13
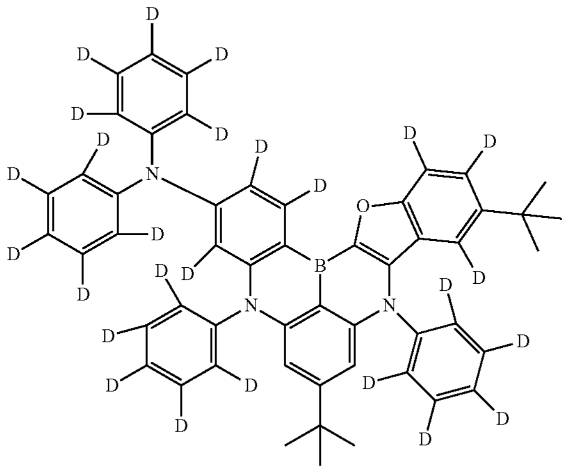

-continued 1-14

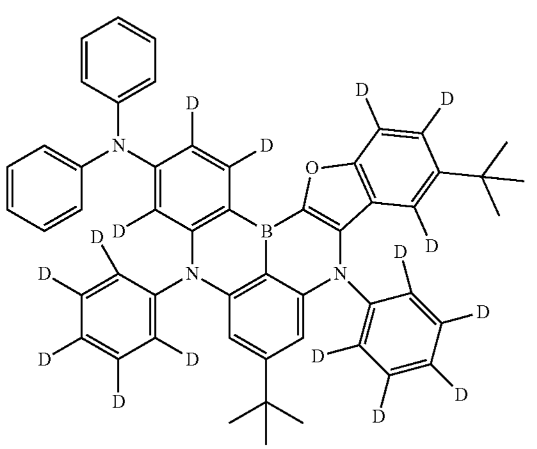

1-15

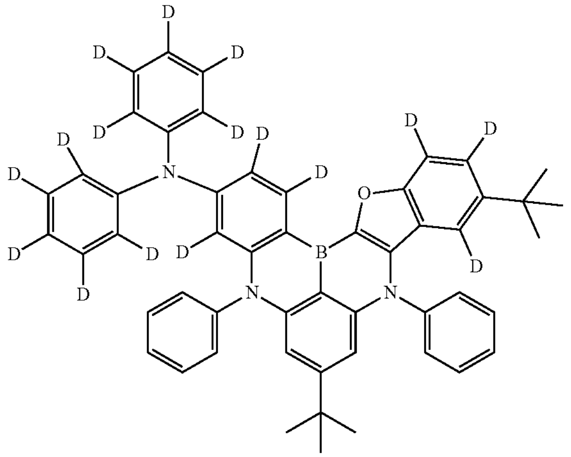

1-16

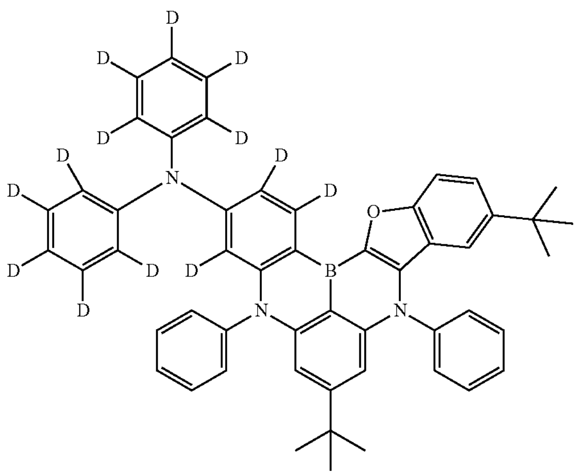

-continued 1-17

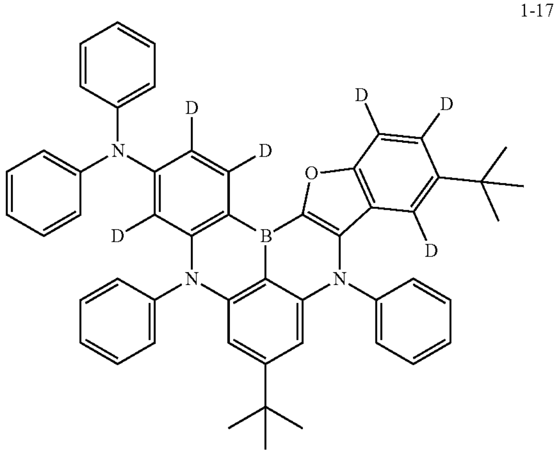

wherein the first host includes an anthracene-based compound having the following structure of Formula 3, wherein the first electron blocking layer includes an amine-based compound having the following structure of Formula 5:

[Formula 3]

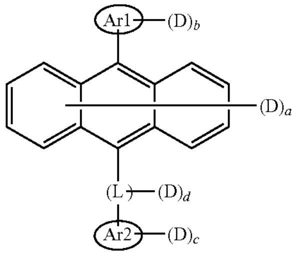

wherein each of Ar1 and Ar2 is independently a $C_6$-$C_{30}$ aryl group or a $C_5$-$C_{30}$ hetero aryl group; L is a single bond, a $C_6$-$C_{20}$ arylene group or a $C_5$-$C_{20}$ hetero arylene group; a is an integer of 0 to 8; each of b, c and d is independently an integer of 0 to 30, wherein at least one of a, b, c and d is a positive integer;

[Formula 5]

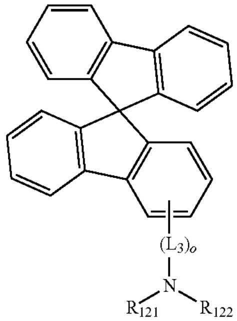

wherein $L_3$ is $C_6$-$C_{30}$ arylene; o is 0 or 1; each of $R_{121}$ and $R_{122}$ is independently $C_6$-$C_{30}$ aryl or $C_5$-$C_{30}$ hetero aryl, wherein each of the $C_6$-$C_{30}$ aryl and the $C_5$-$C_{30}$ hetero aryl is independently unsubstituted or substituted with at least one of $C_1$-$C_{10}$ alkyl and $C_6$-$C_{30}$ aryl, wherein the first hole blocking layer includes an azine-based compound, wherein the azine-based compound includes a compound that is selected from the group consisting of: (i) compound E15, (ii) compound E16, (iii) compound E17, (iv) compound E18, and (v) any combination of (i) to (iv):

E15

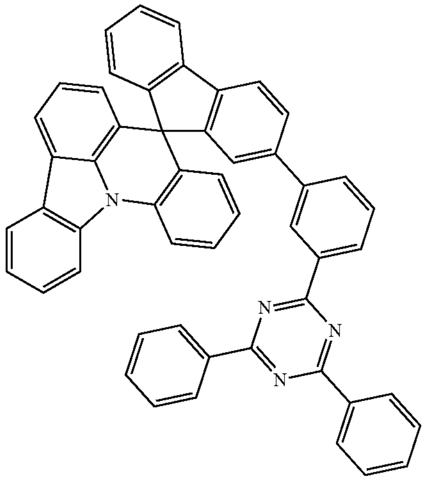

E16

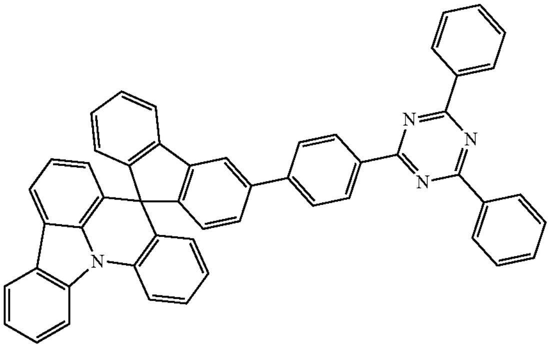

-continued

E17

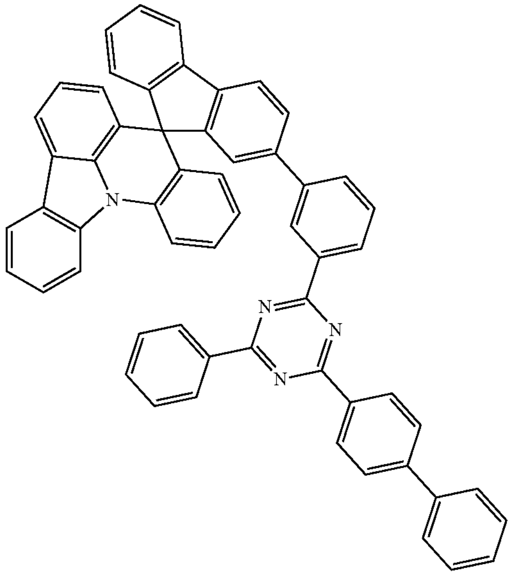

E18

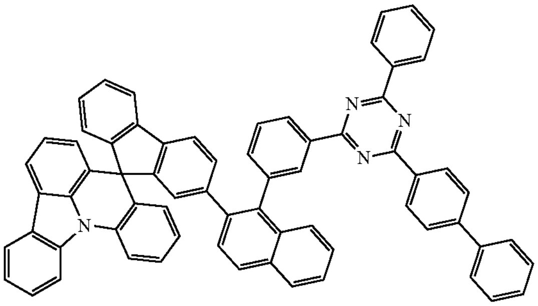

.

2. The organic light emitting device of claim 1, wherein the first host is selected from the following anthracene-based compounds:

2-7

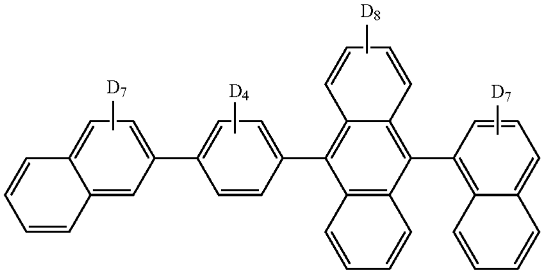

2-8

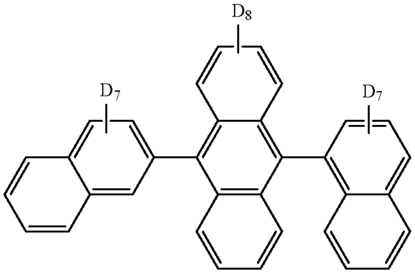

-continued
2-9
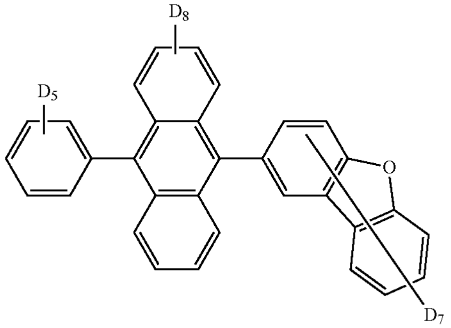
2-10
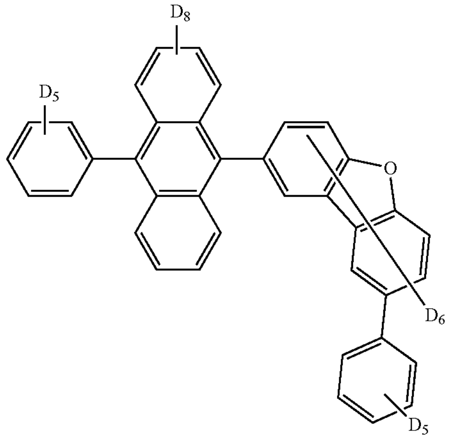
2-11
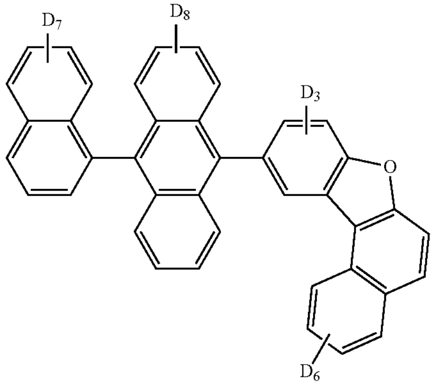
2-12
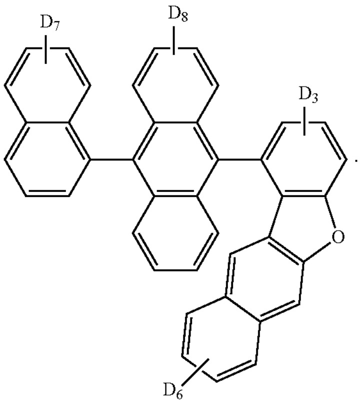
3. The organic light emitting device of claim 1, wherein the amine-based compound is selected from the following amine-based compounds:
H1
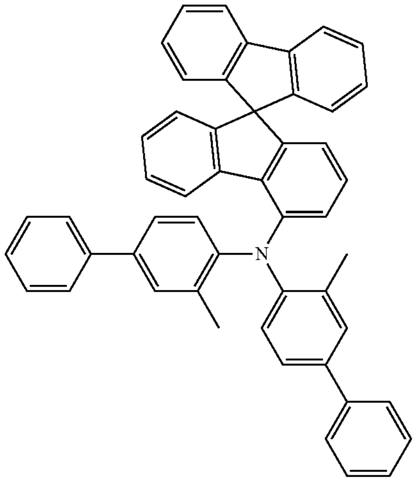
H2
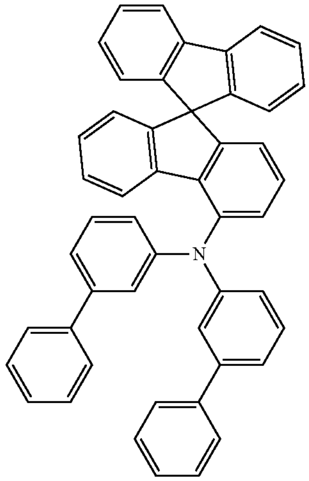
H3
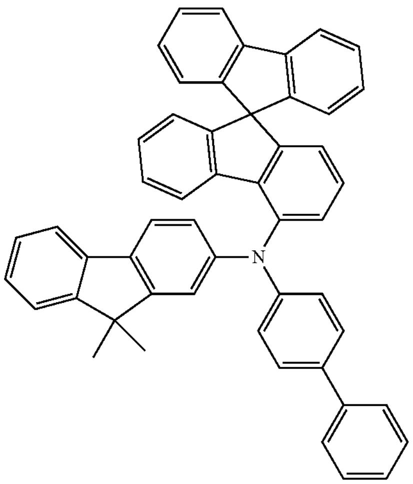

-continued
H4
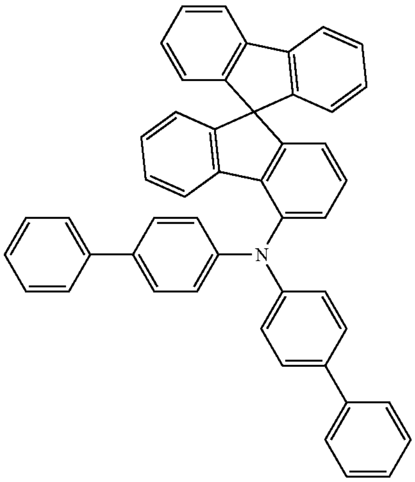
H5
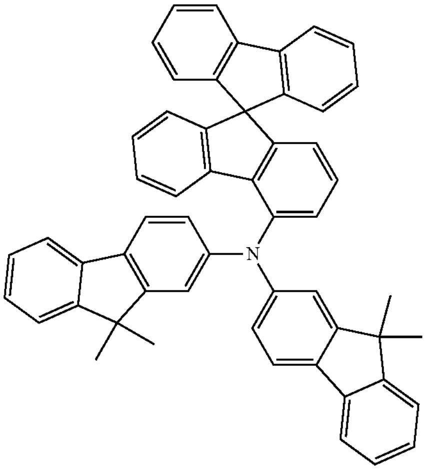
H6
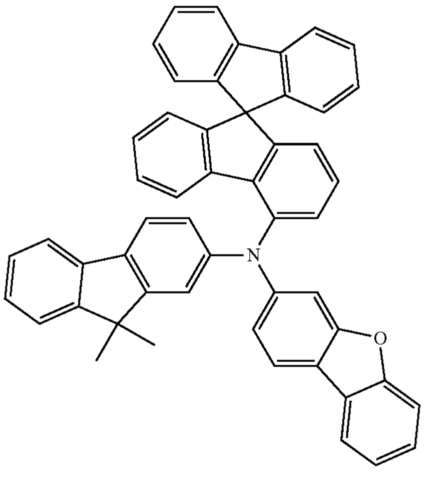
-continued
H7
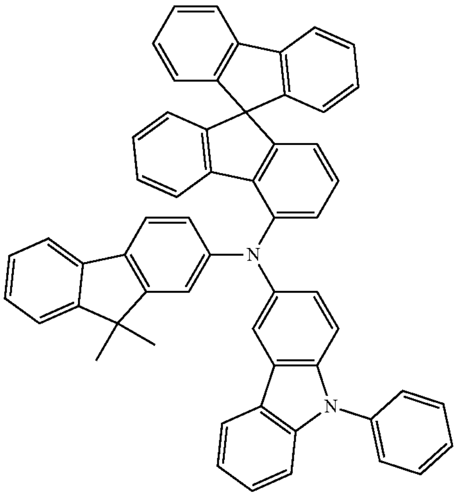
H8
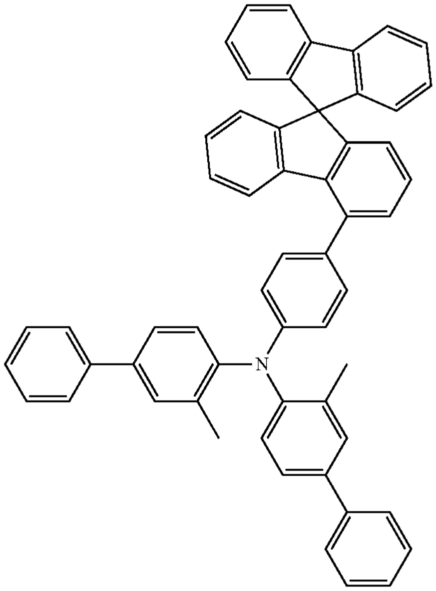

-continued
H9
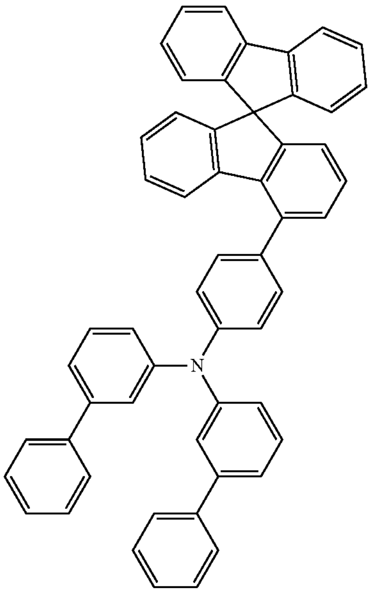
H10
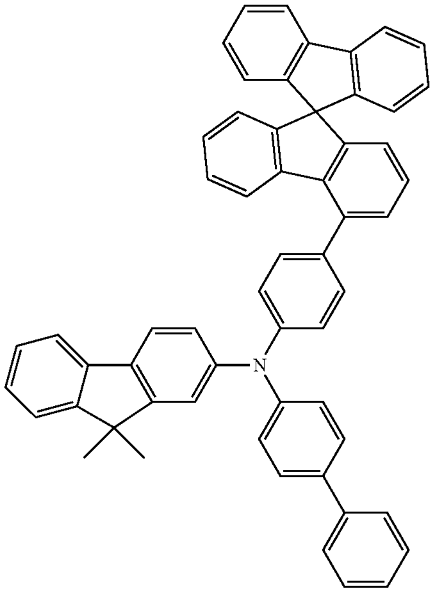
-continued
H11
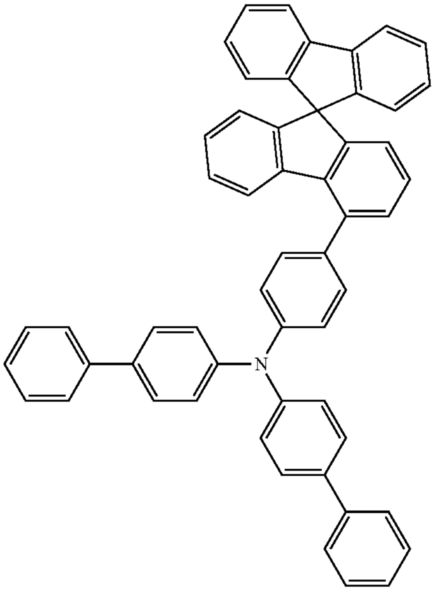
H12
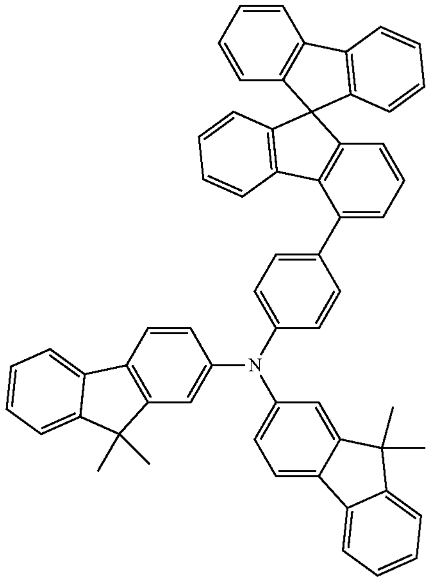

-continued
H13
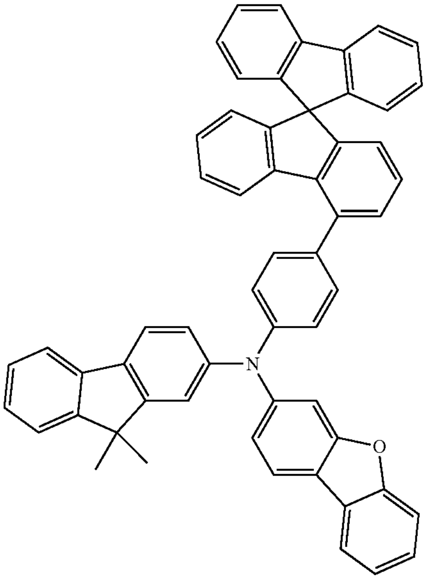
H14
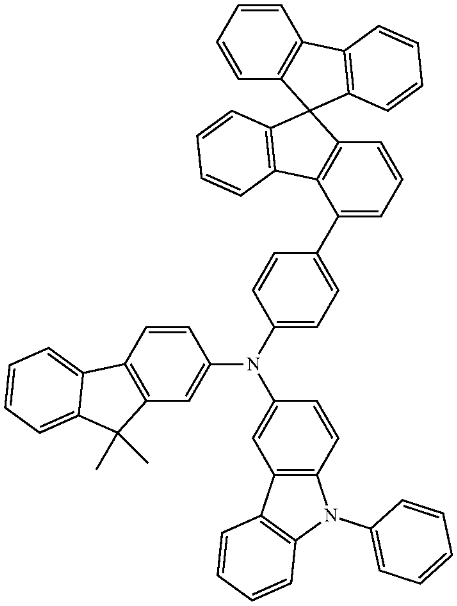
H15
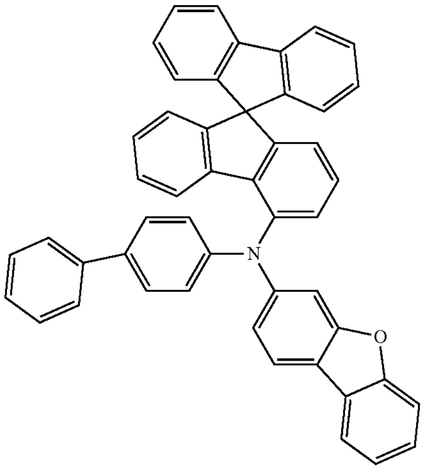
-continued
H16
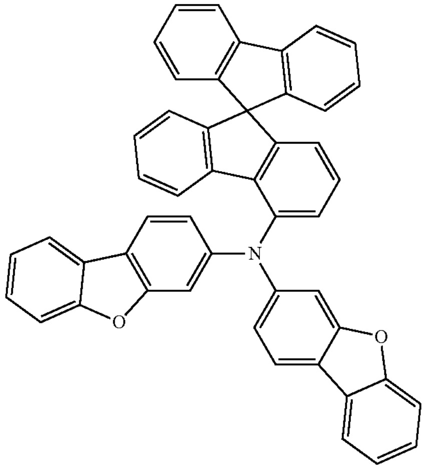
H17
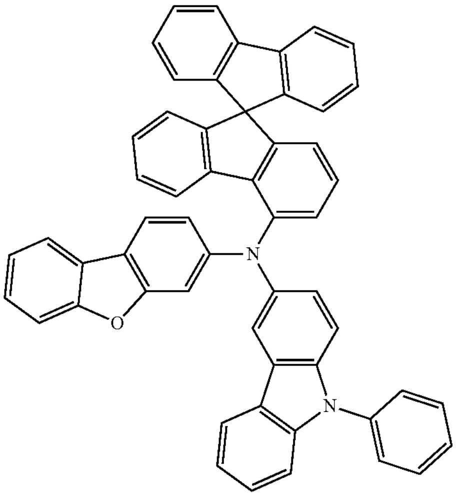
H18
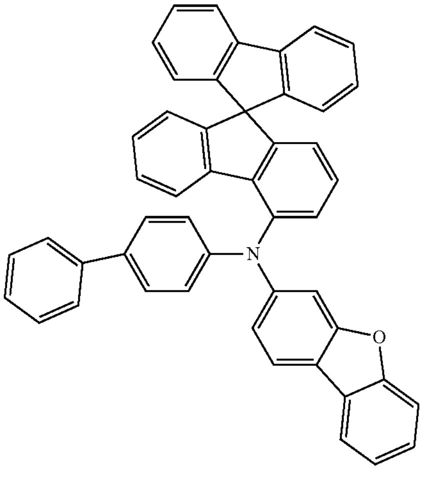

-continued

H19

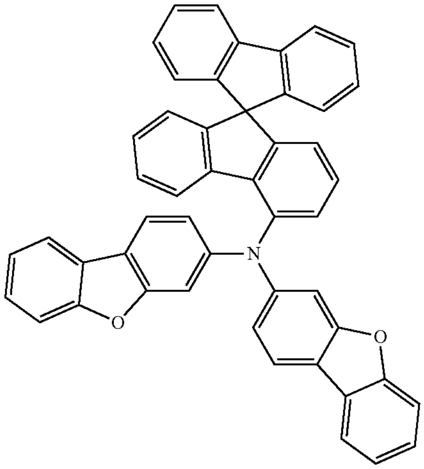

H20

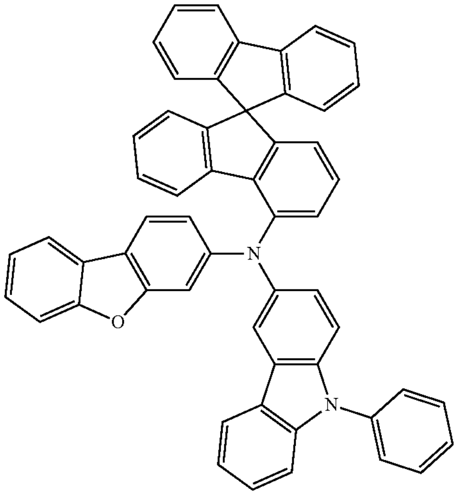

H21

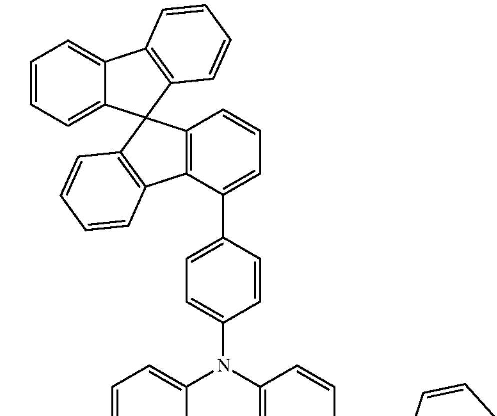

-continued

H22

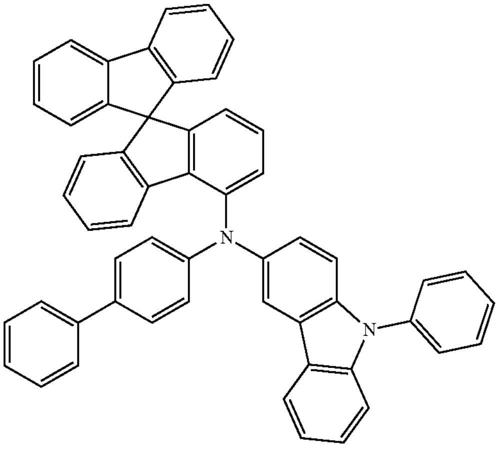

H23

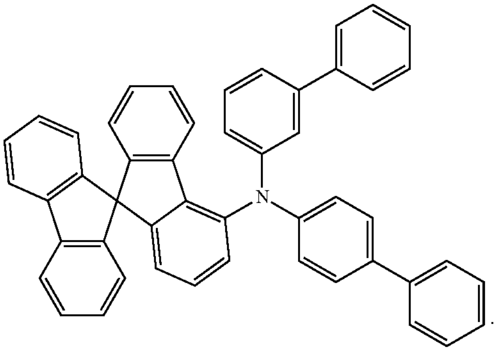

4. The organic light emitting device of claim 1, wherein the emissive layer further comprises a second emitting material layer disposed between the first emitting material layer and the second electrode and a first charge generation layer disposed between the first and second emitting material layers.

5. The organic light emitting device of claim 4, wherein the second emitting material layer emits blue light, and the second emitting material layer includes a second dopant and a second host, wherein the second dopant includes the boron-based compound, and wherein the second host includes the anthracene-based compound having the structure of Formula 3.

6. The organic light emitting device of claim 4, wherein the emissive layer further comprises a second electron blocking layer disposed between the first charge generation layer and the second emitting material layer, and wherein the second electron blocking layer includes the amine-based compound having the structure of Formula 5.

7. The organic light emitting device of claim 4, wherein the first hole blocking layer is disposed between the first emitting material layer and the first charge generation layer, and wherein the emissive layer further comprises a second hole blocking layer disposed between the second emitting material layer and the second electrode.

8. The organic light emitting device of claim 4, wherein the emissive layer further comprises a third emitting material layer disposed between the second emitting material layer and the second electrode and a second charge generation layer disposed between the second and third emitting material layers.

9. The organic light emitting device of claim 1, wherein the substrate defines a red pixel region, a green pixel region and a blue pixel region and the organic light emitting diode is located correspondingly to the red pixel region, the green pixel region and the blue pixel region, and the organic light emitting device further comprises a color conversion layer disposed between the substrate and the organic light emitting diode or over the organic light emitting diode correspondingly to the red pixel region and the green pixel region.

10. The organic light emitting device of claim 4, wherein the second emitting material layer emits yellow-green light or red-green light.

11. The organic light emitting device of claim 8, wherein the second emitting material layer emits yellow-green light or red-green light.

12. The organic light emitting device of claim 10, wherein the substrate defines a red pixel region, a green pixel region and a blue pixel region and the organic light emitting diode is located correspondingly to the red pixel region, the green pixel region and the blue pixel region, and the organic light emitting device further comprises a color filter layer disposed between the substrate and the organic light emitting diode or over the organic light emitting diode correspondingly to the red pixel region, the green pixel region and the blue pixel region.

13. The organic light emitting device of claim 11, wherein the substrate defines a red pixel region, a green pixel region and a blue pixel region and the organic light emitting diode is located correspondingly to the red pixel region, the green pixel region and the blue pixel region, and the organic light emitting device further comprises a color conversion layer disposed between the substrate and the organic light emitting diode or over the organic light emitting diode correspondingly to the red pixel region and the green pixel region.

* * * * *